(12) United States Patent
Shah

(10) Patent No.: US 9,605,074 B2
(45) Date of Patent: Mar. 28, 2017

(54) MULTIFUNCTIONAL NANOBODIES FOR TREATING CANCER

(71) Applicant: THE GENERAL HOSPITAL CORPORATION, Boston, MA (US)

(72) Inventor: Khalid Shah, Andover, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/423,512

(22) PCT Filed: Mar. 14, 2013

(86) PCT No.: PCT/US2013/031287
§ 371 (c)(1),
(2) Date: Feb. 24, 2015

(87) PCT Pub. No.: WO2014/035474
PCT Pub. Date: Mar. 6, 2014

(65) Prior Publication Data
US 2015/0218282 A1    Aug. 6, 2015

Related U.S. Application Data

(60) Provisional application No. 61/694,895, filed on Aug. 30, 2012.

(51) Int. Cl.
| | |
|---|---|
| C07K 16/30 | (2006.01) |
| A61K 38/17 | (2006.01) |
| A61K 39/395 | (2006.01) |
| C07K 14/475 | (2006.01) |
| C07K 14/525 | (2006.01) |
| C07K 14/71 | (2006.01) |
| C07K 14/47 | (2006.01) |
| A61K 48/00 | (2006.01) |

(52) U.S. Cl.
CPC .......... *C07K 16/30* (2013.01); *A61K 38/1709* (2013.01); *A61K 39/39558* (2013.01); *C07K 14/4747* (2013.01); *C07K 14/525* (2013.01); *C07K 14/71* (2013.01); *A61K 48/00* (2013.01); *C07K 2319/00* (2013.01); *C07K 2319/035* (2013.01)

(58) Field of Classification Search
None
See application file for complete search history.

(56) References Cited

U.S. PATENT DOCUMENTS

| | | |
|---|---|---|
| 5,037,743 A | 8/1991 | Welch et al. |
| 5,143,830 A | 9/1992 | Holland et al. |
| 5,288,641 A | 2/1994 | Roizman |
| 5,501,979 A | 3/1996 | Geller et al. |
| 6,284,236 B1 | 9/2001 | Wiley et al. |
| 6,444,640 B1 | 9/2002 | Nagane et al. |
| 6,998,116 B1 | 2/2006 | Ashkenazi |
| 7,052,834 B1 | 5/2006 | Kidd et al. |
| 7,063,835 B2 | 6/2006 | Coffin |
| 7,790,451 B2 | 9/2010 | Yazaki et al. |
| 8,216,819 B2 | 7/2012 | Hermiston et al. |
| 8,222,036 B2 | 7/2012 | Thompson et al. |
| 8,236,941 B2 | 8/2012 | Yao et al. |
| 8,313,896 B2 | 11/2012 | Martuza et al. |
| 2002/0128438 A1 | 9/2002 | Seol et al. |
| 2004/0120928 A1 | 6/2004 | Frenkel |
| 2005/0214266 A1 | 9/2005 | Morris et al. |
| 2009/0155247 A1 | 6/2009 | Ashkenazi |
| 2009/0175826 A1 | 7/2009 | Subbiah et al. |
| 2009/0325867 A1 | 12/2009 | Cohen et al. |
| 2010/0240097 A1 | 9/2010 | Young et al. |
| 2010/0272686 A1 | 10/2010 | Kaur et al. |
| 2010/0305002 A1 | 12/2010 | Chenchik et al. |
| 2010/0311948 A1 | 12/2010 | Hua et al. |
| 2010/0323399 A1 | 12/2010 | Wiley et al. |
| 2011/0014656 A1 | 1/2011 | Levin et al. |
| 2011/0177032 A1 | 7/2011 | Martuza et al. |
| 2013/0211049 A1 | 8/2013 | Neville et al. |
| 2014/0094417 A1 | 4/2014 | Pastan et al. |

FOREIGN PATENT DOCUMENTS

| | | |
|---|---|---|
| WO | 02/22175 A2 | 3/2002 |
| WO | 2004/087930 A2 | 10/2004 |
| WO | 2005/000220 A2 | 1/2005 |
| WO | 2009/028870 A2 | 3/2009 |
| WO | 2009/029601 A2 | 3/2009 |
| WO | WO 2009/148488 A2 | 12/2009 |
| WO | 2012/072815 A1 | 6/2012 |
| WO | 2012/106281 A1 | 8/2012 |
| WO | 2014/150179 A1 | 9/2014 |

OTHER PUBLICATIONS

Roovers et al., Cancer Immunol Immunother. 56(3):303-317 (2007). "Efficient inhibition of EGFR signaling and of tumour growth by antagonistic anti-EGFR Nanobodies."
Oliveira et al., J Control Release. 145(2):165-75 (2010). "Downregulation of EGFR by a novel multivalent nanobody-liposome platform."
Markert et al., "High diagnostic value of morphologic examination and molecular analysis of bone marrow biopsies in a case of BCR-ABL+ CML with clusters of blasts", Int J Hematol., 89(3):294-297 (2009).
Mineta et al., "Attenuated multi-mutated herpes simplex virus-1 for the treatment of malignant gliomas", Nature Medicine, 1(9):938-943 (1995).
Miyatake et al., "Transcriptional Targeting of Herpes Simplex Virus for Cell-Specific Replication", J Virol., 1 (7):5124-5132 (1997).
Pan et al., "Synergistic induction of tumor cell death by combining cisplatin with an oncolytic adenovirus carrying TRAIL", Mol Cell Biochem., 304:315-323 (2007).
Parato et al., "Recent Progress in the Battle Between Oncolytic Viruses and Tumors", Nat Rev Cancer, 5:965-976 (2005).

(Continued)

*Primary Examiner* — Elly-Gerald Stoica
(74) *Attorney, Agent, or Firm* — Nixon Peabody LLP

(57) ABSTRACT

The technology described herein is directed to methods and compositions directed to the treatment of cancer, e.g. using multifunctional receptor targeted cancer therapeutics.

3 Claims, 24 Drawing Sheets

(56) References Cited

OTHER PUBLICATIONS

Rieger et al., "Mechanisms of Resistance of Human Glioma Cells to Apo2 ligand/TNF-Related Apoptosis-Inducing Ligand", Cell Physiol Biochem., 20:23-34 (2007).
Rozanov et al., "Engineering a leucine zipper-TRAIL homotrimer with improved cytotoxicity in tumor cells", Mol Cancer Ther., 8(6):1515-1525 (2009).
Saeki et al.,"Herpes Simplex Virus Type 1 DNA Amplified as Bacterial Artificial Chromosome in *Escherichia coli*: Rescue of Replication-Competent Virus Progeny and Packaging of Amplicon Vectors", Human Gene Therapy, 9:2787-2794 (1998).
Sasportas et al., "Assessment of therapeutic efficacy and fate of engineered human mesenchymal stem cells for cancer therapy", PNAS, 106(12):4822-48277 (2009).
Shah et al., "Bimodal Viral Vectors and In Vivo Imaging Reveal the Fate of Human Neural Stem Cells in Experimental Glioma Model", The Journal of Neuroscience, 28(17):4406-4413 (2008).
Shah et al., "Glioma Therapy and Real-Time Imaging of Neural Precursor Cell Migration and Tumor Regression", Ann Neurol., 57(1):34-41 (2005).
Shah et al., "In vivo Imaging of S-TRAIL-Medicated Tumor Regression and Apoptsis", Molecular Therapy, 11 (6):926-931 (2005).
Shah et al., "Real-time imaging of TRAIL-induced apoptosis of glioma tumors in vivo", Oncogene 22:6865-6872 (2003).
Shen et al., "Construction and characterization of two versions of bifunctional EGFP-sTRAIL fusion proteins", Appl Microbiol Biotechnol., 76:141-149 (2007).
Smith et al., "The TNF Receptor Superfamily of Cellular and Viral Proteins: Activation, Constimulation, and Death", Cell, 76:959-062 (1994).
Sprenger et al., "LOCATE: a mammalian protein subcellular localization database", Nucleic Acids Research, 36: D230-D233 (2008).
Stern et al., "Improving mammalian cell factories: The selection of signal peptide has a major impact on recombinant protein synthesis and secretion in mammalian cells", Cell and Molecular Biology, 2:1-17 (2007).
Stieglmaier et al., "Selective induction of apoptosis in leukemic B-lymphoid cells by a CD19-specific TRAI fusion protein", Cancer Immunol Immunother, 57:233-246 (2008).
Tamura et al., "Multimechanistic Tumor Targeted Oncolytic Virus Overcomes Resistance in Brain Tumor", The American Society of Gene and Cell Therapy, 21(1):68-77 (2013).
Tashker et al., "Post-Cytochrome C Protection from Apoptosis Conferred by a MAPK Pathway in Xenopus Egg Extracts", Mol Biol Cell, 13:393-401 (2002).
Todo et al., "Oncolytic herpes simplex virus vector with enhanced MHC class I presentation and tumor cell killing" PNAS, 98(11):6396-6401 (2001).
Todo et al., "Armed oncolytic herpes simplex viruses for brain tumor therapy", Cell Adhesion Migration, 2(3):208-213 (2008).
Varghese et al., "Oncolytic herpes simplex virus vectors for cancer virotherapy", Cancer Gene Therapy, 9:967-978 (2002).
Wakimoto et al., "Human Glioblastoma-Derived Cancer Stem Cells: Establishment of Invasive Glioma Models and Treatment with Oncolytic Herpes Simplex Virus Vectors", Cancer Research, 69(8):3472-3481 (2009).
Wen et al., "Malignant Gliomas in Adults", N Engl J Med., 359(5):492-507 (2008).
Wiezorek et al., "Death Receptor Agonists as a Targeted Therapy for Cancer", Clin Cancer Res., 16(6):1701-1708 (2010).
Wohlfahrt et al., "A Capsid-Modified, Conditionally Replicating Oncolytic Adenovirus Vector Expressing TRAIL Leads to Enhanced Cancer Cell Killing in Human Glioblastoma Models", Cancer Research, 67(8):8783-8790 (2007).
Xia et al., "Opposing effects of ERK and JNK-p38 MAP kinases on apoptosis", Science, 270.5240:1326-1331 (1995).
Yamamoto et al., "Imaging immediate-early and strict-late promoter activity during oncolytic herpes simplex virus type 1 infection and replication in tumors", Gene Therapy, 13:731-1736 (2006).
Yip et al., "Stem-cell based therapies for brain tumors", Current Opinion in Molecular Therapeutics, 10(4):334-342 (2008).
Badran et al., "Target cell-restricted apoptosis inducation by 528scFv-TRAIL fusion protein specific for human EGFR and expressed in *Escherichia coli*", International Journal of Oncology, 36(5):1229-1234 (2010).
Aghi et al., "Oncolytic viral therapies—the clinical experience", Oncogene, 24:7802-7816 (2005).
Allan et al., "Inhibition of caspase-9 through phosphorylation at Thr 125 by ERK MAPK", Nat Cell Biol., 5(7):647-654 (2003).
An et al, "Drug Interactions between the Proteasome Inhibitor Bortezomib and Cytotoxic Chemotherapy, Tumor Necrosis Factor (TNF) beta, and TNF-Related Apoptosis-Inducing Ligand in Prostate Cancer", Clin. Ca. Res., 9:4537-4545 (2003).
Ashkenazi et al., "Ligand-Based Targeting of Apoptosis in Cancer: The Potential of Recombinant Human Apoptosis Ligand 2/Tumor Necrosis Factor-Related Apoptosis-Inducing Ligand (rhApo2L/ TRAIL)", J Clin Oncol 26(21): 3621-30 (2008).
Bagci-Onder et al., "A dual PI3K/mTOR Inhibitor, PI-103, Cooperates with Stem Cell-Delivered TRAIL in Experimental Glioma Models", Cancer Research, 71(1):154-63 (2011).
Barash et al., "Human secretory signal peptide description by hidden Markov model and generation of a strong artificial signal peptide for secreted protein expression", Biochem Biophys Res Commun, 294(4):835-842 (2002).
Breitbach et al., "Intravenous delivery of a multi-mechanistic cancer-targeted oncolytic poxvirus in humans", Nature, 477:99-102 (2011).
Bremer et al., "Exceptionally Potent Anti-Tumor Bystander Activity of an scFv:sTRAIL Fusion Protein with Specificity for EGP2 Toward Target Antigen-Negative Tumor Cells", Neoplasia, 6(5):636-645 (2004).
Bremer et al., "Simultaneous Inhibition of Epidermal Growth Factor Receptor (EGFR) Signaling and Enhanced Activation of Tumor Necrosis Factor-related Apoptosis-inducing Ligand (TRAIL) Receptor-mediated Apoptosis Induction by an scFv:sTRAIL Fusion Protein with Specificity for Human EGFR", J. Biol. Chem., 280(11):10025-10033 (2005).
Bremer et al., "Target Cell-Restricted Apoptosis Induction of Acute Leukemic T Cells by a Recombinant Tumor Necrosis Factor-Related Apoptosis-Inducing Ligand Fusion Protein with Specificity for Human CD7", Cancer Res., 65 (8):3380-3388 (2005).
Bremer et al., "Targeted delivery of a designed sTRAIL mutant results in superior apoptotic activity towards EGFR-positive tumor cells", J Mol Med., 86(8):909-924 (2008).
Choo et al., "SPdb—a signal peptide database", BMC Bioinformatics, 6:249 (2005).
Compte et al., "Tumor Immunotherapy Using Gene-Modified Human Mesenchymal Stem Cells Loaded into Synthetic Extracellular Matrix Scaffolds", Stem Cells, 27(3):753-760 (2009).
Corsten et al., "MicroRNA-21 Knockdown Disrupts Glioma Growth in vivo and Displays Synergistic Cytotoxicity with Neural Precursor Cell-Delivered S-TRAIL in Human Gliomas", Cancer Res., 67(19):8994-9000 (2007).
Corsten et al., "Therapeutic stem-cells for cancer treatment: hopes and hurdles in tactical warfare", Lancel Oncol., 9(4):376-384 (2008).
Ehtesham et al., "Induction of Glioblastoma Apoptosis Using Neural Stem Cell-mediated Delivery of Tumor Necrosis Factor-related Apoptosis-inducing Ligand", Cancer Res., 62(24):7170-7174 (2002).
Erhardt et al., "B-Raf Inhibits Programmed Cell Death Downstream of Cytochrome c Release from Mitochondria by Activating the MEK/Erk Pathway", Mol Cell Biol., 19(8):5308-5315 (1999).
Fukuhara et al., "Triple Gene-Deleted Oncolytic Herpes Simplex Virus Vector Double-Armed with Interleukin 18 and Soluble B7-1 Constructed by Bacterial Artificial Chromosome-Mediated System", Cancer Res., 65(23):10663-10668 (2005).
Han et al., "Development of a second-generation oncolytic Herpes simplex virus expressing TNF alpha for cancer therapy", J Gene Med., 9(2):99-106 (2007).

(56) References Cited

OTHER PUBLICATIONS

Hingtgen et al., "A Novel Molecule Integrating Therapeutic and Diagnostic Activities Reveals Multiple Aspects of Stem Cell-Based Therapy", Stem Cells, 28(4):832-841 (2010).
Hingtgen et al., "Targeting multiple pathways in gliomas with stem cell and viral delivered S-TRAIL and Temozolomide", Mol Cancer Ther., 7(11):3575-3585 (2008).
Hoffman et al., "Comparison of herpes simplex virus- and conditionally replicative adenovirus-based vectors for glioblastoma treatment", Cancer Gene Therapy, 14(7):627-639 (2007).
Holmstrom et al., "MAPK/ERK signaling in activated T cells inhibits CD95/Fas-mediated apoptosis downstream of DISC assembly", EMBO Journal, 19(20):5418-5428 (2000).
Jacobson et al., "Programmed Cell Death in Animal Development", Cell, 88: 347-354 (1997).
Johnstone et al., "The TRAIL apoptotic pathway in cancer onset, progression and therapy", Nat Rev Cancer, 8(10): 782-798 (2008).
Kanai et al., "A Novel Oncolytic Herpes 1-15 Simplex Virus that Synergizes with Phosphoinositide 3-kinase/Akt Pathway Inhibitors to Target Glioblastoma Stem Cells", Clinical Cancer Research, 17(11):3686-3696 (2011).
Kelley et al., "Preclinical Studies to Predict the Disposition of Apo2L/Tumor Necrosis Factor-Related Apoptosis-Inducing Ligand in Humans: Characterization of in Vivo Efficacy, Pharmacokinetics, and Safety", J Pharmacol Exp Ther., 299(1):31-38 (2001).
Kirn et al., "Replication-selective virotherapy for cancer: Biological principles, risk management and future directions", Nat Med 7(7):781-787 (2001).
Kirshner et al., "Identification of TRAIL as an Interferon Regulatory Factor 3 Transcriptional Target", Journal of Virology, 79(14):9320-9324 (2005).
Kock et al., "Tumor Therapy Mediated by Lentiviral Expression of shBcl-2 and S-TRAIL", Neoplasia, 9(5):435-442 (2007).
Kuijlen et al., "Review: on TRAIL for malignant glioma therapy?", Neuropathology and Applied Neurobiology, 36 (3):168-182 (2010).
Kuroda et al., "Flip-Flop HSV-BAC: bacterial artificial chromosome based system for rapid generation of recombinant herpes simplex virus vectors using two independent site-specific recombinases", BMC Biotechnology, 6:40 (2006).
Kurozumi et al., "Effect of Tumor Microenvironment Modulation on the Efficacy of Oncolytic Virus Therapy", J Natl Cancer Inst., 99(23):1768-1781 (2007).
Leblanc et al., "Apo2L/TRAIL and its death and decoy receptors", Cell Death and Differentiation, 10(1):66-75 (2003).
Leopardi et al., "The herpes simplex virus major regulatory protein ICP4 blocks apoptosis induced by the virus or by hyperthermia", PNAS, 93(18):9583-9587 (1996).
Leopardi et al., "The herpes simplex virus 1 protein kinase US3 is required for protection from apoptosis induced by the virus" PNAS, 94(15):7891-7896 (1997).
Liu et al., "Clinical trial results with oncolytic virotherapy: a century of promise, a decade of progress", Nat Clin Pract Oncol., 4(2):101-117 (2007).
Lubkowski et al., "The structural basis of phage display elucidated by the crystal structure of the N-terminal domains of g3p", Nature Struct. Biol., 5(2):140-147 (1998).
Markert et al., "Conditionally replicating herpes simplex virus mutant G207 for the treatment of malingnt glioma: results of a phase I trial", Gene Therapy, 7(10):867-874 (2000).
Markert et al., "Phase Ib Trial of Mutant Herpes Simplex Virus G207 Inoculated Pre-and Post-tumor Resection for Recurrent GBM", Molecular Therapy, 17(1):199-207 (2009).
Martinelli et al. Clinical and Experimental Immunology 158(1):1-9 (2009). "Anti-epidermal growth factor receptor monoclonal antibodies in cancer therapy."
Shah et al., Cancer Res. 64(9):3236-3242 (2004). "Inducible release of TRAIL fusion proteins from a proapoptotic form for tumor therapy."
Wang et al., Cancer Biol Ther. 6(6):980-7 (2007). "In vitro efficacy of immuno-chemotherapy with anti-EGFR human Fab-Taxol conjugate on A431 epidermoid carcinoma cells."
Bremer et al.,Mol. Therapy 16(12):1919-1926 (2008). "Potent systemic anticancer activity of adenovirally expressed EGFR-selective TRAIL fusion protein".
Kauer et al., Nature Neuroscience, 15(2):197-204 (2011). "Encapsulated therapeutic stem cells implanted in the tumor resection cavity induce cell death in glioma."
Badran et al., "Target cell-restricted apoptosis induction by 528scFv-TRAIL fusion protein specific for human EGFR and expressed in *Escherichia coli*", International Journal of Oncology 36(5):1229-1234 (2010).
Baradaran et al., "Recombinant Expression and Purification of Pseudomonas aeruginosa Truncated Exotoxin A in *Escherichia coli*", Pharmaceutical Sciences 19(1):31-34 (2013).
Foley et al., "Mutations in the Elongation Factor 2 Gene Which Confer Resistance to Diphtheria Toxin and Pseudomonas Exotoxin A", The Journal of Biological Chemistry 270(39):23218-23225 (1995).
Liu et al., "Expression of an Anti-CD3 Single-Chain Immunotoxin with a Truncated Diphtheria Toxin in a Mutant CHO Cell Line", Protein Expression and Purification 19(2):304-311 (2000).
Moehring et al., "Selection and Characterization of Cells Resistant to Diphtheria Toxin and Pseudonomas Exotoxin A: Presumptive Translation Mutants", Cell 11(12):447-454 (1977).
Theuer et al., "A Recombinant Form of Pseudomonas Exotoxin Directed at the Epidermal Growth Factor Receptor That Is Cytotoxic without Requiring Proteolytic Processing", The Journal of Biological Chemistry 267(24):16872-16877 (1992).
Wang et al., "Development of a nonintegrating Rev-dependent lentiviral vector carrying diphtheria toxin A chain and human TRAF6 to target HIV reservoirs", Gene Therapy 17(9):1063-1076 (2010).

5A

5B

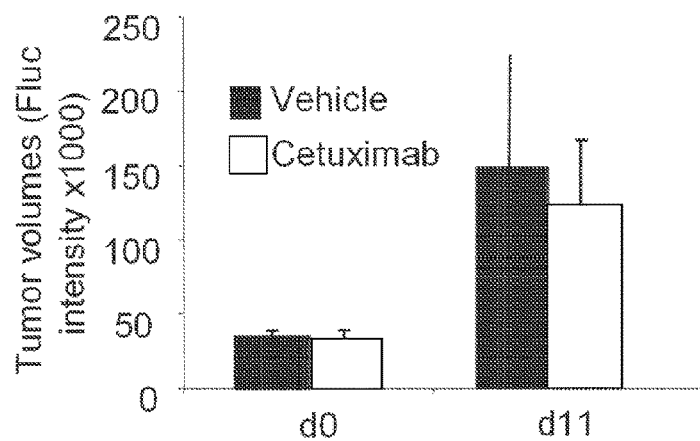
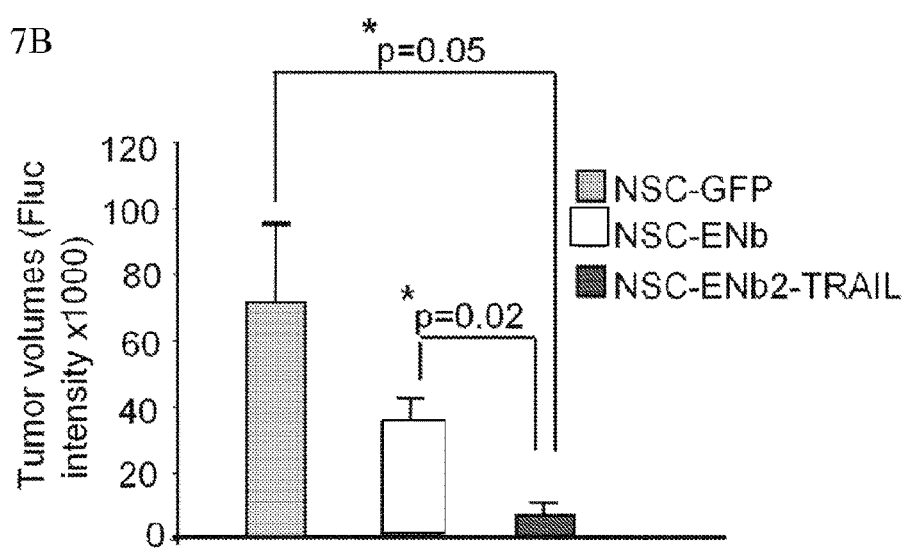
Figures 7A-7F

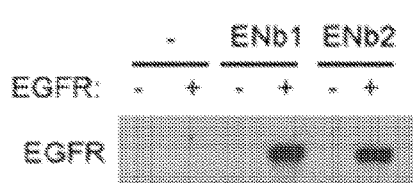
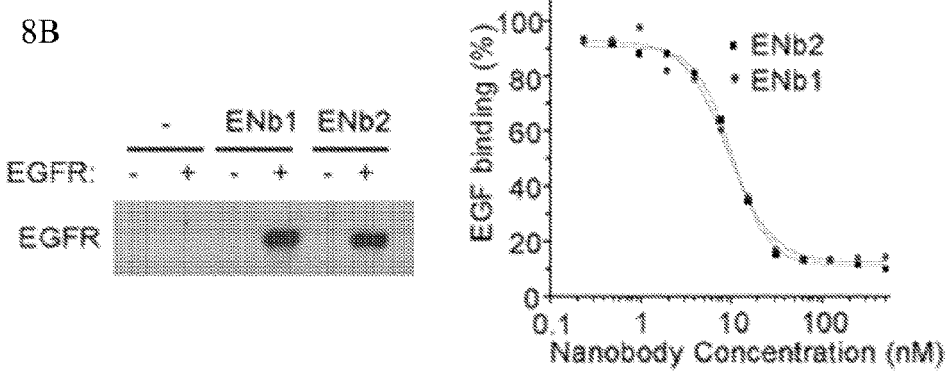
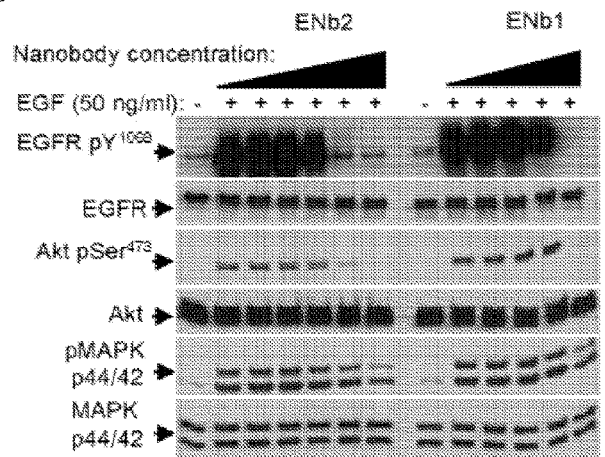
Figures 8A-8I

8E
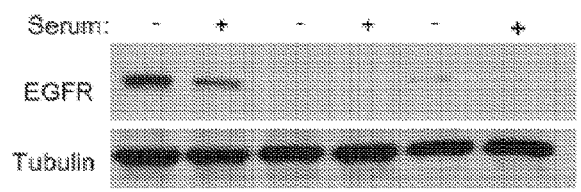
8F
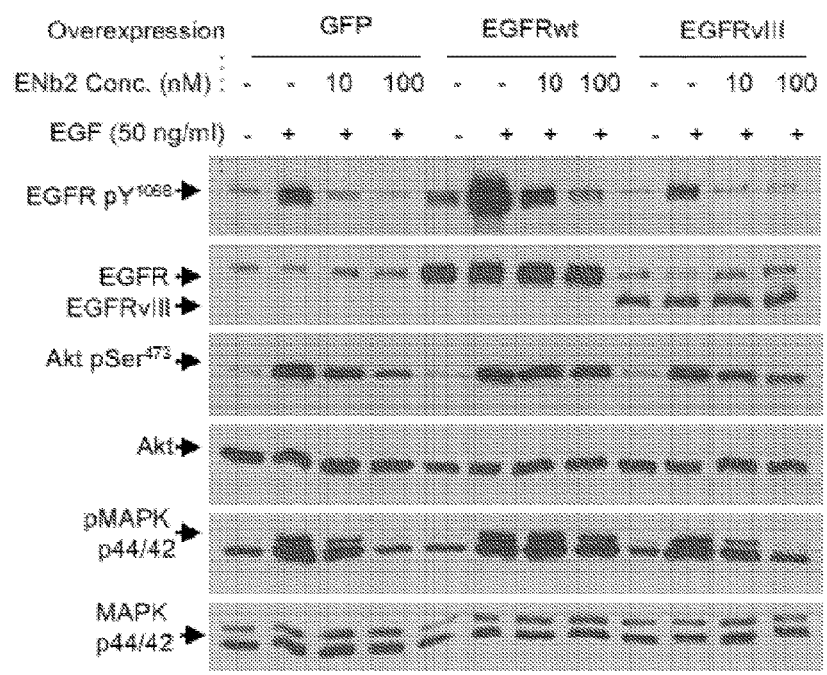
Figures 8A-8I (cont)

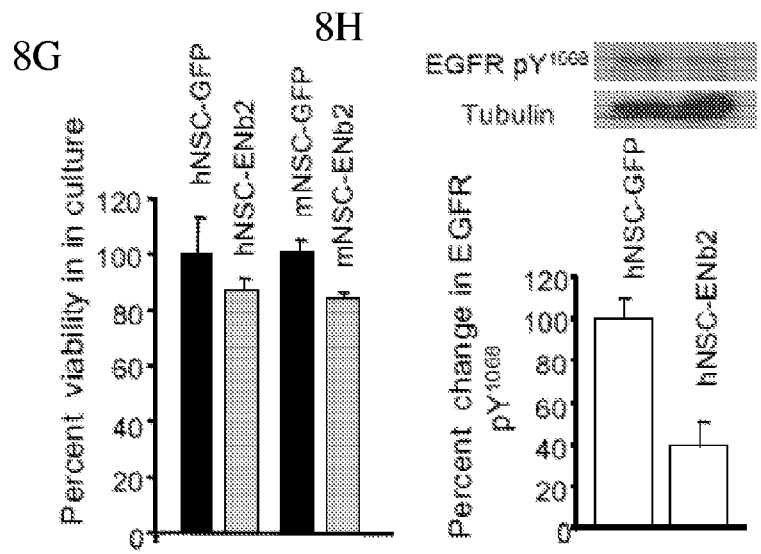
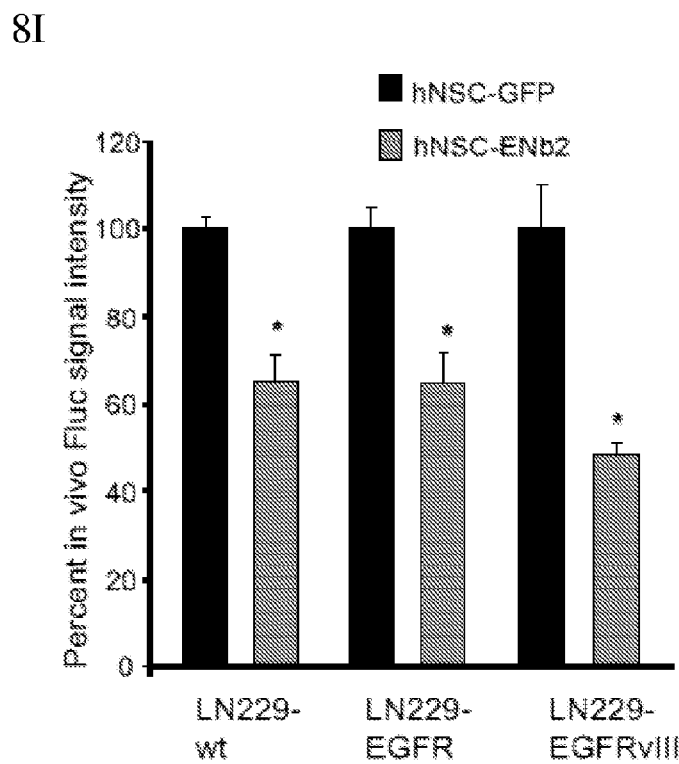
Figures 8A-8I(cont)

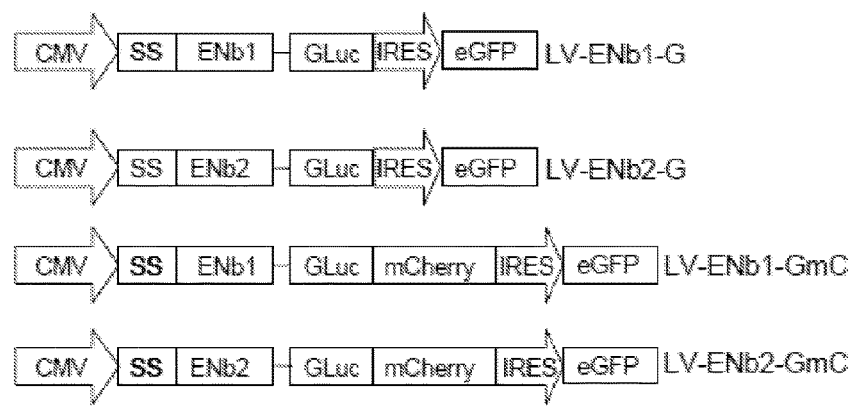
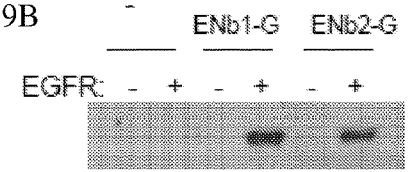
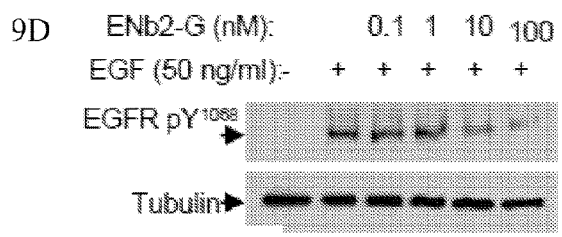
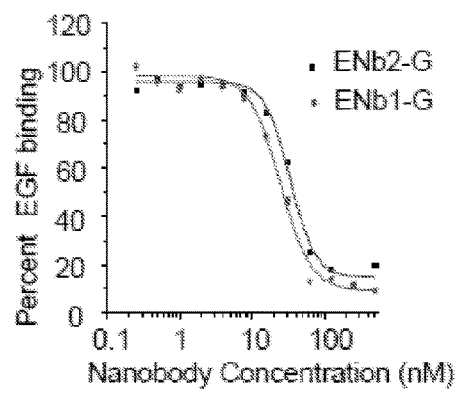
Figures 9A-9K

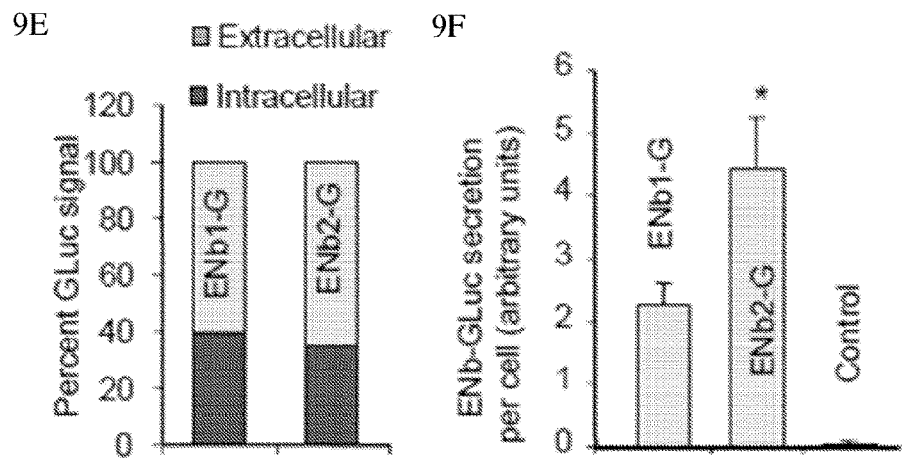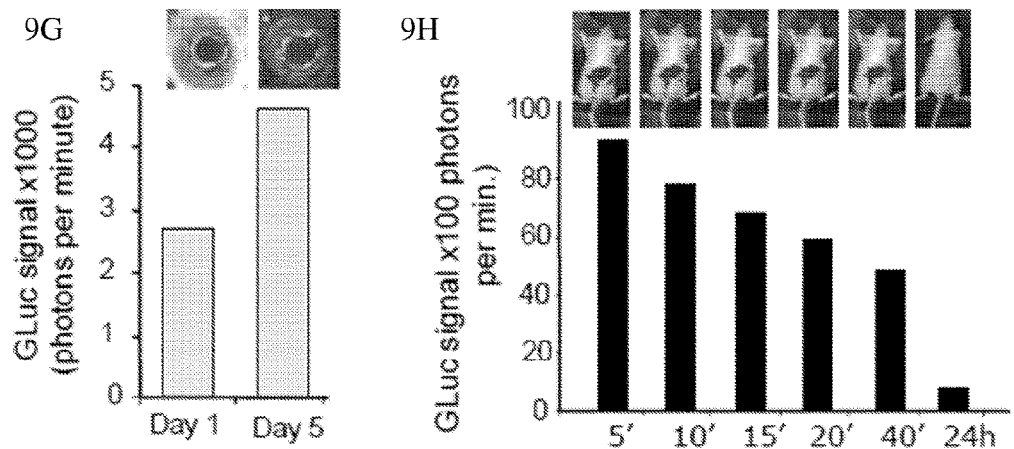
Figures 9A-9K (cont)

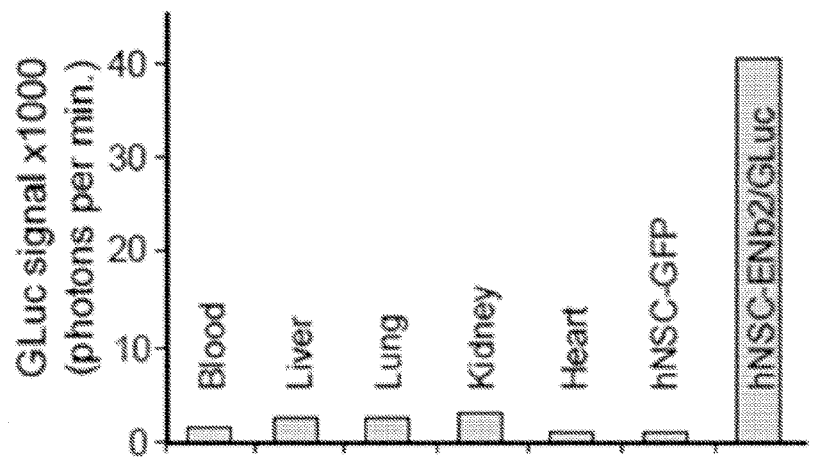
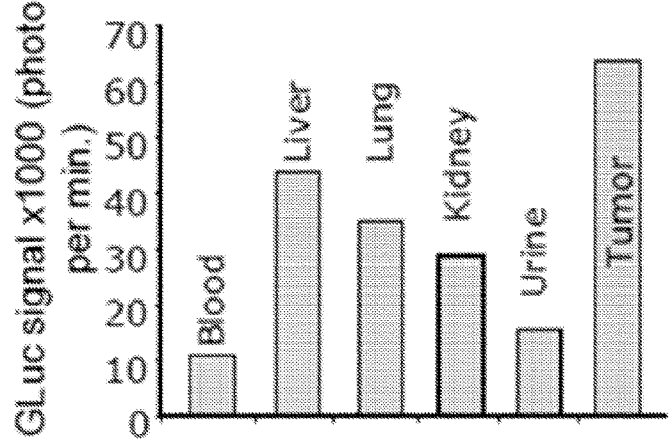
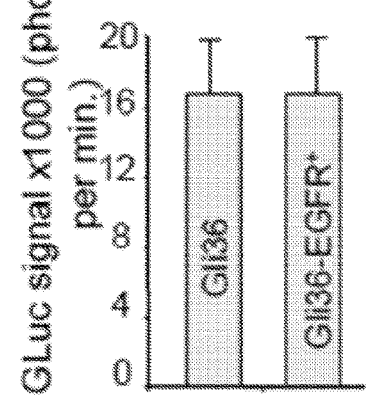
Figures 9A-9K (cont)

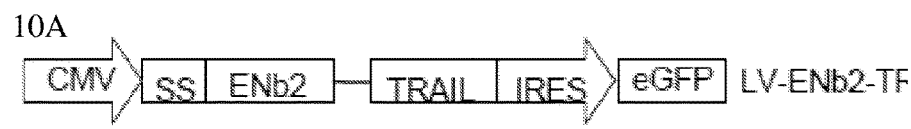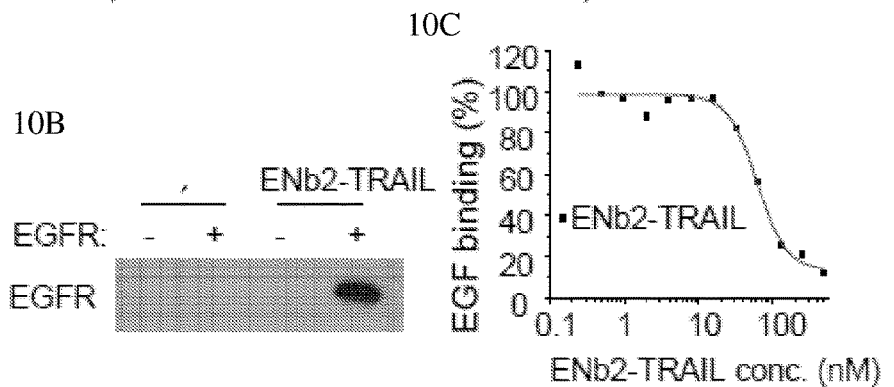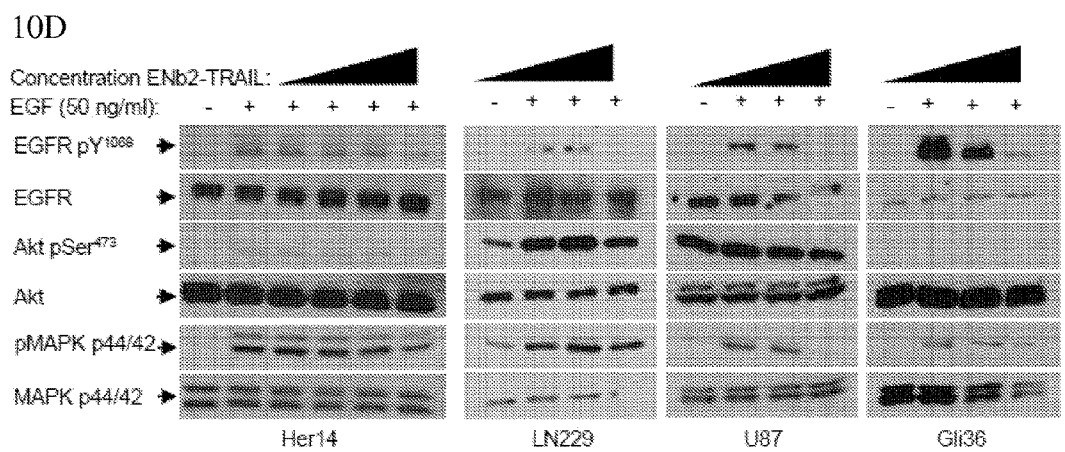
Figures 10A-10H

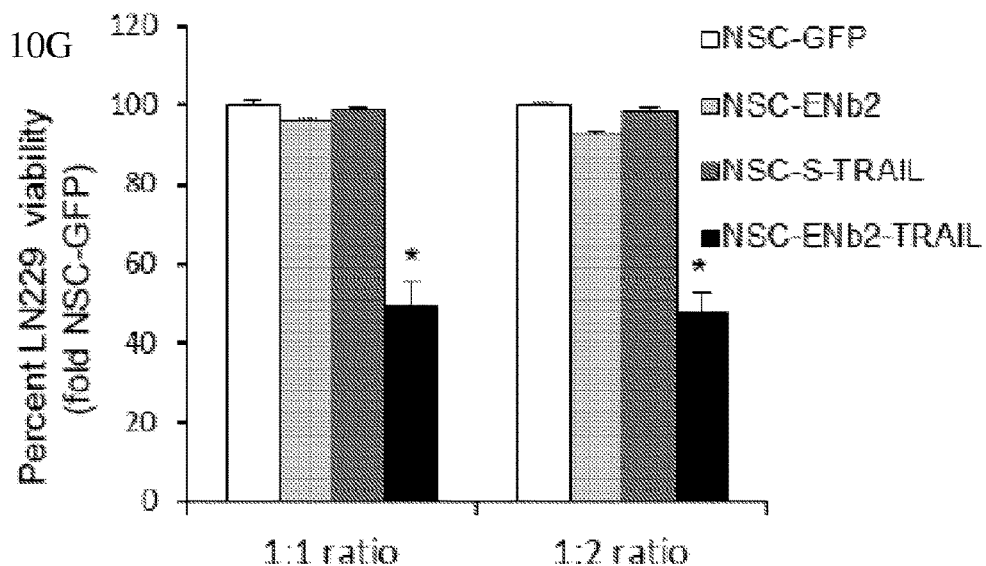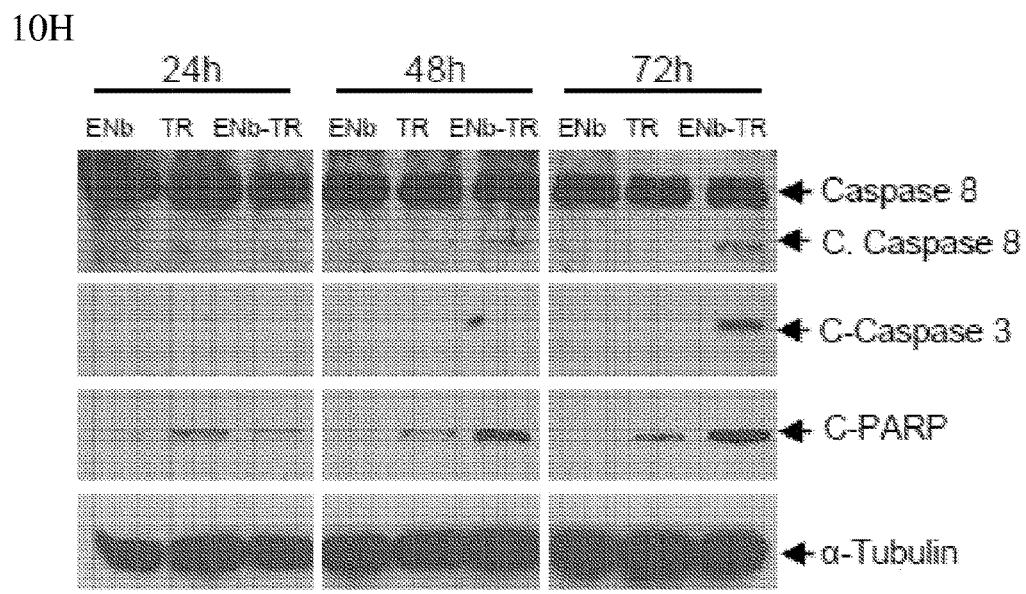
Figures 10A-10H (cont)

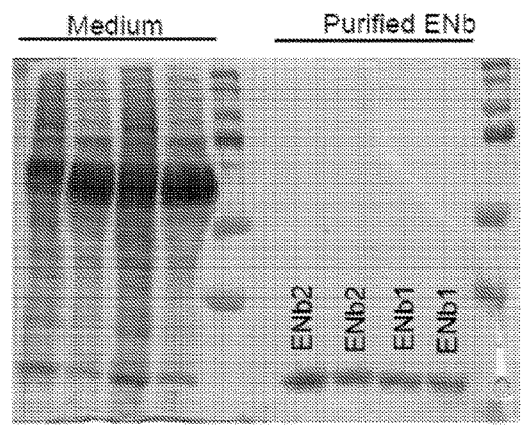
Figure 13
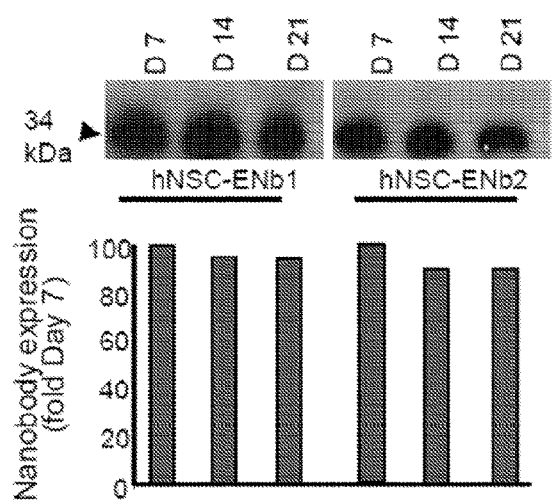
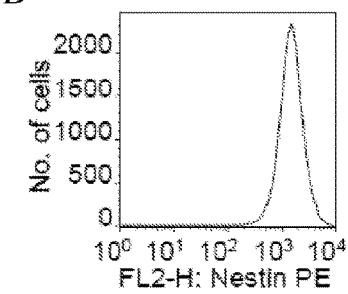
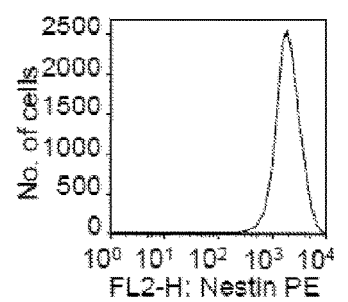
Figures 14A-14C

MULTIFUNCTIONAL NANOBODIES FOR TREATING CANCER

CROSS-REFERENCE TO RELATED APPLICATIONS

This application is a 35 U.S.C. §371 National Phase Entry Application of International Application No. PCT/US2013/31287 filed Mar. 14, 2013, which designates the U.S., and which claims benefit under 35 U.S.C. §119(e) of U.S. Provisional Application No. 61/694,895 filed Aug. 30, 2012, the contents of which are incorporated herein by reference in their entirety.

GOVERNMENT SUPPORT

This invention was made with federal funding under Grant Nos. RO1 CA138922 and RO1 NS071197 awarded by the National Institutes of Health. The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 20, 2013, is named 030258-075241-PCT_SL.txt and is 38,932 bytes in size.

TECHNICAL FIELD

The technology described herein relates to compositions and methods for treating cancer.

BACKGROUND

Epidermal growth factor receptor (EGFR) has a significant role in the progression of tumors, with many tumors showing abnormal expression and/or activity of EGFR. Over the past two decades, much effort has been directed at developing anticancer agents that can interfere with EGFR activity and arrest tumor growth and, in some cases, cause tumor regression. The most commonly used pharmacologic approaches to inhibit EGFR signaling are small-molecule receptor tyrosine kinase inhibitors (smRTKI), like Gefinitib (Iressa, ZD1839) and Erlotinib (Tarceva, OSI-774) and monoclonal antibodies (mAb), such as Cetuximab (Erbitux, Mab-C225), Panitumumab (ABX-EGF) and Matuzumab (EMD72000). Whereas smRTKI exert their effects at the intracellular domain of EGFR to prevent tyrosine kinase activity, mAbs sterically block ligand binding to the extracellular domain of the receptor (3, 4). Although, the use of Erlotinib and Gefitinib have had moderate success in clinical trials in different tumor types, the use of mAbs has had limited to no success in cancer patients (3). Additionally, the efficacy of EGFR-targeting agents is limited in several tumor types, particularly in the highly malignant glioblastoma multiforme (GBM).

SUMMARY

As demonstrated herein, the inventors have developed novel therapeutic molecules, termed "multifunctional receptor targeted cancer therapeutics" (MRTCTs). In some embodiments, MRTCTs can bind to and modulate the activity of at least two receptors on the surface of a cancer cell. The inventors have demonstrated that the modulation of two receptors provides surprising levels of efficacy, permitting the MRTCT to inhibit tumor growth in cancer types which are normally resistant to the modulation of each of the receptors individually.

Further, the inventors have demonstrated that MRTCTs can be delivered by cells, e.g. stem cells. Certain types of stem cells, e.g. neural stem cells, will reliably home to particular tissues, where they can express and/or secrete a MRTCT, permitting improved delivery to a tumor located in that tissue. The combination of MRTCTs and stem cell delivery is demonstrated herein to be efficacious in the treatment of a number of cancers, including but not limited to, glioblastoma.

In one aspect, the technology described herein relates to a multifunctional receptor targeted cancer therapeutic comprising two portions capable of binding specifically to receptors on cancer cells and targeting a broad spectrum of tumors that are resistant to either portion. In one aspect, the technology described herein relates to a multifunctional receptor targeted cancer therapeutic comprising a first portion capable of specific binding with a cancer cell receptor and a second portion comprising a therapeutic molecule.

In some embodiments, the first portion can comprise an antibody reagent. In some embodiments, the antibody reagent can be a nanobody reagent. In some embodiments, the first portion can comprise a ligand or ligand mimetic. In some embodiments, the cancer cell receptor can be EGFR. In some embodiments, the first portion can inhibit EGFR signaling.

In some embodiments, the second portion can be capable of binding specifically with a second cancer cell receptor. In some embodiments, the second cancer cell receptor can be DR4 or DR5. In some embodiments, the binding of the second portion can activate apoptosis. In some embodiments, the therapeutic molecule can be selected from the group consisting of TRAIL; an extracellular domain of human TRAIL; and S-TRAIL. In some embodiments, the extracellular domain of human TRAIL can comprise amino acids 114-281 of SEQ ID NO: 1.

In some embodiments, the first and second portions can be joined by a linker polypeptide sequence. In some embodiments, the linker polypeptide can be N-terminal to the second portion and C-terminal to the first portion. In some embodiments, the linker polypeptide sequence can comprise at least 8 amino acids. In some embodiments, the linker polypeptide can comprise the amino acid sequence of SEQ ID NO: 4.

In some embodiments, the multifunctional receptor targeted cancer therapeutic can further comprise a signal sequence. In some embodiments, the multifunctional receptor targeted cancer therapeutic can further comprise an isoleucine zipper domain.

In one aspect, the technology described herein relates to a nucleic acid molecule encoding the multifunctional receptor targeted cancer therapeutic as described herein. In one aspect, the technology described herein relates to a vector comprising a nucleic acid molecule as described herein. In some embodiments, the vector can be a lentiviral or adenoviral vector.

In one aspect, the technology described herein relates to a cell comprising a vector, a nucleic acid, or a multifunctional receptor targeted cancer therapeutic as described herein. In some embodiments, the cell can be a stem cell. In some embodiments, the stem cell can be a neural stem cell or a mesenchymal stem cell. In some embodiments, the multifunctional receptor targeted cancer therapeutic can be secreted by the cell.

In some embodiments, the cell can be encapsulated in a matrix or scaffold. In some embodiments, the matrix can comprise a synthetic extracellular matrix. In some embodiments, the matrix can be biodegradable. In some embodiments, the synthetic extracellular matrix can comprise a thiol-modified hyaluronic acid and a thiol reactive cross-linker molecule. In some embodiments, the thiol reactive cross-linker molecule can be polyethylene glycol diacrylate.

In one aspect the technology described herein relates to a pharmaceutical composition comprising a cell, vector, nucleic acid or multifunctional receptor targeted cancer therapeutic as described herein and optionally, a pharmaceutically acceptable carrier.

In one aspect, the technology described herein relates to a method comprising administering a therapeutically effective amount of a composition as described herein to a subject in need of treatment for cancer. In some embodiments, the subject can be in need of treatment for brain cancer, glioblastoma, lung cancer, breast cancer, and colon cancer. In some embodiments, the stem cell can be a type that will home to the tissue in which the cancer is located. In some embodiments, the cancer can be brain cancer and the stem cell can be a neural stem cell or mesenchymal stem cell. In some embodiments, the composition can be administered intravenously.

In one aspect, the technology described herein relates to the use of a pharmaceutical composition, cell, vector, nucleic acid, or multifunctional receptor targeted cancer therapeutic as described herein for the treatment of cancer.

BRIEF DESCRIPTION OF THE DRAWINGS

FIG. 2A depicts Western blot analysis showing the EGFR specificity of ENb2-TRAIL on NIH3T3 and Her14 cell lines incubated with or without ENb2-TRAIL. FIG. 2B depicts the results of ELISA demonstrating the EGF competition by ENb2-TRAIL. FIG. 2C depicts Western blot analysis demonstrating inhibition of EGFR and downstream signaling via the AKT and MAPK pathways on serum-starved Her14 cells incubated with ENb2-TRAIL. FIG. 2D depicts Western blot analysis demonstrating ENb2-TRAIL induction of apoptosis.

FIG. 3A depicts the results of experiments in which serum starved LN229 GBM cells were pre-treated with ENb-TRAIL (NT) then stimulated with EGF, protein lysates were immunoprecipated with EGFR antibody and blotted with different antibodies. FIG. 3B depicts the results of experiments in which GBM6 were treated with TRAIL (T) or ENb-TRAIL (NT) for 4 h, protein lysates were immunoprecipated with DR5 antibody and blotted with different antibodies.

FIG. 4A depicts a graph of experiments in which serum starved LN229 GBM cells were pre-treated with ENb-TRAIL (NT) then stimulated with EGF. EGFR and its downstream effector AKT, MAPK and mTOR were analyzed. FIG. 4B depicts a graph which demonstrates that PI3K/mTOR dual inhibitor PI103 sensitizes TRAIL-induced apoptosis. LN229 GBM cells were treated with TRAIL plus different doses of PI103 or ENb-TRAIL alone. Whole cell lysates were collected and analyzed with antibodies as indicated.

FIG. 5A depicts a graph demonstrating relative GBM cell viability in co-culture or after incubation with conditioned medium from mNSC expressing GFP, ENb2 or ENb2-TRAIL for 72 hours as determined by measuring FLuc activity. FIG. 5B depicts a graph of caspase 3/7 activity in co-culture of GBM cells and mNSC.

FIG. 7A depicts a graph of tumor volumes measured by FLuc bioluminescence imaging signal intensity of nude mice bearing U87-MG-mCherry-FLuc intracranial tumors and injected with Cetuximab (1 mg/mouse/day) or vehicle daily for one week. FIG. 7B depicts a graph of tumor volumes of nude mice bearing established intracranial U87-MG-mCherry-FLuc tumors treated with NSC expressing GFP, ENb2 or ENb2-TRAIL. FIGS. 7C-7E depict photomicrographs of H&E stained sections of the brain of GBM-bearing mice treated with NSC-GFP (7C), NSC-ENb2 (7D) and NSC-ENb2-TRAIL (7E) showing the changes in tumor volumes and mCherry+ tumor cells. FIG. 7F depicts a plot demonstrating the extent of cleaved caspase-3 staining in brain sections of NSC-GFP, NSC-ENb2, and NSC-ENb2-TRAIL treated mice. Plot shows the number of cleaved caspase-3 cells in different treatment groups (original magnification: ×20.). For 7A and 7B, data were represented as mean±SEM and * denotes p<0.05, students t-test)

FIGS. 8A-8I demonstrate the functionality of anti-EGFR nanobodies released from neural stem cells. FIG. 8A depicts a schematic representation of lentiviral transfer vectors bearing anti-EGFR nanobody cDNAs. FIG. 8B depicts Western blot analysis showing the EGFR specificity of nanobodies on EGFR-negative [NIH3T3 (−)] and EGFR-positive [Her14 (+)] cell lines incubated with or without ENbs. FIG. 8C a graph of ELISA showing the EGF competition by anti-EGFR nanobodies. EGFR ectodomain/Fc fusion protein was incubated with serial dilutions of nanobody and 800 pM biotinylated EGF. EGFR ectodomain-bound biotinylated EGF was detected using peroxidase-labelled streptavidin. FIG. 8D depicts Western blot analysis showing inhibition of EGFR activation and downstream signaling in serum-starved Her14 cells incubated anti-EGFR nanobodies. FIG. 8E depicts Western blot analysis showing EGFR expression levels in NSC and U87 GBM cells. FIG. 8F depicts Western blot analysis showing inhibition of EGFR activation and downstream signaling in serum-starved LN229 GBM cells overexpressing either EGFR wt., EGFRvIII or GFP incubated with anti-EGFR nanobodies. FIG. 8G depicts a plot showing changes in GBM cell numbers measured by changes in Fluc bioluminescence intensity when co-cultured for 3 days with hNSC or mNSC expressing ENb2 or mNSC-ENb2 or GFP control. FIG. 8H depicts Western blot analysis and quantification of the band intensity showing the inhibition of EGFR activation in LN229 co-cultures with hNSC-ENb2 or hNSC-GFP after 72 hours. FIG. 8I depicts a plot showing changes in GBM growth in mice implanted with a mix of LN229-mCherry-Fluc overexpressing either EGFR wt., EGFRvIII and hNSC-ENb2 and controls NSC-GFP 72 hrs post implantation. Data were represented as mean±SEM and * denotes p<0.05, students t-test.

FIGS. 9A-9K demonstrate the pharmacokinetics of anti-EGFR nanobodies in vitro and in vivo: FIG. 9A depicts a schematic representation of lentiviral transfer vectors bearing imageable anti-EGFR nanobodies (ENb1 and ENb2) genetically fused to Gaussia luciferase (GLuc) or to a fusion of GLuc and mCherry. FIG. 9B depicts Western blot analysis showing the EGFR specificity of GLuc nanobody variants on EGFR-negative [NIH3T3 (−)] and EGFR-positive [Her14 (+)] cell lines incubated with or without Enb-GLuc. FIG. 9C depicts a graph of ELISA showing the EGF competition by anti-EGFR Enb-GLuc variants. FIG. 9D depicts Western blot analysis showing inhibition of EGFR activation by Nanobody-GLuc variants on serum-starved Her14 cells incubated with serial dilutions of ENb2-G. FIG. 9E depicts a graph of gluc bioluminescence assay showing the presence of nanobody-GLuc fusion proteins intracellularly and in the culture medium in human NSC expressing ENb1-G and ENb2-G. FIG. 9F depicts a graph of dual bioluminescence assay on human NSC co-expressing GFP-FLuc and ENb1-G or ENb2-G showing the ratio of nanobody-GLuc fusion in the culture medium and the relative cell number by measurement of GLuc and FLuc activity, respectively. FIG. 9G depicts a graph of combined intravital microscopy and bioluminescence imaging of U87-FLuc-TdTomato GBM-bearing SCID mice implanted subcutaneously with human NSC expressing ENb2-G in a dorsal skinfold window chamber. Mice were imaged on day 1 and 5 post NSC implantation by bioluminescence imaging for the secretion of ENb2-G (FIG. 9G) and by intravital microscopy for the fate of NSC (data not shown). FIG. 9H depicts a graph of In vivo bioluminescence imaging of purified ENb2-G injected into mice bearing established Gli36-Fluc-mCherry tumors by i.v. injection and analyzed at different time points after coelenterazine injection. FIG. 9I depicts a graph of ex vivo analysis of biodistribution of NSC-delivered ENb2-G assessed by GLuc imaging of organs. FIG. 9J depicts a graph of ex vivo analysis of biodistribution of systemically administered purified ENb2-G assessed by GLuc imaging of organs. FIG. 9K depicts graph of mice bearing Gli36-Fluc-mCherry (left flank) and the EGFR over-expressing Gli36-FLuc-mCherry-EGFR+ (right flank) subcutaneous tumors given purified ENb2-G protein intravenously and imaged for GLuc. Representative image and summary graph showing localization of ENb2-G in mice. In all panels, error bars represent the standard deviation. Data were represented as mean±SEM and * denotes p<0.05, students t-test FIGS. 10A-10H demonstrate the efficacy of the dual effector molecule ENb2/TRAIL.

FIG. 12A depicts a schematic of the mouse brain showing the implantation site and the site adjacent to the lateral ventricle where GBM cell migration was evaluated. FIG. 12B depicts a graph of relative cell viability of different newly isolated GBM lines (G001-004) 48 hours after treatment with ENb2, Enb2-TRAIL (100 ng/mL) and control conditioned medium. data were represented as mean±SEM, * denotes p<0.05, students t-test FIG. 13 demonstrates the purification of EGFR target nanobodies. ENbs produced by HEK293T cells in serum free DMEM were purified from the medium using protein A/G coated beads. Purified protein (1 µg) and corresponding medium (10 µl) were analyzed by SDS-PAGE and Coomassie Blue staining of the gel, to determine the purity of the batch.

FIGS. 14A-14C demonstrate that NSC retain their intrinsic properties post-modification. FIG. 14A depicts a graph of nanobody expression. FIGS. 14B-14C depict flow cytometric analysis on NSC-ENb1 (14B), NSC ENb2 (14C) showing nestin expression 21 days post-lentiviral transduction.

FIG. 15D depicts Western blot analysis showing the overexpression of EGFR wt and EGFRvIII in LN229 cells.

FIG. 17A depicts a graph of relative cell numbers of GBM cell lines LN229, U87 and Gli36 incubated with different concentrations of S-TRAIL after 24 hrs later. FIG. 17B depicts Western blot analysis of U87 and Gli36 GBM lines treated with ENb2 and ENb2-TRAIL showing activation of PARP.

FIGS. 18A-18B depict immunoblots and plots showing the changes in DR5 protein expression in U87 cells expressing either control shRNA or shDR5 (18A) and subsequent PARP cleavage (18B) upon treatment with Enb2-TRAIL in control shRNA or shDR5 expressing U87 cells. DR5 knock down and PARP cleavage in U87 cells was normalized to α-Tubulin. FIG. 18C depicts a graph of cell viability of U87 and U87-shDR5 treated with Enb2-TRAIL. Bars represent Mean+/−SD.

DETAILED DESCRIPTION

Figure 1:
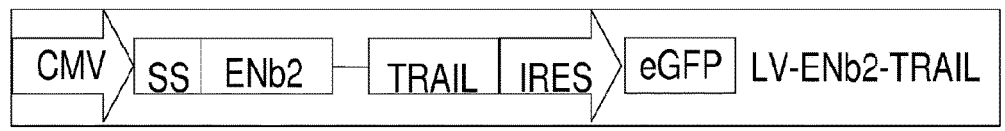
FIG. 1 depicts schematic examples of MRCT: ENb-linker-TRAIL (ENb-TRAIL).

Described herein are compositions and methods relating to multifunctional receptor targeted cancer therapeutics and, e.g., their use in the treatment of cancer. As used herein, the terms "multifunctional receptor targeted cancer therapeutic" or "MRTCT" refer to a molecule comprising at least two portions, wherein the first portion is capable of specific binding with at least one cancer cell receptor and the second portion comprises a therapeutic molecule. In some embodiments, each of the two portions is capable of specific binding with separate cancer cell receptors, e.g. the first portion specifically binds with at least a first cancer cell receptor and the second portion specifically binds with at least a second cancer cell receptor. As described herein, the MRTCT can, in some embodiments, inhibit the growth of a broad spectrum of tumors that are resistant to either portion individually.

As used herein, the term "cancer cell receptor" refers to a receptor polypeptide (e.g. a polypeptide that binds specifically to a molecule in the extracellular environment) that is present on the surface of a cancer cell. A cancer cell receptor can be a receptor displayed exclusively on cancer cells, a receptor displayed at a higher level on cancer cells than normal cells of the same or different tissue types, or a receptor displayed on both cancerous and normal cell types. In some embodiments, a cancer cell receptor can be a receptor that, in cancer cells, has altered (e.g. higher or lower than normal) expression and/or activity. In some embodiments, a cancer cell receptor can be a receptor that is implicated in the disease process of cancer. In some embodiments, a cancer cell receptor can be a receptor that is involved in the control of cell death and/or apoptosis. In some embodiments, a MRTCT binds both a receptor that is implicated in the disease process of cancer and a receptor that is involved in the control of cell death and/or apoptosis. Non-limiting examples of cancer cell receptor can include, EGFR, ER, PR, HER2, PDGFR, VEGFR, MET, c-MET, ALK, CD117, RET, DR4, DR5, and FasR.

As used herein, the term "EGFR" or "Epidermal Growth Factor Receptor" refers to a transmembrane receptor that binds to ligands including epidemeral growth factor "EGF" and TGFα. Ligand recognition causes autophosphorylation of EGFR and activates the MAPK, Akt, and/or JNK pathways and leading to cellular proliferation. The sequences of EGFR are well known in the art, eg. human EGFR (NCBI Gene ID:1956) (SEQ ID NO: 5 (mRNA) and SEQ ID NO: 6 (polypeptide)).

As used herein, the term "DR4" or "Death Receptor 4" refers to a tumor necrosis factor (TNF) receptor family that binds to ligands including TRAIL. DR4 comprises as death domain (DD) and activates apoptotic signaling. The sequences of DR4 are well known in the art, eg. human DR4 (NCBI Gene ID: 8797) (SEQ ID NO: 7 (mRNA) and SEQ ID NO: 8 (polypeptide)).

As used herein, the term "DR5" or "Death Receptor 5" refers to a tumor necrosis factor (TNF) receptor family that binds to ligands including TRAIL. The sequences of DR5 are well known in the art, eg. human DR5 (NCBI Gene ID: 8795) (SEQ ID NO: 9 (mRNA) and SEQ ID NO: 10 (polypeptide)).

In some embodiments, one or more portions can comprise an antibody reagent. In some embodiments, the first portion can comprise an antibody reagent. In some embodiments, the second portion can comprise an antibody reagent. As used herein, the term "antibody reagent" refers to a polypeptide comprising a monoclonal antibody or antigen-binding domain of a monoclonal antibody that includes at least one immunoglobulin variable domain or immunoglobulin variable domain sequence and which specifically binds a given antigen. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')$_2$, Fd fragments, Fv fragments, scFv, and single domain antibodies (dAb) (de Wildt et al., Eur J. Immunol. 1996; 26(3):629-39)) as well as complete antibodies. In particular embodiments, an antibody can have the structural features of IgA, IgG, IgE, IgD, IgM (as well as subtypes thereof). Antibodies can be from any source, including primate (human and non-human primate) and primatized antibodies.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; Kabat definitions are used herein). Each VH and VL is typically composed of three CDRs and four FRs, arranged from amino-terminus to carboxy-terminus in the following order: FR1, CDR1, FR2, CDR2, FR3, CDR3, FR4.

One or more regions of an antibody can be human or effectively human. For example, one or more of the variable regions can be human or effectively human. For example, one or more of the CDRs can be human, e.g., HC (heavy chain) CDR1, HC CDR2, HC CDR3, LC (light chain) CDR1, LC CDR2, and LC CDR3. One or more of the framework regions can be human, e.g., FR1, FR2, FR3, and FR4 of the HC or LC. For example, at least 70, 75, 80, 85, 90, 91, 92, 93, 94, 95, 96, 97, 98, 99, or 100% of an immunoglobulin variable domain, the constant region, the constant domains (CH1, CH2, CH3, CL1), or the entire antibody can be human or effectively human. Fully human monoclonal antibodies also can be prepared by immunizing mice transgenic for large portions of human immunoglobulin heavy and light chain loci. Following immunization of these mice (e.g., XENOMOUSE™ (Abgenix), HUMAB-MOUSE™ (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

The terms "antigen-binding fragment" and "antigen-binding domain" are used herein to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546), which consists of a VH or VL domain; and (vi) an isolated complementarity determining region (CDR) that retains specific antigen-binding functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242: 423-426; and Huston et al. (1988) Proc. Natl. Acad. Sci. USA 85:5879-5883.

Antibody fragments can be obtained using any appropriate technique including conventional techniques known to those of skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

Antibodies and antibody reagents can be raised against a polypeptide or portion of a polypeptide by methods known to those skilled in the art. Antibodies are readily raised in animals such as rabbits or mice by immunization with the gene product, or a fragment thereof (e.g., PSA or PSMA). Immunized mice are particularly useful for providing sources of B cells for the manufacture of hybridomas, which in turn are cultured to produce large quantities of monoclonal antibodies. While both polyclonal and monoclonal antibodies can be used in the methods described herein, it is preferred that a monoclonal antibody is used where conditions require increased specificity for a particular protein.

Phage display can also be particularly effective in identifying antibody reagents useful for the methods and assays described herein. For example, in order to identify aptamers for use in the methods described herein, briefly, one prepares a phage library (using e.g., m13, fd, or lambda phage), displaying inserts from 4 to about 80 amino acid residues using conventional procedures. The inserts can represent, for example, a completely degenerate or biased array. One then can select phage-bearing inserts which bind to a target polypeptide or fragments thereof. This process can be repeated through several cycles of reselection of phage that bind to the target molecule. Repeated rounds lead to enrichment of phage bearing particular sequences. DNA sequence analysis can be conducted to identify the sequences of the expressed polypeptides. The minimal linear portion of the sequence that binds to the target polypeptide can be determined. One can repeat the procedure using a biased library containing inserts containing part, or all, of the minimal linear portion plus one or more additional degenerate residues upstream or downstream thereof. Yeast two-hybrid screening methods also may be used to identify polypeptides that bind to the target polypeptide or fragment thereof. Thus, target polypeptides or fragments thereof can be used to screen peptide libraries, including phage display libraries, to identify and select peptide binding partners of the target polypeptide. Phage display can also be used to identify antibodies or antibody domains specific for a target, see, e.g. Barbas et al. PNAS 1991 88:7978-82; Burton et al. 1991 PNAS 88:10134-7; Yang et al. 1995 J Mol Biol 254:392-403; Barbas et al. PNAS 1994 91:3809-13; Barbas et al. PNAS 1992 89:4457-61 each of which is incorporated by reference herein in its entirety.

In some embodiments, an antibody reagent can be a nanobody reagent. As used herein, the term "nanobody" refers to an antibody comprising the small single variable domain (VHH of antibodies obtained from camelids and dromedaries. Antibody proteins obtained from members of the camel and dromedary (*Camelus baclrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994; which is incorporated by reference herein in its entirety).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J. 17: 3512-3520; each of which is incorporated by reference herein in its entirety. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody. The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitate drug transport across the blood brain barrier. See U.S. patent application 20040161738 published Aug. 19, 2004; which is incorporated by reference herein in its entirety. These features combined with the low antigenicity to humans indicate great therapeutic potential.

Examples of antibody reagents which bind to and inhibit EGFR are known in the art and commercially available, e.g. an inhibitory monoclonal antibody is available as Cat No. 05-101 from Millipore; Billerica, Mass. and anti-EGFR nanobodies have been previously described in the art, see e.g. Roovers R C, et al. (2007) Cancer Immunol Immunother 56:303-317 and Roovers R C, et al. Int J Cancer; each of which is incorporated by reference herein in its entirety.

In some embodiments, a portion of an MRTCT can specifically bind a receptor by virtue of being a ligand or ligand mimetic of the receptor, e.g. in the case of TRAIL as described below herein. As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. In some embodiments, "selectively binds" or "specifically binds" can refer to the ability of a polypeptide domain described herein to bind to a target, such as a molecule present on the cell-surface, with a $K_D$ of $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay.

In some embodiments, one portion of the MRTCT can bind specifically to EGFR. In some embodiments, the binding of a portion of the MRTCT to EGFR inhibits EGFR signaling, e.g. by sterically inhibiting the binding of EGFR to its natural ligand. Methods for measuring EGFR signaling are known in the art and include, by way of non-limiting example, the level of activated (e.g. phosphorylated EGFR) in a cell can be determined by Western blotting with a anti-phospho EGFR antibody as described in the Examples herein (e.g. with anti-phosphorylated EGFR1068 antibody, Cat. No. ab-32086 (AbCam, Inc.; Cambridge, Mass.).

In some embodiments, one portion of the MRTCT can bind specifically to DR4 and/or DR5. In some embodiments, the binding of a portion of the MRTCT to DR4 and/or DR5 increases apoptosis signaling, e.g. by activating DR4 and/or DR5. Assays for measuring cell death are known in the art, e.g. apoptotic death of Jurkat cells are described below herein. In some embodiments, the portion of the MRTCT that binds specifically to DR4 and/or DR5 and increases apoptosis signaling can be a therapeutic TRAIL variant, TRAIL, an extracellular domain of TRAIL, an extracellular domain of human TRAIL, and/or S-TRIAL. As used herein, the term "therapeutic TRAIL variant" refers to a polypeptide, or a nucleotide sequence encoding such a polypeptide, comprising an extracellular domain of human TRAIL as described in U.S. Pat. No. 6,284,236, the contents of which are herein incorporated in their entirety by reference.

Tumour necrosis factor-related apoptosis-inducing ligand (TRAIL) is normally expressed on both normal and tumour cells as a non-covalent homotrimeric type-II transmembrane protein (memTRAIL). In addition, a naturally occurring soluble form of TRAIL (solTRAIL) can be generated due to alternative mRNA splicing or proteolytic cleavage of the extracellular domain of memTRAIL and thereby still retaining tumour-selective pro-apoptotic activity. TRAIL utilizes an intricate receptor system comprising four distinct membrane receptors, designated DR4, DR5, TRAIL-R3 and TRAIL-R4. Of these receptors, only DR4 and TRAIL-2 transmit an apoptotic signal. These two receptors belong to a subgroup of the TNF receptor family, the so-called death receptors (DRs), and contain the hallmark intracellular death domain (DD). This DD is critical for apoptotic signalling by death receptors (J. M. A. Kuijlen et al., Neuropathology and Applied Neurobiology, 2010 Vol. 36 (3), pp. 168-182).

Apoptosis is integral to normal, physiologic processes that regulate cell number and results in the removal of unnecessary or damaged cells. Apoptosis is frequently dysregulated in human cancers, and recent advancements in the understanding of the regulation of programmed cell death pathways has led to the development of agents to reactivate or activate apoptosis in malignant cells. This evolutionarily conserved pathway can be triggered in response to damage to key intracellular structures or the presence or absence of extracellular signals that provide normal cells within a multicellular organism with contextual information.

TRAIL activates the "extrinsic pathway" of apoptosis by binding to DR4 and/or DR5, whereupon the adaptor protein Fas-associated death domain and initiator caspase-8 are recruited to the DD of these receptors. Assembly of this "death-inducing signaling complex" (DISC) leads to the sequential activation of initiator and effector caspases, and ultimately results in apoptotic cell death. The extrinsic apoptosis pathway triggers apoptosis independently of p53 in response to pro-apoptotic ligands, such as TRAIL. DR4 can induce apoptosis after binding non-cross-linked and cross-linked sTRAIL. DR5 can only be activated by cross-linked sTRAIL. Death receptor binding leads to the recruitment of the adaptor FADD and initiator procaspase-8 and 10 to rapidly form the DISC. Procaspase-8 and 10 are cleaved into its activated configuration caspase-8 and 10. Caspase-8 and 10 in turn activate the effector caspase-3, 6 and 7, thus triggering apoptosis.

DR4 and DR5 are ubiquitously expressed on a variety of tumour types. Importantly for the compositions and methods described herein, DR4 and DR5 are also expressed in the tumour tissue from astrocytoma grade II and glioblastoma patients. In a study on 62 primary GBM tumour specimens, DR4 and DR5 were expressed in 75% and 95% of the tumours, respectively. Of note, a statistically significant positive association was identified between agonistic TRAIL receptor expression and survival. Highly malignant tumours express a higher amount of TRAIL receptors in comparison with less malignant tumours or normal tissue. In general DR5 is more frequently expressed on tumour cells than DR4.

Accordingly, the term "Tumour necrosis factor-related apoptosis-inducing ligand" or "TRAIL" as used herein refers to the 281 amino acid polypeptide having the amino acid sequence of: MAMMEVQGGPSLGQTCVLIVIFTV-LLQSLCVAVTYVYFTNELKQMQDKYSKSGIAC FLKEDDSYWDPNDEESMNSPCWQVKWQLRQLVRK-MILRTSEETISTVQEKQQNISPL VRERGPQRVAAHIT-GTRGRSNTLSSPNSKNEKALGRKINSWESSRSGHS-FLSNLHLRN GELVIHEKGFYYIYSQTYFRFQEEIKENTKNDKQM-VQYIYKYTSYPDPILLMKSARNS CWSKDAEYGLY-SIYQGGIFELKENDRIFVSVTNEHLIDMDHEASFFGA-FLVG (SEQ ID NO: 1), as described by, e.g., NP_003801.1, together with any naturally occurring allelic, splice variants, and processed forms thereof. Typically, TRAIL refers to human TRAIL. The term TRAIL, in some embodiments of the aspects described herein, is also used to refer to truncated forms or fragments of the TRAIL polypeptide, comprising, for example, specific TRAIL domains or residues thereof. Reference to any such forms of TRAIL can be identified in the application, e.g., by "TRAIL (39-281)." The amino acid sequence of the human TRAIL molecule as presented in SEQ ID NO: 1 comprises an N-terminal cytoplasmic domain (amino acids 1-18), a transmembrane region (amino acids 19-38), and an extracellular domain (amino acids 39-281). The extracellular domain comprises the TRAIL receptor-binding region. TRAIL also has a spacer region between the C-terminus of the transmembrane domain and a portion of the extracellular domain This spacer region, located at the N-terminus of the extracellular domain, consists of amino acids 39 through 94 of SEQ ID NO: 1. Amino acids 138 through 153 of SEQ ID NO: 1 correspond to a loop between the 13 sheets of the folded (three dimensional) human TRAIL protein.

As used herein, a "therapeutic TRAIL module," "therapeutic TRAIL domain," or "therapeutic TRAIL variant" refers to a polypeptide, or a nucleotide sequence encoding such a polypeptide, comprising an extracellular domain of human TRAIL, such as a human TRAIL of SEQ ID NO: 1, and maintaining TRAIL apoptotic activity. In some embodiments of the aspects described herein, an N-terminal secretion signal sequence can be fused to the N-terminal of the extracellular domain of human TRAIL and/or of a MRTCT comprising a TRAIL domain. In some embodiments of the aspects described herein, the therapeutic TRAIL module can further comprise an isoleucine zipper domain.

In some embodiments, a TRAIL domain or variant thereof, can comprise an extracellular domain of human TRAIL. In some embodiments of the aspects described herein, the extracellular domain of human TRAIL comprises amino acids 39-281 of SEQ ID NO: 1. In some embodiments of the aspects described herein, the extracellular domain of human TRAIL comprises amino acids 95-281 of SEQ ID NO: 1. In some embodiments of the aspects described herein, the extracellular domain of human TRAIL comprises amino acids 114-281 of SEQ ID NO: 1. In some embodiments of the aspects described herein, the extracellular domain of human TRAIL comprises a sequence having at least 90% identity to amino acids 114-281 of SEQ ID NO: 1 and retains TRAIL apoptotic activity. In some embodiments of the aspects described herein, the extracellular domain of human TRAIL consists essentially of amino acids 114-281 of SEQ ID NO: 1. In some embodiments of the aspects described herein, the extracellular domain of human TRAIL consists of amino acids 114-281 of SEQ ID NO: 1.

Variants and derivatives of native TRAIL proteins for use in the therapeutic TRAIL modules that retain a desired biological activity of TRAIL, such as "TRAIL apoptotic activity" are also within the scope of the compositions and methods described herein. In some embodiments, the biological or apoptotic activity of a therapeutic TRAIL module is essentially equivalent to the biological activity of a native TRAIL protein. In some such embodiments, biological activity of a native TRAIL protein is TRAIL apoptotic activity. One measurement of TRAIL apoptotic activity by a TRAIL variant or TRAIL domain is the ability to induce apoptotic death of Jurkat cells. Assay procedures for identifying biological activity of TRAIL variants by detecting apoptosis of target cells, such as Jurkat cells, are well known in the art. DNA laddering is among the characteristics of cell death via apoptosis, and is recognized as one of the observable phenomena that distinguish apoptotic cell death from necrotic cell death. Apoptotic cells can also be identified using markers specific for apoptotic cells, such as Annexin V, in combination with flow cytometric techniques, as known to one of skill in the art.

TRAIL variants can be obtained by mutations of native TRAIL nucleotide sequences, for example. A "TRAIL variant," as referred to herein, is a polypeptide substantially homologous to a native TRAIL, but which has an amino acid sequence different from that of native TRAIL because of one or a plurality of deletions, insertions or substitutions. "TRAIL encoding DNA sequences" encompass sequences that comprise one or more additions, deletions, or substitutions of nucleotides when compared to a native TRAIL DNA sequence, but that encode a TRAIL protein or fragment thereof that is essentially biologically equivalent to a native TRAIL protein, i.e., has the same apoptosis inducing activity.

The variant amino acid or DNA sequence preferably is at least 70%, at least 75%, at least 80%, at least 85%, at least 90%, at least 91%, at least 92%, at least 93%, at least 94%, at least 95%, at least 96%, at least 97%, at least 98%, at least 99%, or more, identical to a native TRAIL sequence. The degree of homology or percent identity) between a native and a mutant sequence can be determined, for example, by comparing the two sequences using freely available computer programs commonly employed for this purpose on the world wide web.

Alterations of the native amino acid sequence can be accomplished by any of a number of known techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, Jan. 1985, 12-19); Smith et al. (Genetic Engineering: Principles and Methods, Plenum Press, 1981); and U.S. Pat. Nos. 4,518,584 and 4,737,462, which are herein incorporated by reference in their entireties.

TRAIL variants can, in some embodiments, comprise conservatively substituted sequences, meaning that one or more amino acid residues of a native TRAIL polypeptide are replaced by different residues, and that the conservatively substituted TRAIL polypeptide retains a desired biological activity, i.e., apoptosis inducing activity or TRAIL apoptotic activity, that is essentially equivalent to that of the native TRAIL polypeptide. Examples of conservative substitutions include substitution of amino acids that do not alter the secondary and/or tertiary structure of TRAIL.

In other embodiments, TRAIL variants can comprise substitution of amino acids that have not been evolutionarily conserved. Conserved amino acids located in the C-terminal portion of proteins in the TNF family, and believed to be important for biological activity, have been identified. These conserved sequences are discussed in Smith et al. (Cell, 73:1349, 1993, see page 1353 and FIG. 6); Suda et al. (Cell, 75:1169, 1993, see FIG. 7); Smith et al. (Cell, 76:959, 1994, see FIG. 3); and Goodwin et al. (Eur. J. Immunol., 23:2631, 1993, see FIG. 7 and pages 2638-39) hereby incorporated in their entireties by reference. Advantageously, in some embodiments, these conserved amino acids are not altered when generating conservatively substituted sequences. In some embodiments, if altered, amino acids found at equivalent positions in other members of the TNF family are substituted. Among the amino acids in the human TRAIL protein of SEQ ID NO:1 that are conserved are those at positions 124-125 (AH), 136 (L), 154 (W), 169 (L), 174 (L), 180 (G), 182 (Y), 187 (Q), 190 (F), 193 (Q), and 275-276 (FG) of SEQ ID NO:1. Another structural feature of TRAIL is a spacer region (i.e., TRAIL (39-94)) between the C-terminus of the transmembrane region and the portion of the extracellular domain that is believed to be important for biological apoptotic activity. In some embodiments, when the desired biological activity of TRAIL domain is the ability to bind to a receptor on target cells and induce apoptosis of the target cells substitution of amino acids occurs outside of the receptor-binding domain.

A given amino acid of a TRAIL domain can, in some embodiments, be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. TRAIL polypeptides comprising conservative amino acid substitutions can be tested in any one of the assays described herein to confirm that a desired TRAIL apoptotic activity of a native TRAIL molecule is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Be; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Particularly preferred conservative substitutions for use in the TRAIL variants described herein are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any cysteine residue not involved in maintaining the proper conformation of the MRTCT also can be substituted, generally with serine, to improve the oxidative stability of the molecule and prevent aberrant crosslinking. Conversely, cysteine bond(s) can be added to the MRTCT agent to improve its stability or facilitate oligomerization.

The MRTCTs described herein can further comprise, in some embodiments, a secretion signal sequence that permits a cell engineered to express a MRTCT to secrete the agent. As used herein, the terms "secretion signal sequence," "secretion sequence," "secretion signal peptide," or "signal sequence," refer to a sequence that is usually about 3-60 amino acids long and that directs the transport of a propeptide to the endoplasmic reticulum and through the secretory pathway during protein translation. As used herein, a signal sequence, which can also be known as a signal peptide, a leader sequence, a prepro sequence or a pre sequence, does not refer to a sequence that targets a protein to the nucleus or other organelles, such as mitochondria, chloroplasts and apicoplasts. In some embodiments of the MRTCTs described herein, a "secretion signal sequence" comprises 5 to 15 amino acids with hydrophobic side chains that are recognized by a cytosolic protein, SRP (Signal Recognition Particle), which stops translation and aids in the transport of an mRNA-ribosome complex to a translocon in the membrane of the endoplasmic reticulum. In some embodiments of the MRTCTs described herein, the signal peptide comprises at least three regions: an amino-terminal polar region (N region), where frequently positive charged amino acid residues are observed, a central hydrophobic region (H region) of 7-8 amino acid residues and a carboxy-terminal region (C region) that includes the cleavage site. Commonly, the signal peptide is cleaved from the mature protein with cleavage occurring at this cleavage site.

The secretory signal sequence can be operably linked to the sequence(s) encoding the at least two portions of the MRTCT as described herein, such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences can be positioned elsewhere in the nucleotide sequence of interest (see, e.g., Welch et al., U.S. Pat. No. 5,037,743; Holland et al., U.S. Pat. No. 5,143,830).

In some embodiments of the aspects described herein, the secretory sequence comprises amino acids 1-81 of the following Flt3L amino acid sequence: MTVLAPAWSP NSSLLLLLLL LSPCLRGTPD CYFSHSPISS NFKVK-FRELT DHLLKDYPVT VAVNLQDEKH CKALWSLFLA QRWIEQLKTV AGSKMQTLLE DVNTEIHFVT SCTFQ-PLPEC LRFVQTNISH LLKDTCTQLL ALKPCIGKAC QNFSRCLEVQ CQPDSSTLLP PRSPIALEAT ELPEP-RPRQL LLLLLLLLPL TLVLLAAAWG LRWQRARRRG ELHPGVPLPS HP (SEQ ID NO: 2, GenBank Accession P49772), or a fragment thereof. In some embodiments of the aspects described herein, the signal peptide comprises amino acids 1-81 of SEQ ID NO: 2. In some embodiments of the aspects described herein, the secretory signal sequence comprises a sequence having at least 90% identity to amino acids 1-81 of SEQ ID NO: 2. In some embodiments of the aspects described herein, the secretory signal sequence consists essentially of amino acids 1-81 of SEQ ID NO: 2. In some embodiments of the aspects described herein, the secretory signal sequence consists of amino acids 1-81 of SEQ ID NO: 2.

While the secretory signal sequence can be derived from Flt3L, in other embodiments a suitable signal sequence can also be derived from another secreted protein or synthesized de novo. Other secretory signal sequences which can be substituted for the Flt3L signal sequence for expression in eukaryotic cells include, for example, naturally-occurring or modified versions of the human IL-17RC signal sequence, otPA pre-pro signal sequence, human growth hormone signal sequence, human CD33 signal sequence Ecdysteroid Glucosyltransferase (EGT) signal sequence, honey bee Melittin (Invitrogen Corporation; Carlsbad, Calif.), baculovirus gp67 (PharMingen: San Diego, Calif.) (US Pub. No. 20110014656). Additional secretory sequences include secreted alkaline phosphatase signal sequence, interleukin-1 signal sequence, CD-14 signal sequence and variants thereof (US Pub. No. 20100305002) as well as the following peptides and derivatives thereof: Sandfly Yellow related protein signal peptide, silkworm friboin LC signal peptide, snake PLA2, *Cyrpidina noctiluca* luciferase signal peptide, and pinemoth fibroin LC signal peptide (US Pub. No. 20100240097). Further signal sequences can be selected from databases of protein domains, such as SPdb, a signal peptide database described in Choo et al., BMC Bioinformatics 2005, 6:249, LOCATE, a mammalian protein localization database described in Sprenger et al. Nuc Acids Res, 2008, 36:D230D233, or identified using computer modeling by those skilled in the art (Ladunga, Curr Opin Biotech 2000, 1:13-18).

Selection of appropriate signal sequences and optimization or engineering of signal sequences is known to those skilled in the art (Stern et al., Trends in Cell & Molecular Biology 2007 2:1-17; Barash et al., Biochem Biophys Res Comm 2002, 294:835-842). In some embodiments, signal sequences can be used that comprise a protease cleavage site for a site-specific protease (e.g., Factor IX or Enterokinase). This cleavage site can be included between the pro sequence and the bioactive secreted peptide sequence, e.g., MRTCT, and the pro-peptide can be activated by the treatment of cells with the site-specific protease (US Pub. No. 20100305002).

The MRTCTs described herein can, in some embodiments, further comprise a leucine zipper domain sequence. As used herein, "leucine zipper domains" refer to naturally occurring or synthetic peptides that promote oligomerization of the proteins in which they are found. The leucine zipper is a super-secondary structure that functions as a dimerization domain, and its presence generates adhesion forces in parallel alpha helices. A single leucine zipper comprises multiple leucine residues at approximately 7-residue intervals, which forms an amphipathic alpha helix with a hydrophobic region running along one side. The dimer formed by a zipper domain is stabilized by the heptan repeat, designated $(abcdefg)_n$ according to the notation of McLachlan and Stewart (J. Mol. Biol. 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix. The residues at position d (often leucine) contribute large hydrophobic stabilization energies, and are important for oligomer formation (Krystek et al., Int. J. Peptide Res. 38:229, 1991). This hydrophobic region provides an area for dimerization, allowing the motifs to "zip" together. Furthermore, the hydrophobic leucine region is absolutely required for DNA binding. Leucine zippers were originally identified in several DNA-binding proteins (Landschulz et al., Science 240: 1759, 1988), and have since been found in a variety of different proteins. Among the known leucine zippers are naturally occurring peptides and derivatives thereof that dimerize or trimerize.

Examples of zipper domains are those found in the yeast transcription factor GCN4 and a heat-stable DNA-binding protein found in rat liver (C/EBP; Landschulz et al., Science 243:1681, 1989). The nuclear transforming proteins, fos and jun, also exhibit zipper domains, as does the gene product of the murine proto-oncogene, c-myc (Landschulz et al., Science 240:1759, 1988). The fusogenic proteins of several different viruses, including paramyxovirus, coronavirus, measles virus and many retroviruses, also possess zipper domains (Buckland and Wild, Nature 338:547, 1989; Britton, Nature 353:394, 1991; Delwart and Mosialos, AIDS Research and Human Retrovirtises 6:703, 1990). The zipper domains in these fusogenic viral proteins are near the transmembrane region of the protein. Oligomerization of fusogenic viral proteins is involved in fusion pore formation (Spruce et al, Proc. Natl. Acad. Sci. U.S.A. 88:3523, 1991). Zipper domains have also been reported to play a role in oligomerization of heat-shock transcription factors (Rabindran et al., Science 259:230, 1993).

Examples of leucine zipper domains suitable for producing MRTCTs include, but are not limited to, those described in PCT application WO 94/10308; U.S. Pat. No. 5,716,805; the leucine zipper derived from lung surfactant protein D (SPD) described in Hoppe et al., 1994, FEBS Letters 344: 191; and Fanslow et al., 1994, Semin. Immunol. 6:267-278, the contents of each of which are hereby incorporated by reference in their entireties. In some embodiments of the MRTCTs, leucine residues in a leucine zipper domain are replaced by isoleucine residues. Such peptides comprising isoleucine can also be referred to as isoleucine zippers, but are encompassed by the term "leucine zippers" as used herein.

In some embodiments, an MRTCT can comprise a linker sequence between the first and second portions. In some embodiments, the linker sequence can comprise the 7 amino acids of SEQ ID NO: 3 (EASGGPE; SEQ ID NO: 3). In some embodiments, the linker sequence can comprise the 18 amino acids of SEQ ID NO: 4 (GSTGGSGKPGSGEGSTGG; SEQ ID NO: 4).

As used herein, a "linker module" refers to a peptide, or a nucleotide sequence encoding such a peptide, of at least 8 amino acids in length. In some embodiments of the aspects described herein, the linker module comprises at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 21 amino acids, at least 22 amino acids, at least 23 amino acids, at least 24 amino acids, at least 25 amino acids, at least 30 amino acids, at least 35 amino acids, at least 40 amino acids, at least 45 amino acids, at least 50 amino acids, at least 55 amino acids, at least 56 amino acids, at least 60 amino acids, or least 65 amino acids. In some embodiments of the aspects described herein, a linker module comprises a peptide of 18 amino acids in length. In some embodiments of the aspects described herein, a linker module comprises a peptide of at least 8 amino acids in length but less than or equal to 56 amino acids in length, i.e., the length of the spacer sequence in the native TRAIL molecule of SEQ ID NO: 1. In some embodiments, the linker molecule comprises the spacer sequence of human TRAIL, i.e., amino acids 39-94 of SEQ ID NO: 1, or a sequence having at least 80%, at least 85%, at least 90%, at least 95%, at least 99% identity to amino acids 39-94 of SEQ ID NO: 1. In some embodiments of the aspects described herein, a linker module comprises an amino acid sequence of SEQ ID NO: 4. In some embodiments of the aspects described herein, a linker module consists essentially of an amino acid sequence of SEQ ID NO: 4. In some embodiments of the aspects described herein, a linker module consists of an amino acid sequence of SEQ ID NO: 4. In some embodiments, the linker polypeptide is N-terminal to the second portion and C-terminal to the first portion.

In some embodiments, the first portion of an MRTCT is an antibody reagent which specifically binds to and inhibits EGFR and the second portion of an MRTCT is a TRAIL domain and/or variant. In some embodiments, the first portion of an MRTCT is a nanobody reagent which specifically binds to and inhibits EGFR and the second portion of an MRTCT is a TRAIL domain and/or variant. In some embodiments, the first portion of an MRTCT is an antibody reagent which specifically binds to and inhibits EGFR and the second portion of an MRTCT is S-TRAIL. In some embodiments, the first portion of an MRTCT is a nanobody reagent which specifically binds to and inhibits EGFR and the second portion of an MRTCT is S-TRAIL.

In one aspect, the technology described herein relates to a nucleic acid encoding an MRTCT as described herein.

Gene therapy or transgene compositions and methods thereof are also contemplated for use with the MRTCTs described herein. Such methods allow clinicians to introduce a nucleic acid sequence encoding an MRTCT or component thereof of interest directly into a patient (in vivo gene therapy) or into cells isolated from a patient or a donor (ex vivo gene therapy). Therapeutic MRTCTs produced by transduced cells after gene therapy can be maintained at a relatively constant level in, for example, the CNS of a subject, as compared to a protein that is administered directly. Such sustained production of a MRTCT is particularly appropriate in the treatment of chronic diseases, such as cancers. Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., Proc. Natl. Acad. Sci. USA (1995) 92:1292).

Further, regulatable genetic constructs using small molecule inducers have been developed that can be included in vectors to be used in some embodiments of the aspects described herein. (Rivera et al. (1996) Nat. Med. 2:1028-32; No et al. (1996) Proc. Natl. Acad. Sci. USA, 93:3346-51; Gossen and Bujard (1992) Proc. Natl. Acad. Sci. USA 89:5547-51; the GeneSwitch® system (Valentis, Inc., Burlingame, Calif.)). These systems are based on the use of engineered transcription factors the activity of which is controlled by a small molecule drug, and a transgene, the expression of which is driven by the regulated transcription factor (Rivera et al. (1996) Nat. Med. 2:1028-32; Pollock et al. (2000) Proc. Natl. Acad. Sci. USA 97:13221-26; U.S. Pat. Nos. 6,043,082 and 6,649,595; Rivera et al. (1999) Proc. Natl. Acad. Sci. USA 96:8657-62).

In some of the aspects described herein, a nucleic acid sequence encoding a MRTCT, or any module thereof, is operably linked to a vector. In general, as used herein, the term "vector" refers to any genetic element, such as a plasmid, phage, transposon, cosmid, chromosome, virus, virion, etc., that is capable of replication when associated with the proper control elements and that can transfer gene sequences to cells. Thus, the term includes cloning and expression vehicles, as well as viral vectors. By "recombinant vector" is meant a vector that includes a heterologous nucleic acid sequence, or "transgene" that is capable of expression in vivo. It should be understood that the vectors described herein can, in some embodiments, be combined with other suitable compositions and therapies. Vectors useful for the delivery of a sequence encoding a MRTCT or component thereof can include one or more regulatory elements (e.g., promoter, enhancer, etc.) sufficient for expression of the MRTCT or component thereof in the desired target cell or tissue. The regulatory elements can be chosen to provide either constitutive or regulated/inducible expression.

A nucleic acid sequence encoding a MRTCT or any module thereof, can, in some embodiments, be delivered using non-viral, plasmid-based nucleic acid delivery systems, as described in U.S. Pat. Nos. 6,413,942, 6,214,804, 5,580,859, 5,589,466, 5,763,270 and 5,693,622, all of which are incorporated herein by reference in their entireties. Such plasmids comprise the sequence encoding the MRTCT, or a component thereof, operably linked to control elements that direct the expression of the MRTCT in a target cell, and are well known to those of ordinary skill in the art.

In some embodiments, plasmid vectors comprising nucleic acid sequence(s) encoding a MRTCT or any module thereof can be packaged in liposomes prior to delivery to a subject or to cells, as described in U.S. Pat. Nos. 5,580,859, 5,549,127, 5,264,618, 5,703,055, all incorporated herein by reference in their entireties. For a review of the use of liposomes as carriers for delivery of nucleic acids, see, Hug and Sleight (1991) Biochim. Biophys. Acta. 1097:1-17; Straubinger et al. (1983) in Methods of Enzymology Vol. 101, pp. 512-27; de Lima et al. (2003) Current Medicinal Chemistry, Volume 10(14): 1221-31. The DNA can also be delivered in cochleate lipid compositions similar to those described by Papahadjpoulos et al. (1975) Biochem. Biophys. Acta. 394:483-491. See also U.S. Pat. Nos. 4,663,161 and 4,871,488, incorporated herein by reference in their entireties.

Biolistic delivery systems employing particulate carriers such as gold and tungsten can also be used to deliver nucleic acid sequence encoding a MRTCT, or any module thereof. See, e.g., U.S. Pat. Nos. 4,945,050, 5,036,006, 5,100,792, 5,179,022, 5,371,015, and 5,478,744, all incorporated herein by reference in their entireties.

A wide variety of other methods can be used to deliver the vectors comprising nucleic acid sequence(s) encoding a MRTCT or any module thereof. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, peptoid delivery, or microinjection. See, e.g., Sambrook et al (1989) Molecular Cloning, A Laboratory Manual, Cold Spring Harbor Laboratories, New York, for a discussion of techniques for transforming cells of interest; and Felgner, P.

L. (1990) Advanced Drug Delivery Reviews 5:163-87, for a review of delivery systems useful for gene transfer. Exemplary methods of delivering DNA using electroporation are described in U.S. Pat. Nos. 6,132,419; 6,451,002, 6,418,341, 6,233,483, U.S. Patent Publication No. 2002/0146831, and International Publication No. WO/0045823, all of which are incorporated herein by reference in their entireties.

In other embodiments of the aspects described herein, plasmid vectors comprising nucleic acid sequence(s) encoding a MRTCT or any module thereof can also be introduced directly into the CNS by intrathecal (IT) injection, as described herein in greater detail with regard to protein administration. Plasmid DNA can be complexed with cationic agents such as polyethyleneimine (PEI) or Lipofectamine 2000 to facilitate uptake.

Retroviruses, such as lentiviruses, provide another convenient platform for delivery of nucleic acid sequences encoding a MRTCT. A selected nucleic acid sequence can be inserted into a vector and packaged in retroviral particles using techniques known in the art. These retroviral vectors contain the components necessary for the correct packaging of the viral genome and integration into the host cell DNA. The recombinant virus can then be isolated and delivered to cells of the subject either in vivo or ex vivo. The nucleic acid sequences encoding a MRTCT or module thereof are cloned into one or more vectors, which facilitates delivery of the nucleic acid into a patient. Retroviral systems are described in, for example, U.S. Pat. No. 5,219,740; Miller and Rosman (1989) BioTechniques 7:980-90; Miller, A. D. (1990) Human Gene Therapy 1:5-14; Scarpa et al. (1991) Virology 180:849-52; Miller et al., Meth. Enzymol. 217:581-599 (1993); Burns et al. (1993) Proc. Natl. Acad. Sci. USA 90:8033-37; Boris-Lawrie and Temin (1993) Curr. Opin. Genet. Develop. 3:102-09. Greater detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy include: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993), the contents of each of which are herein incorporated by reference in their entireties.

In some embodiments of the aspects described herein, a lentiviral system is used to deliver a nucleic acid sequence encoding a MRTCT. Lentiviral vectors contemplated for use include, for example, the HIV based vectors described in U.S. Pat. Nos. 6,143,520; 5,665,557; and 5,981,276, the contents of which are herein incorporated by reference in their entireties.

In some embodiments, a nucleotide sequence encoding a MRTCT of interest or module thereof is inserted into an adenovirus-based expression vector. Unlike retroviruses, which integrate into the host genome, adenoviruses persist extrachromosomally thus minimizing the risks associated with insertional mutagenesis (Haj-Ahmad and Graham (1986) J. Virol. 57:267-74; Bett et al. (1993) J. Virol. 67:5911-21; Mittereder et al. (1994) Human Gene Therapy 5:717-29; Seth et al. (1994) J. Virol. 68:933-40; Barr et al. (1994) Gene Therapy 1:51-58; Berkner, K. L. (1988) BioTechniques 6:616-29; and Rich et al. (1993) Human Gene Therapy 4:461-76). Adenoviral vectors have several advantages in gene therapy. They infect a wide variety of cells, have a broad host-range, exhibit high efficiencies of infectivity, direct expression of heterologous sequences at high levels, and achieve long-term expression of those sequences in vivo. The virus is fully infective as a cell-free virion so injection of producer cell lines is not necessary. With regard to safety, adenovirus is not associated with severe human pathology, and the recombinant vectors derived from the virus can be rendered replication defective by deletions in the early-region 1 ("E1") of the viral genome. Adenovirus can also be produced in large quantities with relative ease. For all these reasons vectors derived from human adenoviruses, in which at least the E1 region has been deleted and replaced by a gene of interest, have been used extensively for gene therapy experiments in the pre-clinical and clinical phase.

Adenoviral vectors for use with the compositions and methods described herein can be derived from any of the various adenoviral serotypes, including, without limitation, any of the over 40 serotype strains of adenovirus, such as serotypes 2, 5, 12, 40, and 41. The adenoviral vectors used herein are replication-deficient and contain the sequence of interest under the control of a suitable promoter, such as any of the promoters discussed below with reference to adeno-associated virus. For example, U.S. Pat. No. 6,048,551, incorporated herein by reference in its entirety, describes replication-deficient adenoviral vectors that include a human gene under the control of the Rous Sarcoma Virus (RSV) promoter. Other recombinant adenoviruses of various serotypes, and comprising different promoter systems, can be created by those skilled in the art. See, e.g., U.S. Pat. No. 6,306,652, incorporated herein by reference in its entirety.

Other useful adenovirus-based vectors for delivery of nucleic acid sequence encoding a MRTCT of interest or module thereof include, but are not limited to: "minimal" adenovirus vectors as described in U.S. Pat. No. 6,306,652, which retain at least a portion of the viral genome required for encapsidation (the encapsidation signal), as well as at least one copy of at least a functional part or a derivative of the ITR; and the "gutless" (helper-dependent) adenovirus in which the vast majority of the viral genome has been removed and which produce essentially no viral proteins, thus allowing gene therapy to persist for over a year after a single administration (Wu et al. (2001) Anesthes. 94:1119-32; Parks (2000) Clin. Genet. 58:1-11; Tsai et al. (2000) Curr. Opin. Mol. Ther. 2:515-23).

In some embodiments of the compositions and methods described herein, a nucleotide sequence encoding a MRTCT is inserted into an adeno-associated virus-based expression vector. AAV is a parvovirus which belongs to the genus *Dependovirus* and has several features not found in other viruses. AAV can infect a wide range of host cells, including non-dividing cells. AAV can infect cells from different species. AAV has not been associated with any human or animal disease and does not appear to alter the biological properties of the host cell upon integration. Indeed, it is estimated that 80-85% of the human population has been exposed to the virus. Finally, AAV is stable at a wide range of physical and chemical conditions, facilitating production, storage and transportation.

AAV is a helper-dependent virus; that is, it requires co-infection with a helper virus (e.g., adenovirus, herpesvirus or vaccinia) in order to form AAV virions in the wild. In the absence of co-infection with a helper virus, AAV establishes a latent state in which the viral genome inserts into a host cell chromosome, but infectious virions are not produced. Subsequent infection by a helper virus rescues the integrated genome, allowing it to replicate and package its genome into infectious AAV virions. While AAV can infect cells from different species, the helper virus must be of the same species as the host cell. Thus, for example, human AAV will replicate in canine cells co-infected with a canine adenovirus.

Adeno-associated virus (AAV) has been used with success in gene therapy. AAV has been engineered to deliver genes of interest by deleting the internal nonrepeating portion of the AAV genome (i.e., the rep and cap genes) and inserting a heterologous sequence (in this case, the sequence encoding the MRTCT) between the ITRs. The heterologous sequence is typically functionally linked to a heterologous promoter (constitutive, cell-specific, or inducible) capable of driving expression in the patient's target cells under appropriate conditions.

Recombinant AAV virions comprising a nucleic acid sequence encoding a MRTCT can be produced using a variety of art-recognized techniques, as described in U.S. Pat. Nos. 5,139,941; 5,622,856; 5,139,941; 6,001,650; and 6,004,797, the contents of each of which are incorporated by reference herein in their entireties. Vectors and cell lines necessary for preparing helper virus-free rAAV stocks are commercially available as the AAV Helper-Free System (Catalog No. 240071) (Stratagene, La Jolla, Calif.).

Additional viral vectors useful for delivering nucleic acid molecules encoding a MRTCT include those derived from the pox family of viruses, including vaccinia virus and avian poxvirus. Alternatively, avipoxviruses, such as the fowlpox and canarypox viruses, can be used to deliver the genes. The use of avipox vectors in human and other mammalian species is advantageous with regard to safety because members of the avipox genus can only productively replicate in susceptible avian species. Methods for producing recombinant avipoxviruses are known in the art and employ genetic recombination, see, e.g., WO 91/12882; WO 89/03429; and WO 92/03545.

Molecular conjugate vectors, such as the adenovirus chimeric vectors, can also be used for delivery of sequence encoding a MRTCT or component thereof (Michael et al. (1993) J. Biol. Chem. 268:6866-69 and Wagner et al. (1992) Proc. Natl. Acad. Sci. USA 89:6099-6103). Members of the *Alphavirus* genus, for example the Sindbis and Semliki Forest viruses, can also be used as viral vectors for delivering a nucleic acid sequence encoding a MRTCT (See, e.g., Dubensky et al. (1996) J. Virol. 70:508-19; WO 95/07995; WO 96/17072).

In one aspect, the technology described herein relates to a cell comprising a vector comprising a nucleic acid encoding a MRTCT, a cell comprising a nucleic acid encoding a MRTCT, and/or a cell comprising a MRTCT. Essentially any cell type can be engineered with a sequence encoding a MRTCT, as described herein, for use in cellular therapies. Thus, differentiated somatic cells and stem cells, as well as cells of a cell line, can be engineered to express, using any method known to one of skill in the art, a desired MRTCT. In some embodiments of the aspects described herein, a cell can be transduced with a delivery vector comprising a nucleic acid sequence encoding a MRTCT or module thereof. In other embodiments of the compositions and methods described herein, a cell can be transfected with a nucleic acid sequence encoding a MRTCT. Provided herein are exemplary stem cells, somatic cells, and cell line sources useful with the methods and compositions described herein. However, the description herein is not meant to be limiting and any cell known or used in the art can be genetically modified or engineered to express and secrete a MRTCT. In some embodiments, the cells to be engineered can be from an autologous, i.e., from the same subject, or from one or more heterologous sources.

In some embodiment, the cell comprising a vector, nucleic acid, or MRTCT as described herein is a stem cell. Stem cells are undifferentiated cells defined by their ability at the single cell level to both self-renew and differentiate to produce progeny cells, including self-renewing progenitors, non-renewing progenitors, and terminally differentiated cells. Stem cells, depending on their level of differentiation, are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts. (See, e.g., Potten et al., Development 110: 1001 (1990); U.S. Pat. Nos. 5,750,376, 5,851,832, 5,753,506, 5,589,376, 5,824,489, 5,654,183, 5,693,482, 5,672,499, and 5,849,553, all herein incorporated in their entireties by reference).

One of the primary challenges to achieving effective anti-tumor therapies is highly efficient delivery of the anti-tumor agent specifically to the tumor, while minimizing toxicity to nonmalignant tissue. Although simple to administer, systemic administration of therapies can lead to accumulation of the toxic compounds at high levels in the liver and kidneys, resulting in dose-limiting renal- and hepatotoxicity (Kelley et al. J Pharmacol Exp Ther 2001, Lin, Drug Metab Dispos 1998). For example, TRAIL has been shown to have minimal cytotoxic effects on normal tissue; however, its short half-life and accumulation after systemic injection have been limitations to its potential use in clinics (Ashkenazi et al., J Clin Oncol 2008). Because of their potential to migrate to sites of disease and integrate into the cytoarchitecture of the brain, stem cells (e.g., neural stem cells, mesenchymal stem cells) have received much interest for the treatment of numerous neurologic disorders (Corsten and Shah, Lancet Oncology 2008, Singec et al. Annu Rev Med 2007). Previous studies from our lab and others demonstrated that neural stem cells (NSCs) and human mesenchymal stem cells (MNCs) migrate extensively throughout the murine brain and exhibit an inherent capacity to home to established gliomas (Sasportas et al. Proc Natl Acad Sci 2009, Shah et al Ann Neurol 2005, Shah et al. J Neurosci 2008, the contents of each of which are herein incorporated by reference in their entireties). Stem cells armed with S-TRAIL inhibited progression of gliomas in a xenogenic transplant model (Sasportas et al. Proc Natl Acad Sci 2009, Shah et al Ann Neurol 2005); however, assessing the pharmacokinetics of the molecules released by therapeutic NSC has been difficult.

The stem cells for use with the compositions and methods comprising MRTCTs described herein can be naturally occurring stem cells or "induced" stem cells, such as "induced pluripotent stem cells" (iPS cells) generated using any method or composition known to one of skill in the art. Stem cells can be obtained or generated from any mammalian species, e.g. human, primate, equine, bovine, porcine, canine, feline, rodent, e.g. mice, rats, hamster, etc. In some embodiments of the aspects described herein, a stem cell is a human stem cell.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and the cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Stem cells of interest for use in the compositions and methods described herein include embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci USA 92:7844); marmoset stem cells (Thomson et al. (1996) Biol. Reprod. 55:254); and human embryonic germ (hEG) cells (Shambloft et al., Proc. Natl. Acad. Sci. USA 95:13726, 1998). Cells derived from embryonic sources can include embryonic stem cells or stem cell lines obtained from a stem cell bank or other recognized depository institution.

In some embodiments of the aspects described herein, a cell engineered to express or secrete a MRTCT is an adult or somatic stem cell. Adult stem cells are generally limited to differentiating into different cell types of their tissue of origin. However, if the starting stem cells are derived from the inner cell mass of the embryo, they can generate many cell types of the body derived from all three embryonic cell types: endoderm, mesoderm and ectoderm. Stem cells with this property are said to be "pluripotent." Embryonic stem cells are one kind of pluripotent stem cell. Thus, pluripotent embryonic stem cells can be differentiated into many specific cell types. Since the embryo is a potential source of all types of precursor cells, it is possible to differentiate, for example, engineered embryonic stem cells into other lineages by providing the appropriate signals, such as the expression of proteins, using any method known to one of skill in the art, to embryonic stem cells.

Somatic or adult stem cells have major advantages, for example, as using somatic stem cells allows a patient's own cells to be expanded in culture and then re-introduced into the patient. Natural somatic stem cells have been isolated from a wide variety of adult tissues including blood, bone marrow, brain, olfactory epithelium, skin, pancreas, skeletal muscle, and cardiac muscle. Each of these somatic stem cells can be characterized based on gene expression, factor responsiveness, and morphology in culture. Exemplary naturally occurring somatic stem cells include, but are not limited to, neural stem cells, neural crest stem cells, mesenchymal stem cells, hematopoietic stem cells, and pancreatic stem cells. In addition, iPS cells generated from a patient provide a source of cells that can be engineered to express a MRTCT, expanded, and re-introduced to the patient, before or after stimulation to differentiate to a desired lineage or phenotype, such as a neural stem cell. In some embodiments of the aspects described herein, a somatic stem cell engineered to express a MRTCT is a neural stem cell. In some embodiments of the aspects described herein, a somatic stem cell engineered to express a MRTCT is a mesenchymal stem cell. In some embodiments of the aspects described herein, a somatic stem cell engineered to express a MRTCT is an iPS cell differentiated into a neural stem cell. In some embodiments of the aspects described herein, a somatic stem cell engineered to express a MRTCT is an iPS cell differentiated into a mesenchymal stem cell.

Cord blood cells are used as a source of transplantable stem and progenitor cells and as a source of marrow repopulating cells for the treatment of malignant diseases (e.g, acute lymphoid leukemia, acute myeloid leukemia, chronic myeloid leukemia, myelodysplastic syndrome, and neuroblastoma) and non-malignant diseases such as Fanconi's anemia and aplastic anemia (Kohli-Kumar et al., 1993 Br. J. Haematol. 85:419-422; Wagner et al., 1992 Blood 79; 1874-1881; Lu et al., 1996 Crit. Rev. Oncol. Hematol 22:61-78; Lu et al., 1995 Cell Transplantation 4:493-503). Accordingly, in some aspects, cells to be engineered to secrete or express a MRTCT can also be derived from human umbilical cord blood cells (HUCBC), which are recognized as a rich source of hematopoietic and mesenchymal stem cells (Broxmeyer et al., 1992 Proc. Natl. Acad. Sci. USA 89:4109-4113). One advantage of HUCBC for use with the methods and compositions described herein is the immature immunity of these cells, which is very similar to fetal cells, and thus significantly reduces the risk for rejection by the host (Taylor & Bryson, 1985 J. Immunol. 134:1493-1497).

In some embodiments of the aspects described herein, iPS cells are engineered to express or secrete the MRTCTs described herein. In some embodiments of the aspects described herein, iPS cells are engineered to express or secrete a MRTCT prior to being differentiated into another desired cell type. In some embodiments of the aspects described herein, iPS cells are engineered to express or secrete a MRTCT after differentiation into another desired cell type.

In other embodiments of the aspects described herein, cancer stem cells can be engineered to express or secrete a MRTCT described herein. It has been recently discovered that stem-like cells are present in some human tumors and, while representing a small minority of the total cellular mass of the tumor, are the subpopulation of tumor cells responsible for growth of the tumor. In contrast to normal stem cells, "tumor stem cells" or "cancer stem cells" are defined as cells that can undergo self-renewal, as well as abnormal proliferation and differentiation to form a tumor. Functional features of tumor stem cells are that they are tumorigenic; they can give rise to additional tumorigenic cells by self-renewal; and they can give rise to non-tumorigenic tumor cells. The developmental origin of tumor stem cells can vary among different types of cancers. It is believed, without wishing to be bound or limited by theory, that tumor stem cells can arise either as a result of genetic damage that deregulates normal mechanisms of proliferation and differentiation of stem cells (Lapidot et al., Nature 367(6464): 645-8 (1994)), or by the dysregulated proliferation of populations of cells that acquire stem-like properties.

Recent studies have shown that intracranially or intravenously injected neural stem cells (NSCs) or neural precursor cells migrate towards injured or pathological central nervous system (CNS) sites. This chemotropic property of NSCs has been utilized for cell-based therapies to treat diverse neurological diseases as described herein and in T. Bagci-Onder et al., Cancer Research 2011, 71:154-163; Hingtgen S. et al., Stem Cells 2010, 28(4):832-41; Hingtgen S. et al., Mol Cancer Ther. 2008, 7(11): 3575-85; Brustle O. et al., 6 Current Opinion in Neurobiology. 688 (1996); Flax J. D., et al., 16 Nature Biotechnology. 1033. (1998); Kim S. U., 24. Neuropathology. 159 (2004); Lindvall O et al., 10 (suppl) Nature Medicine. S42 (2004); Goldman S., 7. Nature Biotechnology. 862 (2005); Muller F. et al., 7 Nature Reviews Neuroscience. 75 (2006); Lee, J. P., et al. 13 Nature Medicine 439 (2007), and Kim S. U. et al., 87 Journal of Neuroscience Research 2183 (2009), the contents of each of which are herein incorporated in their entireties by reference.

Administration of delivery vectors can be performed intracranially or extracranially using known techniques. Stem cells, such as neural stem cells, have been shown to cross the blood-brain barrier and home towards injury in brain. Thus, for example stem cells engineered to produce the secreted MRTCTs described herein can be administered intravenously and are expected to reach desired areas of the brain, such as the site of a glioblastoma. Further, and importantly from a diagnostic aspect, as the MRTCTs comprise a reporter module, delivery of the cells and agents to a desired area can be visualized.

Accordingly, in some embodiments of the compositions and methods described herein, a pharmaceutically acceptable composition comprising a neural stem cell and a MRTCT can be administered to a subject. In some such embodiments, the neural stem cell is genetically engineered to express or secrete a MRTCT. Because NSCs can be engineered to package and release replication-defective retroviral particles or replication-conditional herpes virus vectors which, in turn, can serve as vectors for the transfer of sequences to CNS cells, neural progenitor/stem cells can serve to magnify the efficacy of viral-mediated gene delivery to large regions in the brain. In some such embodiments, the neural stem cell can comprise a vector encoding a MRTCT. Additional vectors that can be used in the embodiments described herein include herpes simplex virus vectors, SV 40 vectors, polyoma virus vectors, papilloma virus vectors, picarnovirus vectors, vaccinia virus vectors, and a helper-dependent or gutless adenovirus. In one embodiment, the vector can be a lentivirus. Methods for preparing genetically engineered neural stem cells and compositions thereof for therapeutic treatment have been described in U.S. Pat. Nos. 7,393,526 and 7,655,224, the contents of which are incorporated herein by reference in their entirety.

In various embodiments of the compositions and methods described herein, the neural stem cells that can be used include, but are not limited to, human neural stem cells, mouse neural stem cells HSN-1 cells, fetal pig cells and neural crest cells, bone marrow derived neural stem cells, and hNT cells. HSN-1 cells can be prepared, for example, as described in, e.g., Ronnett et al. (Science 248, 603-605, 1990). The preparation of neural crest cells in described in U.S. Pat. No. 5,654,183. hNT cells can be prepared as described in, e.g, Konubu et al. (Cell Transplant 7, 549-558, 1998). In some embodiments of the compositions and methods described herein, the neural stem cells that can be used are neural stem cells derived or differentiated from a precursor stem cell, such as a human embryonic stem cell or an induced pluripotent (iPS) cell. Such neural stem cells can be generated from or differentiated from human embryonic stem cells, using, for example, compositions and methods described in Nature Biotechnology 27, 275-280 (2009), "Highly efficient neural conversion of human ES and iPS cells by dual inhibition of SMAD signaling," the contents of which are herein incorporated by reference in their entireties. Such neural stem cells can be generated from or differentiated from iPS cells, using, for example, the compositions and methods described in US Patent Publication US 2010/0021437 A1, "NEURAL STEM CELLS DERIVED FROM INDUCED PLURIPOTENT STEM CELLS," the contents of which are herein incorporated by reference in their entireties.

Accordingly, as used herein, "neural stem cells" refers to a subset of pluripotent cells which have partially differentiated along a neural cell pathway and express some neural markers including, for example, nestin. Neural stem cells can differentiate into neurons or glial cells (e.g., astrocytes and oligodendrocytes). Thus, "neural stem cells derived or differentiated from iPS cells" refers to cells that are pluripotent but have partially differentiated along a neural cell pathway (i.e., express some neural cell markers), and themselves are the result of in vitro or in vivo differentiation iPS cells.

Neural selection factors that can be used to differentiate pluripotent stem cells, such as embryonic stem cells or iPS cells into neural stem cells, include, for example, sonic hedgehog (SHH), fibroblast growth factor-2 (FGF-2), and fibroblast growth factor-8 (FGF-8), which can be used alone or in pairwise combination, or all three factors may be used together. In some embodiments, iPS cells are cultured in the presence of at least SHH and FGF-8. In other embodiments, FGF-2 is omitted. Preferably, the neural stem cells derived from iPS cells express nestin. In some embodiments, the pluripotent stem cells are cultured in the presence of the one or more neural selection factors for 4, 5, 6, 7, 8, 9, 10, 12, 14, 16, 18, 20 days or more. Preferably, the population of neural stem cells is characterized in that at least 50%, at least 75%, at least 85%, at least 90%, at least 95%, or at least 99% of the cells of the population expresses nestin. Preferably, the nestin-expressing cells further express at least one of En-1, Pitx3, and Nurr-1. In other embodiments, the population of neural stem cells has been depleted of at least 50%, 75%, 85%, 95%, or 99% of the cells expressing surface markers of immature embryonic stem cells including, for example, SSEA-1, SSEA-3, SSEA-4, Tra-1-81, and Tra-1-60. Preferably, the population of neural stem cells contains less than 10%, less than 5%, less than 2.5%, less than 1%, or less than 0.1% of cells that express the selected marker (e.g., SSEA-4).

In some embodiments, the cells engineered to express or secrete a MRTCT described herein are primary somatic cells. Some non-limiting examples of primary cells include, but are not limited to, fibroblast, epithelial, endothelial, neuronal, adipose, cardiac, skeletal muscle, immune cells, hepatic, splenic, lung, circulating blood cells, gastrointestinal, renal, bone marrow, and pancreatic cells. The cell can be a primary cell isolated from any somatic tissue including, but not limited to, brain, liver, lung, gut, stomach, intestine, fat, muscle, uterus, skin, spleen, endocrine organ, bone, etc. The term "somatic cell" further encompasses primary cells grown in culture, provided that the somatic cells are not immortalized.

In some embodiments, the cells engineered to express or secrete a MRTCT as described herein described herein comprise cells of a cell line.

Exemplary human cell lines include, but are not limited to, 293T (embryonic kidney), BT-549 (breast), DMS 114 (small cell lung), DU145 (prostate), HT-1080 (fibrosarcoma), HEK 293 (embryonic kidney), HeLa (cervical carcinoma), HepG2 (hepatocellular carcinoma), HL-60 (TB) (leukemia), HS 578T (breast), HT-29 (colon adenocarcinoma), Jurkat (T lymphocyte), M14 (melanoma), MCF7 (mammary), MDA-MB-453 (mammary epithelial), PERC6® (E1-transformed embryonal retina), RXF 393 (renal), SF-268 (CNS), SF-295 (CNS), THP-1 (monocyte-derived macrophages), TK-10 (renal), U293 (kidney), UACC-257 (melanoma), and XF 498 (CNS).

Examples of non-human primate cell lines useful in the compositions and methods provided herein include, but are not limited to, monkey kidney (CVI-76) cells, African green monkey kidney (VERO-76) cells, green monkey fibroblast (Cos-1) cells, and monkey kidney (CVI) cells transformed by SV40 (Cos-7). Additional mammalian cell lines are known to those of ordinary skill in the art and are catalogued at the American Type Culture Collection catalog (ATCC®, Mamassas, Va.).

Examples of rodent cell lines useful in the compositions and methods provided herein include, but are not limited to, mouse Sertoli (TM4) cells, mouse mammary tumor (MMT) cells, rat hepatoma (HTC) cells, mouse myeloma (NS0) cells, murine hybridoma (Sp2/0) cells, mouse thymoma (EL4) cells, Chinese Hamster Ovary (CHO) cells and CHO cell derivatives, murine embryonic (NIH/3T3, 3T3 L1) cells, rat myocardial (H9c2) cells, mouse myoblast (C2C12) cells, and mouse kidney (miMCD-3) cells.

The compositions and methods comprising MRTCTs are particularly useful in patients in need of cellular therapies. Accordingly, various aspects and embodiments of the methods and compositions described herein involve administration of an effective amount of a cell or a population of cells, generated using any of the compositions comprising a MRTCT as described herein, or engineered to express a MRTCT as described herein, to an individual or subject in need of a cellular therapy. The cell or population of cells being administered can be an autologous population, or be derived from one or more heterologous sources. The cell can be, for example, a stem cell, such as a lineage-restricted progenitor cell, multipotent cell, or an oligopotent cell, or a fully or partially differentiated progeny of a stem cell. In some embodiments, cells engineered to secrete a MRTCT can be introduced via a scaffold or encapsulated in a biodegradable extracellular matrix to enhance retention and release of secreted MRTCTs in a subject in need thereof.

A variety of means for administering cells to subjects are known to those of skill in the art. Such methods can include systemic injection, for example, i.v. injection, or implantation of cells into a target site in a subject, such as a surgical site. Cells can be inserted into a delivery device which facilitates introduction by injection or implantation into the subject. Such delivery devices can include tubes, e.g., catheters, for injecting cells and fluids into the body of a recipient subject. In some embodiments, the tubes additionally have a needle, e.g., through which the cells can be introduced into the subject at a desired location. The cells can be prepared for delivery in a variety of different forms. For example, cells can be suspended in a solution or gel or embedded in a support matrix when contained in such a delivery device. Cells can be mixed with a pharmaceutically acceptable carrier or diluent in which the cells remain viable.

Pharmaceutically acceptable carriers and diluents include saline, aqueous buffer solutions, solvents and/or dispersion media. The use of such carriers and diluents is well known in the art. The solution is preferably sterile and fluid. Preferably, prior to the introduction of cells as described herein, the solution is stable under the conditions of manufacture and storage and preserved against the contaminating action of microorganisms such as bacteria and fungi through the use of agents such as parabens, chlorobutanol, phenol, ascorbic acid, thimerosal, and the like.

It is preferred that the mode of cell administration is relatively non-invasive, for example by intravenous injection, pulmonary delivery through inhalation, topical, or intranasal administration. However, the route of cell administration will depend on the tissue to be treated and can include implantation. Methods for cell delivery are known to those of skill in the art and can be extrapolated by one skilled in the art of medicine for use with the methods and compositions described herein.

In some embodiments of the methods described herein, a cell or population of cells engineered to express a MRTCT is directly placed or administered to a surgical site, such as a surgical resection site. By placing the cell or population of cells engineered to express a MRTCT at a surgical site, enhanced clearance of the target cancer cells can be achieved, as demonstrated herein. Such direct administration to a surgical site can include administration of a suspension of engineered cells, or encapsulation of engineered cells at the surgical site.

In some embodiments of the methods described herein, a cell or population of cells engineered to express a MRTCT are administered to a surgical site or lesion (e.g., cancer) site by intraparenchymal (e.g., intracerebral) grafting of the cell or cell populations into the surgical or lesioned region. The cells engineered to express a MRTCT can be delivered to a specific site by stereotaxic injection. Conventional techniques for grafting are described, for example, in Bjorklund et al. (Neural Grafting in the Mammalian CNS, eds. Elsevier, pp 169-178, 1985), Leksell et al. (Acta Neurochir., 52:1-7, 1980) and Leksedl et al. (J. Neurosturg., 66:626-629, 1987).

In some embodiments, administration of engineered cells into selected regions of a patient's brain can be made by drilling a hole and piercing the dura to permit the needle of a microsyringe to be inserted. Alternatively, in other embodiments, the cells can be injected into the brain ventricles or intrathecally into a spinal cord region.

Direct injection techniques for cell administration can also be used to stimulate transmigration of cells through the entire vasculature, or to the vasculature of a particular organ, such as for example liver, or kidney or any other organ. This includes non-specific targeting of the vasculature. One can target any organ by selecting a specific injection site, e.g., a liver portal vein. Alternatively, the injection can be performed systemically into any vein in the body. In another example, compositions comprising neural stem cells or precursor cells engineered to secrete a MRTCT can be transplanted directly into parenchymal or intrathecal sites of the central nervous system, according to the disease being treated, such as for example, the site of a glioblastoma. Grafts can be done using single cell suspensions or small aggregates at a density of 25,000-500,000 cells per mL (U.S. Pat. No. 5,968,829, the contents of which are herein incorporated in their entireties by reference).

If so desired, a mammal or subject can be pre-treated with an agent, for example an agent is administered to enhance cell targeting to a tissue (e.g., a homing factor) and can be placed at that site to encourage cells to target the desired tissue. For example, direct injection of homing factors into a tissue can be performed prior to systemic delivery of ligand-targeted cells.

It is further contemplated that, in some embodiments of these aspects, cells engineered to express the MRTCTs described herein, can not only be administered to a subject in need as cells in suspension, but also as cells populating a matrix, scaffold, or other support, to enhance retention of cells and delivery of the MRTCT at a site. Encapsulation of stem cells has shown to permit enhanced delivery of engineered stem cells, as described in, for example, Compte M. et al., Stem Cells 2009, 27(3):753-760, the contents of which are herein incorporated in their entireties by reference.

In some embodiments, a "support" refers to any suitable carrier material to which cells, such as engineered neural stem cells expressing a MRTCT described herein, are able to attach themselves or adhere, and can be used in order to form a corresponding cell composite, e.g. an artificial tissue. In some embodiments, a matrix or carrier material, respectively, is present already in a three-dimensional form desired for later application.

In some such embodiments, a matrix or a scaffold comprises a "biocompatible substrate" that can be used as a material that is suitable for implantation into a subject onto which a cell population can be deposited. A biocompatible substrate does not cause toxic or injurious effects once implanted in the subject. The biocompatible substrate can provide the supportive framework that allows cells to attach to it, and grow on it. Cultured populations of cells can then be grown on the biocompatible substrate, which provides the appropriate interstitial distances required for cell-cell interaction.

A matrix, structure, or scaffold can be used to aid in further controlling and directing a cell or population of cells expressing or secreting a MRTCT described herein. A matrix or scaffold can be designed or selected to provide environmental cues to control and direct the migration of cells to a site of injury or disease. A structure or scaffold can be engineered from a nanometer to micrometer to millimeter to macroscopic length, and can further comprise or be based on factors such as, but not limited to, material mechanical properties, material solubility, spatial patterning of bioactive compounds, spatial patterning of topological features, soluble bioactive compounds, mechanical perturbation (cyclical or static strain, stress, shear, etc. . . . ), electrical stimulation, and thermal perturbation.

A scaffold can be in any desired geometric conformation, for example, a flat sheet, a spiral, a cone, a v-like structure and the like. A scaffold can be shaped into, e.g., a heart valve, vessel (tubular), planar construct or any other suitable shape. Such scaffold constructs are known in the art (see, e.g., WO02/035992, U.S. Pat. Nos. 6,479,064, 6,461,628, the contents of which are herein incorporated in their entireties by reference). In some embodiments, after culturing the cells on the scaffold, the scaffold is removed (e.g., bioabsorbed or physically removed), and the cells maintain substantially the same conformation as the scaffold, such that, for example, if the scaffold was spiral shaped, the cells form a 3D-engineered tissue that is spiral shaped.

Biopolymer structures can be generated by providing a transitional polymer on a substrate; depositing a biopolymer on the transitional polymer; shaping the biopolymer into a structure having a selected pattern on the transitional polymer (poly(N-Isopropylacrylamide); and releasing the biopolymer from the transitional polymer with the biopolymer's structure and integrity intact. A biopolymer can be selected from a natural or synthetic extracellular matrix (ECM) protein, growth factor, lipid, fatty acid, steroid, sugar and other biologically active carbohydrates, a biologically derived homopolymer, nucleic acids, hormone, enzyme, pharmaceutical composition, cell surface ligand and receptor, cytoskeletal filament, motor protein, silks, polyprotein (e.g., poly(lysine)) or any combination thereof.

The biopolymers used in the generation of the matrices and scaffolds for the embodiments directed to cellular therapies using MRTCTs described herein include, but are not limited to, a) extracellular matrix proteins to direct cell adhesion and function (e.g., collagen, fibronectin, laminin, etc.); (b) growth factors to direct cell function specific to cell type (e.g., nerve growth factor, bone morphogenic proteins, vascular endothelial growth factor, etc.); (c) lipids, fatty acids and steroids (e.g., glycerides, non-glycerides, saturated and unsaturated fatty acids, cholesterol, corticosteroids, sex steroids, etc.); (d) sugars and other biologically active carbohydrates (e.g., monosaccharides, oligosaccharides, sucrose, glucose, glycogen, etc.); (e) combinations of carbohydrates, lipids and/or proteins, such as proteoglycans (protein cores with attached side chains of chondroitin sulfate, dermatan sulfate, heparin, heparan sulfate, and/or keratan sulfate); glycoproteins [e.g., selectins, immunoglobulins, hormones such as human chorionic gonadotropin, Alpha-fetoprotein and Erythropoietin (EPO), etc.]; proteolipids (e.g., N-myristoylated, palmitoylated and prenylated proteins); and glycolipids (e.g., glycoglycerolipids, glycosphingolipids, glycophosphatidylinositols, etc.); (f) biologically derived homopolymers, such as polylactic and polyglycolic acids and poly-L-lysine; (g) nucleic acids (e.g., DNA, RNA, etc.); (h) hormones (e.g., anabolic steroids, sex hormones, insulin, angiotensin, etc.); (i) enzymes (types: oxidoreductases, transferases, hydrolases, lyases, isomerases, ligases; examples: trypsin, collagenases, matrix metalloproteinases, etc.); (j) pharmaceuticals (e.g., beta blockers, vasodilators, vasoconstrictors, pain relievers, gene therapy, viral vectors, anti-inflammatories, etc.); (k) cell surface ligands and receptors (e.g., integrins, selectins, cadherins, etc.); (l) cytoskeletal filaments and/or motor proteins (e.g., intermediate filaments, microtubules, actin filaments, dynein, kinesin, myosin, etc.), or any combination thereof. For example, a biopolymer can be selected from the group consisting of fibronectin, vitronectin, laminin, collagen, fibrinogen, silk or silk fibroin.

In some embodiments of the compositions and methods described herein, cells engineered to express or secrete a MRTCT are encapsulated in an extracellular matrix comprising a thiol-modified hyaluronic acid and a thiol-reactive cross-linker, such as, for example, polyethylene glycol diacrylate.

In some embodiments of the compositions and methods described herein, cells engineered to express or secrete a MRTCT are encapsulated within permeable membranes prior to implantation. Several methods of cell encapsulation can be employed. In some embodiments, cells will be individually encapsulated. In other instances, many cells will be encapsulated within the same membrane. Several methods of cell encapsulation are well known in the art, such as described in European Patent Publication No. 301,777, or U.S. Pat. Nos. 4,353,888, 4,744,933, 4,749,620, 4,814,274, 5,084,350, and 5,089,272.

In one method of cell encapsulation, the isolated cells are mixed with sodium alginate and extruded into calcium chloride so as to form gel beads or droplets. The gel beads are incubated with a high molecular weight (e.g., MW 60-500 kDa) concentration (0.03-0.1% w/v) polyamino acid (e.g., poly-L-lysine) to form a membrane. The interior of the formed capsule is re-liquified using sodium citrate. This creates a single membrane around the cells that is highly permeable to relatively large molecules (MW about. 200-400 kDa), but retains the cells inside. The capsules are incubated in physiologically compatible carrier for several hours in order that the entrapped sodium alginate diffuses out and the capsules expand to an equilibrium state. The resulting alginate-depleted capsules is reacted with a low molecular weight polyamino acid which reduces the membrane permeability (MW cut-off 40-80 kDa).

Other exemplary materials suitable for use in matrices and scaffolds include, but are not limited to, PEG diacylate, hyaluronic acid, polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl chloride, polyvinyl fluoride, polyvinyl imidazole, chlorosulphonated polyolefins, polyethylene oxide, polyvinyl alcohol, Teflon, nylon silicon, and shape memory materials, such as poly(styrene-block-butadiene), polynorbonene, hydrogels, metallic alloys, and oligo(-caprolactone)diol as switching segment/oligo(p-dioxyanone)diol as physical crosslink. Other suitable polymers can be obtained by reference to The Polymer Handbook, 3rd edition (Wiley, N.Y., 1989), the contents of which are herein incorporated in their reference by entirety.

In some embodiments, additional bioactive substances can be added to a biopolymer matrix or scaffold comprising the cells engineered to express a MRTCT described herein, such as, but not limited to, demineralized bone powder as described in U.S. Pat. No. 5,073,373 the contents of which are incorporated herein by reference; collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as alkaline phosphatase, collagenase, peptidases, oxidases, etc.; polymer cell scaffolds with parenchymal cells; angiogenic agents and polymeric carriers containing such agents; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors or other means; tissue transplants; demineralized bone powder; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digestors; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids. The amounts of such optionally added bioactive substances can vary widely with optimum levels being readily determined in a specific case by routine experimentation.

The MRTCTs described herein can be administered directly as a pharmaceutical composition to a subject in need thereof by any appropriate route which results in an effective treatment in the subject. As used herein, the terms "administering," and "introducing" are used interchangeably and refer to the placement of a MRTCT into a subject by a method or route which results in at least partial localization of such agents at a desired site, such as a cancerous or tumor site or a tumor resection site, such that a desired effect(s) is produced.

In some embodiments of the methods described herein, the MRTCT is administered to a subject in need thereof by any mode of administration that delivers the agent systemically or to a desired surface or target, and can include, but is not limited to, injection, infusion, instillation, and inhalation administration. To the extent that polypeptide agents can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the MRTCT for use in the methods described herein are administered by intravenous infusion or injection.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the MRTCT other than directly into a target site, tissue, or organ, such as a tumor site, such that it enters the subject's circulatory system and, thus, is subject to metabolism and other like processes.

For the clinical use of the methods described herein, administration of the MRTCT can include formulation into pharmaceutical compositions or pharmaceutical formulations for parenteral administration, e.g., intravenous; mucosal, e.g., intranasal; ocular, or other mode of administration. In some embodiments of the methods, the MRTCTs described herein can be administered along with any pharmaceutically acceptable carrier compound, material, or composition which results in an effective treatment in the subject. Thus, a pharmaceutical formulation for use in the methods described herein can comprise a MRTCT as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, a MRTCT. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alcohols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

The MRTCTs described herein can be specially formulated for administration to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, a MRTCT can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960.

Some further embodiments of the formulations and modes of direct administration of the MRTCTs that can be used in the methods described herein are illustrated below.

Parenteral Dosage Forms.

Parenteral dosage forms can also be administered to a subject in need thereof, such as a cancer patient, by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms as described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Controlled and Delayed Release Dosage Forms.

In some embodiments of the aspects described herein, a MRTCT can be administered to a subject by controlled- or delayed-release means. Ideally, the use of an optimally designed controlled-release preparation in medical treatment is characterized by a minimum of drug/agent substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a MRTCT's onset of action, duration of action, plasma levels within the therapeutic window, and peak blood levels. In particular, controlled- or extended-release dosage forms or formulations can be used to ensure that the maximum effectiveness of a MRTCT is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the MRTCTs described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed agents and thus effect controlled delivery of the drug. Examples of specific anion exchangers include, but are not limited to, Duolite® A568 and Duolite® AP143 (Rohm&Haas, Spring House, Pa. USA).

In some embodiments, a MRTCT for use in the methods described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are preferred when the disorder occurs continuously in the subject, for example where the subject has a chronic disorder such as cancer. Each pulse dose can be reduced and the total amount of a MRTCT administered over the course of treatment to the patient is minimized.

The interval between pulses, when necessary, can be determined by one of ordinary skill in the art. Often, the interval between pulses can be calculated by administering another dose of a composition comprising a MRTCT when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Provided herein are methods to treat a subject having a malignant condition comprising administering an effective amount of a pharmaceutical composition comprising a MRTCT, a nucleic acid or vector encoding a MRTCT, and/or cells engineered to express or secrete a MRTCT. In some embodiments of these methods, the cells engineered to express or secrete a MRTCT are stem cells. In some such embodiments, the cells are neural stem cells. In some embodiments, the cells engineered to express or secrete a MRTCT are encapsulated in a matrix.

The terms "malignancy," "malignant condition," "cancer," or "tumor," as used herein, refer to an uncontrolled growth of cells which interferes with the normal functioning of the bodily organs and systems. A subject that has a malignancy (i.e., cancer or a tumor) is a subject having objectively measurable malignant or cancer cells present in the subject's body. Included in this definition are benign and malignant cancers, as well as dormant tumors or micrometastatses. Cancers which migrate from their original location and seed vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyo sarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments of the methods described herein, a subject having a malignant condition has a brain cancer, brain tumor, or intracranial neoplasm. Intracranial neoplasms or cancers can arise from any of the structures or cell types present in the CNS, including the brain, meninges, pituitary gland, skull, and even residual embryonic tissue. The overall annual incidence of primary brain tumors in the United States is 14 cases per 100,000. The most common primary brain tumors are meningiomas, representing 27% of all primary brain tumors, and glioblastomas, representing 23% of all primary brain tumors (whereas glioblastomas account for 40% of malignant brain tumor in adults). Many of these tumors are aggressive and of high grade. Primary brain tumors are the most common solid tumors in children and the second most frequent cause of cancer death after leukemia in children.

In some embodiments of the methods described herein, a subject having a malignant condition has a glioma or glioblastoma (GBM). Gliomas are brain tumors originating from glial cells in the nervous system. "Glial cells," commonly called neuroglia or simply glia, are non-neuronal cells that provide support and nutrition, maintain homeostasis, form myelin, and participate in signal transmission in the nervous system. The two most important subgroups of gliomas are astrocytomas and oligodendrogliomas. Belonging to the subgroup of astrocytomas, glioblastoma multiforme (referred to as glioblastoma hereinafter) is the most common malignant brain tumor in adults and accounts for approximately 40% of all malignant brain tumors and approximately 50% of gliomas. It aggressively invades the central nervous system and is ranked at the highest malignancy level (grade IV) among all gliomas. Although there has been steady progress in their treatment due to improvements in neuroimaging, microsurgery, diverse treatment options, such as temozolomide or radiation, glioblastomas remain incurable. The lethal rate of this brain tumor is very high: the average life expectancy is 9 to 12 months after first diagnosis. The 5-year survival rate during the observation period from 1986 to 1990 was 8.0%. To date, the five-year survival rate following aggressive therapy, including gross tumor resection, is still less than 10%.

Glioblastoma is the most common primary brain tumor in adults with a very poor prognosis. Treatment for GBM is maximal surgical tumor resection or "debulking" followed by radiation therapy, with concomitant and adjuvant chemotherapy. However, recurrence rates of GBM and the associated patient mortality are nearly 100%. Although resection of the primary tumor mass has shown clinical benefit, adjuvant chemotherapy has provided limited extra benefit. One of the main impediments to the efficient delivery of many therapeutic molecules is the blood brain barrier and vascular dysfunction in the tumor, which prevent many drugs from reaching brain tumor cells. Additionally, many drugs have short systemic half-lives and peak concentrations, which prevent drugs from ultimately reaching the brain and accumulating to therapeutic concentrations in individual brain tumor cells. Tumor cells of glioblastomas are the most undifferentiated ones among brain tumors, so the tumor cells have high potential of migration and proliferation and are highly invasive, leading to very poor prognosis. Glioblastomas lead to death due to rapid, aggressive, and infiltrative growth in the brain. The infiltrative growth pattern is responsible for the unresectable nature of these tumors. Glioblastomas are also relatively resistant to radiation and chemotherapy, and, therefore, post-treatment recurrence rates are high. In addition, the immune response to the neoplastic cells is rather ineffective in completely eradicating all neoplastic cells following resection and radiation therapy.

Glioblastoma is classified into primary glioblastoma (de novo) and secondary glioblastoma, depending on differences in the gene mechanism during malignant transformation of undifferentiated astrocytes or glial precursor cells. Secondary glioblastoma occurs in a younger population of up to 45 years of age. During 4 to 5 years, on average, secondary glioblastoma develops from lower-grade astrocytoma through undifferentiated astrocytoma. In contrast, primary glioblastoma predominantly occurs in an older population with a mean age of 55 years. Generally, primary glioblastoma occurs as fulminant glioblastoma characterized by tumor progression within 3 months from the start with no clinical or pathological abnormalities.

Glioblastoma migrates along myelinated nerves and spreads widely in the central nervous system. In most cases surgical treatment shows only limited sustainable therapeutic effect. Malignant glioma cells evade detection by the host's immune system by producing immunosuppressive agents that impair T cell proliferation and production of the immune-stimulating cytokine IL-2.

Accordingly, in some embodiments of the methods described herein, a subject having a malignant condition has or has had a glioblastoma. In some such embodiments, the composition comprising a MRTCT or cell engineered to express a MRTCT is administered to the subject during or following a surgical procedure, such as a gross tumor resection. In some such embodiments, the composition comprising a MRTCT or cell engineered to express a MRTCT is directly administered to a gross tumor resection site.

In some embodiments, the subject treated in accordance with the methods described herein is a subject in need of treatment for brain cancer, glioblastoma, lung cancer, breast cancer, and/or colon cancer. In some embodiments, the subject is administered a cell secreting an MRTCT wherein the cell is a type of stem cell that will home to the tissue in which the cancer is located, e.g. if the cancer is brain cancer, the stem call can be a neural stem cell or mesenchymal stem cell. In some embodiments, a cell secreting a MRTCT can be administered intravenously.

In some embodiments, the methods further comprise administering the pharmaceutical composition comprising a MRTCT, or cells engineered to express or secrete a MRTCT, to a subject having a malignant condition, such as a brain tumor (e.g., glioblastoma), along with one or more additional chemotherapeutic agents, biologics, drugs, or treatments as part of a combinatorial therapy. In some such embodiments, the chemotherapeutic agent biologic, drug, or treatment is selected from the group consisting of: radiation therapy, surgery, gemcitabine, cisplastin, paclitaxel, carboplatin, bortezomib, AMG479, vorinostat, rituximab, temozolomide, rapamycin, ABT-737, and PI-103. In some embodiments, the biologic can comprise a sequence encoding a microRNA or RNA-based inhibitor molecule, such as an inhibitor RNA or iRNA.

In some embodiments of the methods described herein, the methods further comprise administering one or more chemotherapeutics agent to the subject being administered the pharmaceutical composition comprising a MRTCT, or cells engineered to express or secrete a MRTCT. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. In addition, the methods of treatment can further include the use of radiation or radiation therapy. Further, the methods of treatment can further include the use of surgical treatments.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of the MRTCT or cells engineered to express or secrete a MRTCT described herein to a subject in order to alleviate a symptom of a cancer. As used herein, "alleviating a symptom of a cancer" is ameliorating any condition or symptom associated with the cancer. As compared with an equivalent untreated control, such reduction or degree of prevention is at least 5%, 10%, 20%, 40%, 50%, 60%, 80%, 90%, 95%, or 100% as measured by any standard technique.

The term "effective amount" as used herein refers to the amount of a MRTCT or cells engineered to express or secrete a MRTCT needed to alleviate at least one or more symptom of the disease or disorder, and relates to a sufficient amount of pharmacological composition to provide the desired effect. The term "therapeutically effective amount" therefore refers to an amount of a MRTCT or cells engineered to express or secrete a MRTCT using the methods as disclosed herein, that is sufficient to effect a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the MRTCT), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

As used herein, a "portion" refers to a part or fraction of a whole, e.g. a part or fraction of a total molecule. A particular molecule can have multiple portions, e.g. two portions, three portions, four portions, five portions, or more portions.

As used herein, "inhibiting or suppressing tumor growth" refers to reducing the rate of growth of a tumor, halting tumor growth completely, causing a regression in the size of an existing tumor, eradicating an existing tumor and/or preventing the occurrence of additional tumors upon administration of the MRTCT comprising compositions, or methods of the present invention. "Suppressing" tumor growth indicates a growth state that is curtailed when compared to growth without contact with a MRTCT of the present invention. Tumor cell growth can be assessed by any means known in the art, including, but not limited to, measuring tumor size, determining whether tumor cells are proliferating using a 3H-thymidine incorporation assay, or counting tumor cells. "Suppressing" tumor and/or malignant and/or cancerous cell growth means any or all of the following states: slowing, delaying, and stopping tumor growth, as well as tumor shrinkage. "Delaying development" of tumor and/or malignant and/or cancerous cells means to defer, hinder, slow, retard, stabilize, and/or postpone development of the disease. This delay can be of varying lengths of time, depending on the history of the disease and/or individual being treated.

As used herein, a "therapeutic molecule" is any polypeptide sequence which, when administered at an effective dose can inhibit tumor growth. In some embodiments, a therapeutic molecule can induce cell growth. In some embodiments, a therapeutic molecule can specifically bind to and activate DR4, DR5, and/or FasR. In some embodiments, a therapeutic molecule can specifically bind to and activate DR4 and/or DR5. In some embodiments a therapeutic molecule can be a TRAIL polypeptide and/or variant.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

As used herein, the terms "secretion signal sequence," "secretion sequence," "secretion signal peptide," or "signal sequence," refer to a sequence that is usually about 3-60 amino acids long and that directs the transport of a propeptide to the endoplasmic reticulum and through the secretory pathway during protein translation.

As used herein, a "leucine zipper domain" refers to a naturally occurring or synthetic peptide that promotes oligomerization of the proteins in which it is found.

The terms "stem cell" or "undifferentiated cell" as used herein, refer to a cell in an undifferentiated or partially differentiated state that has the property of self-renewal and has the developmental potential to differentiate into multiple cell types, without a specific implied meaning regarding developmental potential (i.e., totipotent, pluripotent, multipotent, etc.). A stem cell is capable of proliferation and giving rise to more such stem cells while maintaining its developmental potential. In theory, self-renewal can occur by either of two major mechanisms. Stem cells can divide asymmetrically, which is known as obligatory asymmetrical differentiation, with one daughter cell retaining the developmental potential of the parent stem cell and the other daughter cell expressing some distinct other specific function, phenotype and/or developmental potential from the parent cell. The daughter cells themselves can be induced to proliferate and produce progeny that subsequently differentiate into one or more mature cell types, while also retaining one or more cells with parental developmental potential. A differentiated cell may derive from a multipotent cell, which itself is derived from a multipotent cell, and so on. While each of these multipotent cells may be considered stem cells, the range of cell types each such stem cell can give rise to, i.e., their "developmental potential," can vary considerably. Alternatively, some of the stem cells in a population can divide symmetrically into two stem cells, known as stochastic differentiation, thus maintaining some stem cells in the population as a whole, while other cells in the population give rise to differentiated progeny only. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating. In some embodiments, the term stem cell refers generally to a naturally occurring parent cell whose descendants (progeny cells) specialize, often in different directions, by differentiation, e.g., by acquiring completely individual characters, as occurs in progressive diversification of embryonic cells and tissues. Some differentiated cells also have the capacity to give rise to cells of greater developmental potential. Such capacity may be natural or may be induced artificially upon treatment with various factors. Cells that begin as stem cells might proceed toward a differentiated phenotype, but then can be induced to "reverse" and re-express the stem cell phenotype, a term often referred to as "dedifferentiation" or "reprogramming" or "retrodifferentiation" by persons of ordinary skill in the art.

The term "somatic stem cell" is used herein to refer to any pluripotent or multipotent stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. Exemplary naturally occurring somatic stem cells include, but are not limited to, neural stem cells, neural crest stem cells, mesenchymal stem cells, hematopoietic stem cells, and pancreatic stem cells.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cell forming the body of an organism, as opposed to a germline cell.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene, and polypeptides obtained by translation of mRNA transcribed from a gene. In some embodiments, an expression product is transcribed from a sequence that does not encode a polypeptide, such as a microRNA.

The terms "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

The term "transduction" as used herein refers to the use of viral particles or viruses to introduce exogenous nucleic acids into a cell.

The term "transfection" as used herein refers the use of methods, such as chemical methods, to introduce exogenous nucleic acids, such as the nucleic acid sequences encoding the MRTCTs described herein, into a cell. As used herein, the term transfection does not encompass viral-based methods of introducing exogenous nucleic acids into a cell. Methods of transfection include physical treatments (electroporation, nanoparticles, magnetofection), and chemical-based transfection methods. Chemical-based transfection methods include, but are not limited to, cyclodextrin, polymers, liposomes, nanoparticles, cationic lipids or mixtures thereof (e.g., DOPA, Lipofectamine and UptiFectin), and cationic polymers, such as DEAE-dextran or polyethylenimine.

The term "anti-cancer therapy" refers to a therapy useful in treating a malignancy or cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., Herceptin®), anti-CD20 antibodies, an epidermal growth factor receptor (EGFR) antagonist (e.g., a tyrosine kinase inhibitor), HER1/EGFR inhibitor (e.g., erlotinib (Tarceva®)), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins, such as small molecule toxins or enzymatically active toxins of bacterial, fungal, plant or animal origin, including fragments and/or variants thereof.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2.sup.nd ed., .COPYRGT. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The MRTCTs described herein can be used in conjunction with additional chemotherapeutic agents.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a malignant condition or cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s) of a malignant disease, diminishment of extent of a malignant disease, stabilized (i.e., not worsening) state of a malignant disease, delay or slowing of progression of a malignant disease, amelioration or palliation of the malignant disease state, and remission (whether partial or total), whether detectable or undetectable. The term "treatment" of a disease also includes providing relief from the symptoms or side-effects of the disease (including palliative treatment).

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A multifunctional receptor targeted cancer therapeutic comprising two portions capable of binding specifically to receptors on cancer cells and targeting a broad spectrum of tumors that are resistant to either portion.
2. A multifunctional receptor targeted cancer therapeutic comprising a first portion capable of specific binding with a cancer cell receptor and a second portion comprising a therapeutic molecule.
3. The composition of any of paragraphs 1-2, wherein the first portion comprises an antibody reagent.
4. The composition of any of paragraphs 1-3, wherein the antibody reagent is a nanobody reagent.
5. The composition of any of paragraphs 1-2, wherein the first portion comprises a ligand or ligand mimetic.
6. The composition of any of paragraphs 1-5, wherein the cancer cell receptor is EGFR
7. The composition of paragraph 6, wherein the first portion inhibits EGFR signaling.
8. The composition of any of paragraphs 1-7, wherein the second portion is capable of binding specifically with a second cancer cell receptor.
9. The composition of paragraph 8, wherein the second cancer cell receptor is DR4 or DR5.
10. The composition of any of paragraphs 8-9, wherein the binding of the second portion activates apoptosis.
11. The composition of any of paragraphs 1-10, wherein the therapeutic molecule is selected from the group consisting of:
    TRAIL; an extracellular domain of human TRAIL; S-TRAIL;
12. The composition of paragraph 11 wherein the extracellular domain of human TRAIL comprises amino acids 114-281 of SEQ ID NO: 1.
13. The composition of any of paragraphs 1-12, wherein the first and second portions are joined by a linker polypeptide sequence.
14. The composition of paragraph 1-13, wherein the linker polypeptide is N-terminal to the second portion and C-terminal to the first portion.
15. The composition of any of paragraphs 1-14, wherein the linker polypeptide sequence comprises at least 8 amino acids.
16. The composition of any of paragraphs 13-15, wherein the linker polypeptide comprises the amino acid sequence of SEQ ID NO: 4.
17. The composition of any of paragraphs 1-16, wherein the multifunctional receptor targeted cancer therapeutic further comprises a signal sequence.
18. The composition of any of paragraphs 1-17, wherein the multifunctional receptor targeted cancer therapeutic further comprises an isoleucine zipper domain.
19. A nucleic acid molecule encoding the multifunctional receptor targeted cancer therapeutic of any of paragraphs 1-18.
20. A vector comprising the nucleic acid molecule of paragraph 19.
21. The vector of paragraph 20, wherein the vector is a lentiviral or adenoviral vector.
22. A cell comprising the vector of paragraphs 20-21, the nucleic acid molecule of paragraph 19, or the multifunctional receptor targeted cancer therapeutic of any of paragraphs 1-18.
23. The cell of paragraph 22, wherein the cell is a stem cell.
24. The cell of paragraph 23, wherein the stem cell is a neural stem cell or a mesenchymal stem cell.
25. The cell of any of paragraphs 22-24, wherein the multifunctional receptor targeted cancer therapeutic is secreted by the cell.
26. The cell of any one of paragraphs 22-25, wherein the cell is encapsulated in a matrix or scaffold.
27. The cell of paragraph 26, wherein the matrix comprises a synthetic extracellular matrix.

28. The cell of any one of paragraphs 26-27, wherein the matrix is biodegradable.
29. The cell of any one of paragraphs 26-28, wherein the synthetic extracellular matrix comprises a thiol-modified hyaluronic acid and a thiol reactive cross-linker molecule.
30. The cell of paragraph 29, wherein the thiol reactive cross-linker molecule is polyethylene glycol diacrylate.
31. A pharmaceutical composition comprising the cell of any of paragraphs 22-30, the vector of any of paragraphs 20-21, the nucleic acid molecule of paragraph 19, or the multifunctional receptor targeted cancer therapeutic of any of paragraphs 1-18 and optionally, a pharmaceutically acceptable carrier.
32. A method comprising administering a therapeutically effective amount of a composition of any of paragraphs 1-31 to a subject in need of treatment for cancer.
33. The method of paragraph 32, wherein the subject is in need of treatment for brain cancer, glioblastoma, lung cancer, breast cancer, and colon cancer.
34. The method of any of paragraphs 32-33, wherein the stem cell is a type that will home to the tissue in which the cancer is located.
35. The method of paragraph 34, wherein the cancer is brain cancer and the stem cell is a neural stem cell or mesenchymal stem cell.
36. The method of any of paragraphs 32-25, wherein the composition is administered intravenously.
37. The use of the pharmaceutical composition of paragraph 31, the cell of any of paragraphs 22-30, the vector of any of paragraphs 20-21, the nucleic acid molecule of paragraph 19, or the multifunctional receptor targeted cancer therapeutic of any of paragraphs 1-18 for the treatment of cancer.

EXAMPLES

Example 1

Receptor Targeted Multifunctional Immuno-Conjugates as Therapeutics for Broad Spectrum of Tumors Receptor targeted cancer therapeutics (RCT) have been widely used in cancer research. RCT selectively bind to receptors expressed specifically on tumor cells and either arrest the growth of cells or induce cell death. Described herein are multifunctional immuno-conjugates of RCT (MRCT), ENb-TRAIL that target multiple receptor types specifically on tumor cells thus killing a broad spectrum of tumor cell types in vitro and in different mouse tumor models. The ability of ENb-TRAIL to target multiple receptor mediated signalling pathways that control tumor cell proliferation and death in diverse conditions and with diverse delivery modalities relates to cancer treatment as described herein. The invention therefore relates to a new class of therapeutics, MRCT's, and methods of using them in cancer therapy.

Deregulation of EGFR is Common in Variety Types of Tumor.

The binding of ligands to the epidermal growth factor receptor (EGFR), a transmembrane glycoprotein, leads to activation of the EGFR tyrosine kinase and subsequent stimulation of signal transduction pathways that are involved in regulating cell proliferation, differentiation, migration and survival (1). Although present in normal cells, EGFR is overexpressed and mutated in a variety of tumors and has been associated with poor prognosis and decreased survival (2). Although EGFR is well-accepted cancer therapy target, current agents used to inhibit EGFR signaling including small-molecule receptor tyrosine kinase inhibitors (smRTKI), like Gefinitib (Iressa, ZD1839) and Erlotinib (Tarceva, OSI-774) have had moderate success in clinical trials in different tumor types, and monoclonal antibodies (mAb), such as Cetuximab (Erbitux, Mab-C225), Panitumumab (ABX-EGF) and Matuzumab (EMD72000) had limited to no success in cancer patients (3). There is a need for MRCT that comprise different receptor targeted molecules and simultaneously target tumor cell proliferation and induce tumor cell specific cell death. MRCT must offer a well-defined mechanism of action/molecular target. Over the past two decades, much effort has been directed at developing anticancer agents that can interfere with EGFR activity and arrest tumor growth and, in some cases, cause tumor regression. Recently, antibody-based anti-cancer therapies that involve smaller antibody fragments such as Fabs, ScFvs and nanobodies (Nbs) have been emerging (4). Nbs are derived from heavy chain-only antibodies found in camelids (e.g. *llama*), and consist solely of the antigen-specific domain (VHH). Nbs are significantly smaller in size (15 kDa) than scFv (28 kDa) or Fab (55 kDa), thereby potentially providing higher tissue dispersion than their counterparts (4). In addition, Nbs are significantly more stable than $V_H$ domains and have improved penetration against immune-evasive (cryptic) antigens compared to mAbs (5, 6). Recently, *Llama glama*-derived EGFR-specific nanobodies (ENb) have been described (7, 8).

TRAIL can selectively induce apoptosis in tumor cells, both in culture and in vivo, while sparing most normal cells. TRAIL induces apoptosis by binding to death domain-containing receptors, (DR)-4 and -5, on the cell surface, thereby initiating a cascade of signaling events leading to activation of caspases. A secretable version of TRAIL (S-TRAIL) is efficiently secreted into the producer cell's immediate microenvironment and exhibits higher cytotoxicity on tumor cells than the native TRAIL protein (11-13).

Considerations in the Design of MRCT's.

One aspect of the invention is a multifunctional immuno-conjugate having the general structure: ENb-linker-TRAIL. The design of an MRCT begins, e.g. with a consideration of enhancing current EGFR based cancer target therapy sensitivity and specificity upon which its properties are based. MRCT is a fusion protein consisting of cDNA fusions encoding bivalent and bispecific Nbs against cancer specific surface antigen, e.g. EGFR and a potent cytotoxic variant of TRAIL. MRCT's can be considered to consist of three general parts: (i) a selective surface antigen bivalent Nanobody, (ii) linker, and (iii) soluble TRAIL domain (diagrammed in FIG. 1.). The ENb typically bind to cancer selective surface antigen (e.g. EGFR), which attenuates cancer cell addicted signalling pathways; In addition to playing a role in sensitizing cancer cells to TRAIL, more importantly ENb binding membrane antigen assists in making soluble TRAIL membrane bound, therefore to activate not only TRAIL receptor DR4, but also DR5 which is only activated by membrane-bound TRAIL (16). The linker gives rise to physiological flexibility of individual protein domain among fusion protein. Thus MRCT's are complex structures with each component playing a role in their properties in biological systems (secretable, cancer cell targeting, sensitizing, membrane binding and apoptosis inducing).

ENb-TRAIL Induces Apoptosis Specifically in Tumor Cells.

Figures 2A, 2B, 2C, 2D:
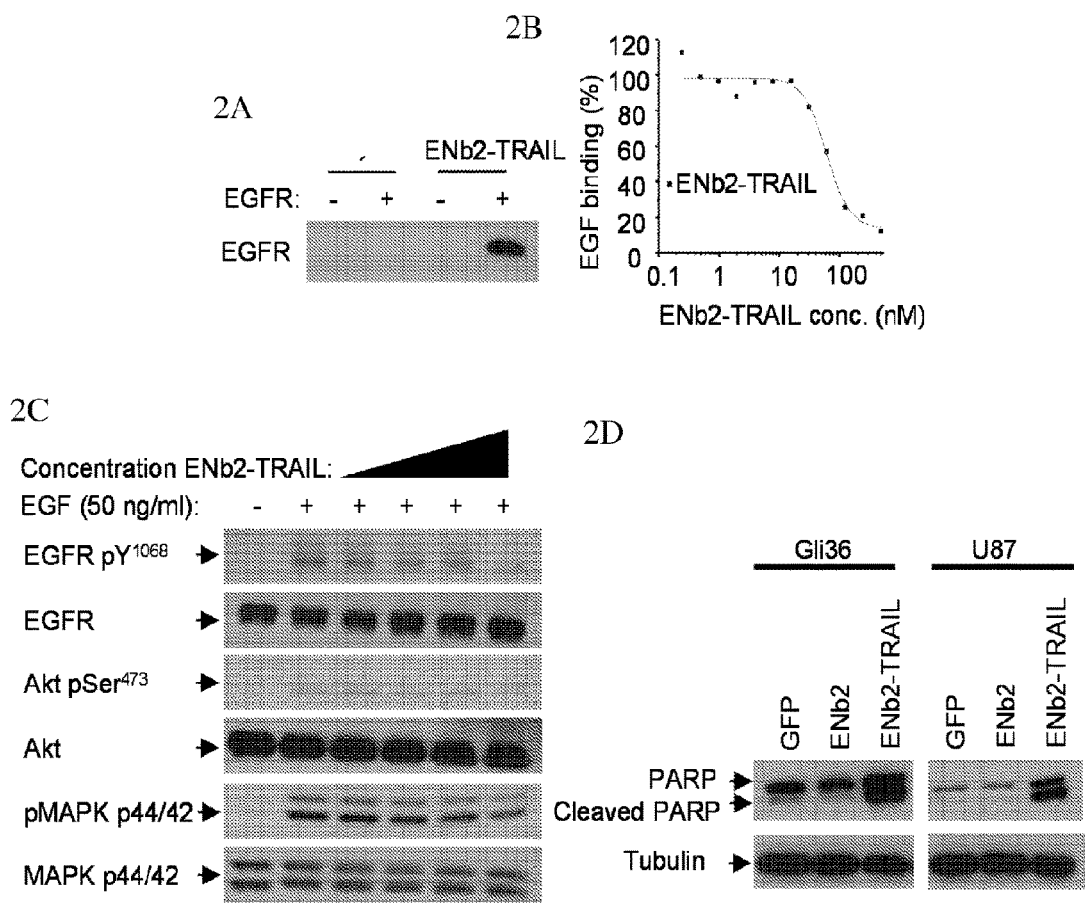
FIGS. 2A-2D demonstrate that Enb-TRAIL induces apoptosis of cancer cells.

The design of MRCT must preserve the essential features of the ENb and TRAIL upon which it is based. The verification that a putative MRCT has the properties of the ENb and TRAIL upon which it was based is shown in FIGS. 2A-2D. HEK-293T transduced with a lentiviral vector engineered with ENb-TRAIL (LV-ENb2-TRAIL) efficiently secreted ENb2-TRAIL (200 ng/mL per $10^6$ cells) and when tested on Her14 (EGFR+) and NIH-3T3 (EGFR−) cell lines, ENb2-TRAIL was shown to specifically bind to EGFR (FIG. 2A) and compete with EGF ligand binding to EGFR (FIG. 2B). This resulted in the subsequent inhibition of EGFR signaling in Her14 (FIG. 2C). ENb2-TRAIL was also shown to induce apoptosis in Gli36 and U87 GBM cells (FIG. 2D).

ENb-TRAIL Induces Apoptosis Through Binding EGFR and Enables S-TRAIL to Activate Both DR4 and DR5.

Figures 3A, 3B:
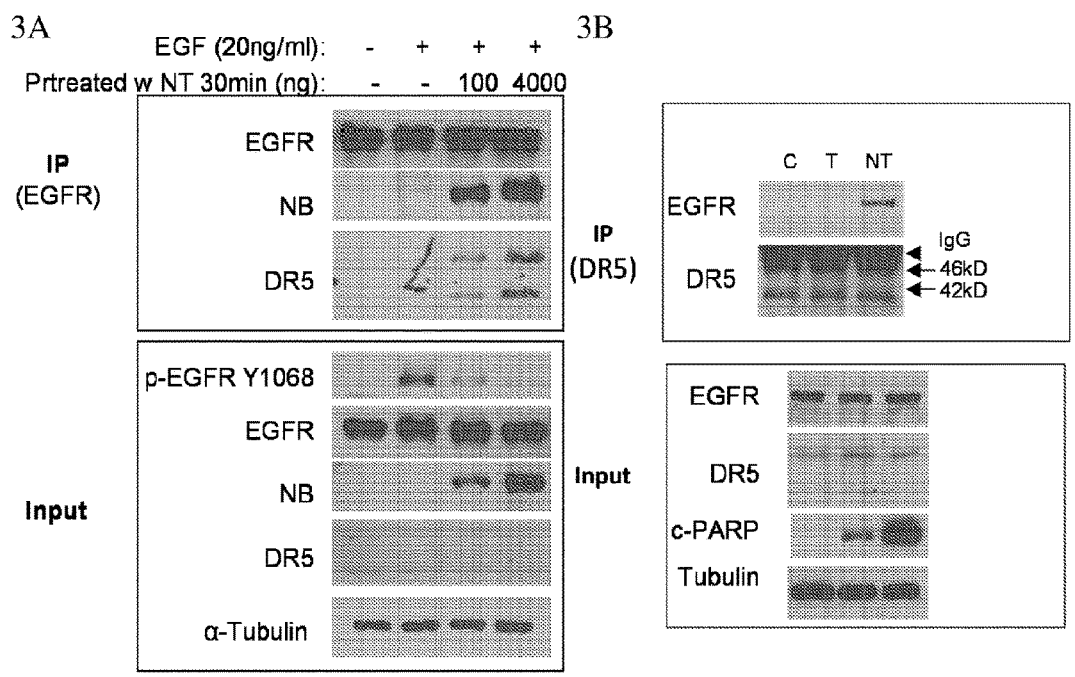
FIGS. 3A-3B demonstrate that ENb-TRAIL interacts with EGFR and DR5.

Previous studies have shown differential activation of DR4 and DR5 by soluble and membrane TRAIL (16). DR4 responds to soluble and membrane TRAIL equally, whereas DR5 signals only in response to membrane TRAIL. To verify that ENb-TRAIL induced apoptosis is via the interaction with EGFR and TRAIL receptors, co-immunoprecipitation results showed that ENb-TRAIL binds to both EGFR and DR5 (FIG. 3A). To confirm that ENb-TRAIL activates both DR4 and DR5, cells were treated with ENb-TRAIL and immunoprecipitated with DR4 and DR5 antibodies. These results demonstrated that ENb-TRAIL binds and activates at least DR5 (FIG. 3B).

ENb-TRAIL Improves S-TRAIL Efficacy Through Attenuating EGFR/PI3K/AKT/mTOR Pathways.

Figure 4A:
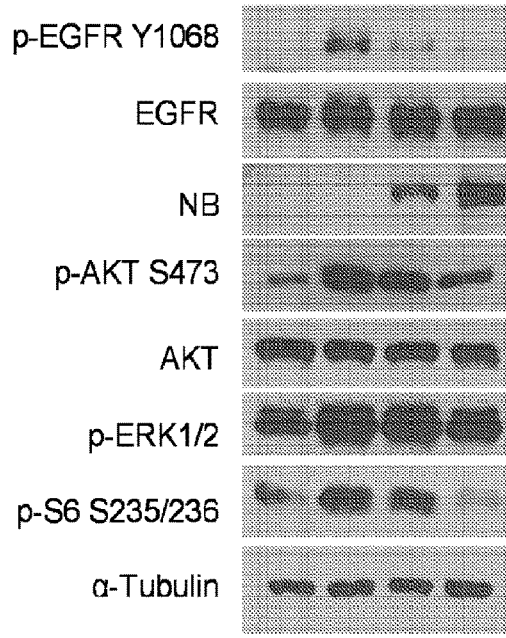
FIGS. 4A-4B demonstrate that Enb-TRAIL attenuates EGF activation of EGFR signaling.
Figure 4B:
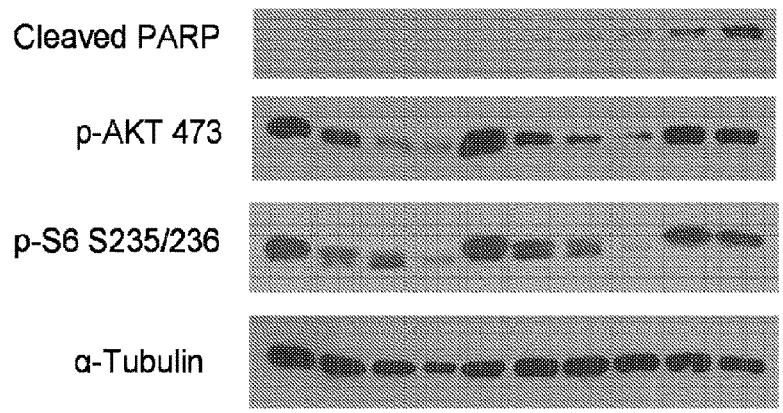

It is known that PI3K/AKT/mTOR and its downstream target involved in regulating TRAIL sensitivity (17, 18). To verify that ENb-TRAIL also employs its EGFR nanobody function to suppress EGFR/PI3K/AKT/mTOR pathway and therefore sensitize TRAIL-induced apoptosis, a TRAIL resistant tumor cell line LN229 was tested. The results indicate that ENb-TRAIL attenuates EGF stimulation of EGFR pathway (FIG. 4A). Furthermore, it was confirmed that inhibition of EGFR/PI3K/AKT/mTOR signalling with PI3K/mTOR dual inhibitor sensitizes TRAIL-induced apoptosis (FIG. 4B).

ENb-TRAIL can be Administrated Systematically or Delivered by Stem Cells as a Secreted Protein.

Figure 5A:
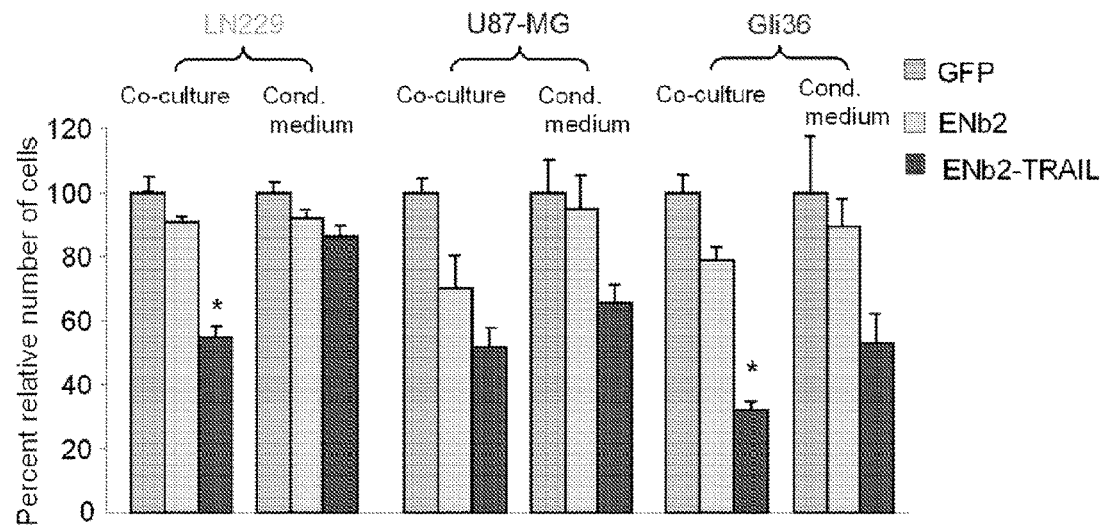
FIGS. 5A-5B demonstrate in vitro efficacy of stem cell released ENb-TRAIL.
Figure 5B:
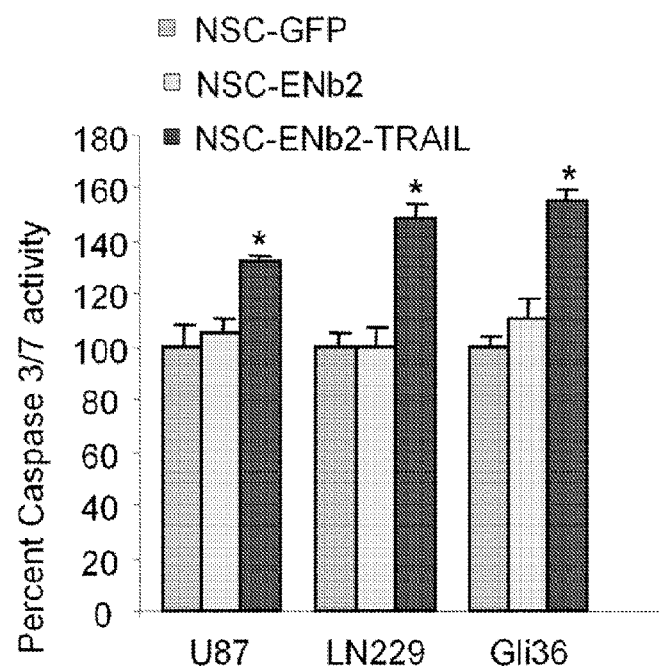

Purified ENb-TRAIL fusion protein can be administrated intravenously as systematic delivery for most types of tumors. For certain type of tumor, such as brain tumor, a big challenge for efficient delivery of therapeutic molecules is the blood brain barrier and vascular dysfunction in the tumor. One of the solutions to the problem of delivering drug to intracranial tumors is on-site delivery by stem cells (SC). To explore the effect of SC released ENb2-TRAIL on tumor cell proliferation and death, neural SC (NSC) were engineered to express ENb2-TRAIL and co-cultured with glioblastoma multiforme (GBM) cells expressing a fusion of fluorescent and bioluminescent protein (mCherry-Fluc) with NSC-ENb2-TRAIL, NSC-ENb2 and control NSC-GFP. NSC-ENb2-TRAIL treatment resulted in reduced viability of all GBM cells Gli36, U87-MG and LN229 (5A). Furthermore, NSC-ENb2-TRAIL treatment had a profound effect on GBM cell viability and resulted in TRAIL-mediated apoptosis as indicated by caspase-3/7 upregulation in the three cell lines (FIG. 5B).

ENb-TRAIL can Target Variety of Tumor Types with Known Deregulation of EGFR.

Figure 6:
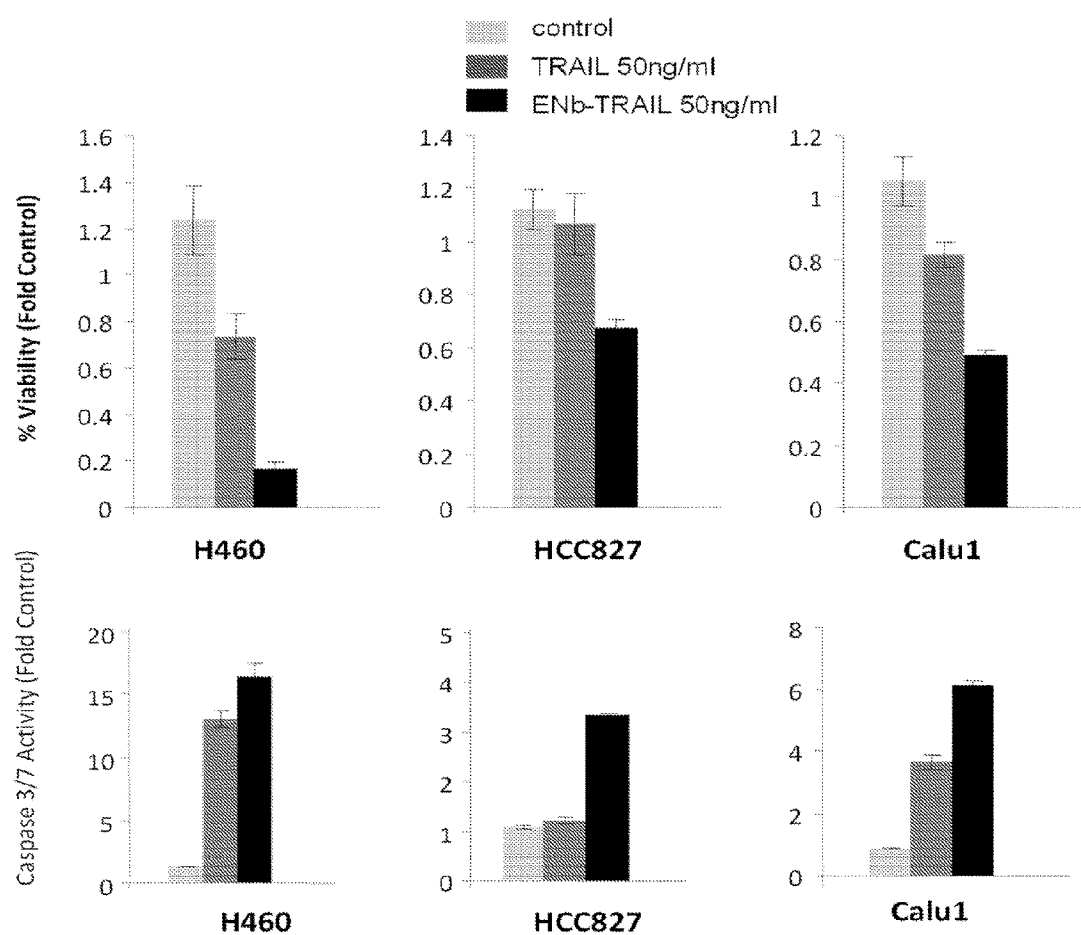
FIG. 6 depicts graphs of cell death and caspase activity in different human lung cancer lines incubated with TRAIL or ENb-TRAIL. Cell viability and caspase 3/7 activities were determined 24 hour post incubation. Mean+/−SD.

FIG. 6 demonstrates that data on lung cancer lines show that ENb-TRAIL induces cell death in all the lung cancer lines tested.

NSC-Delivered ENb-TRAIL Significantly Influences GBMs In Vivo.

Figures 7A, 7B, 7C, 7D, 7E, 7F:
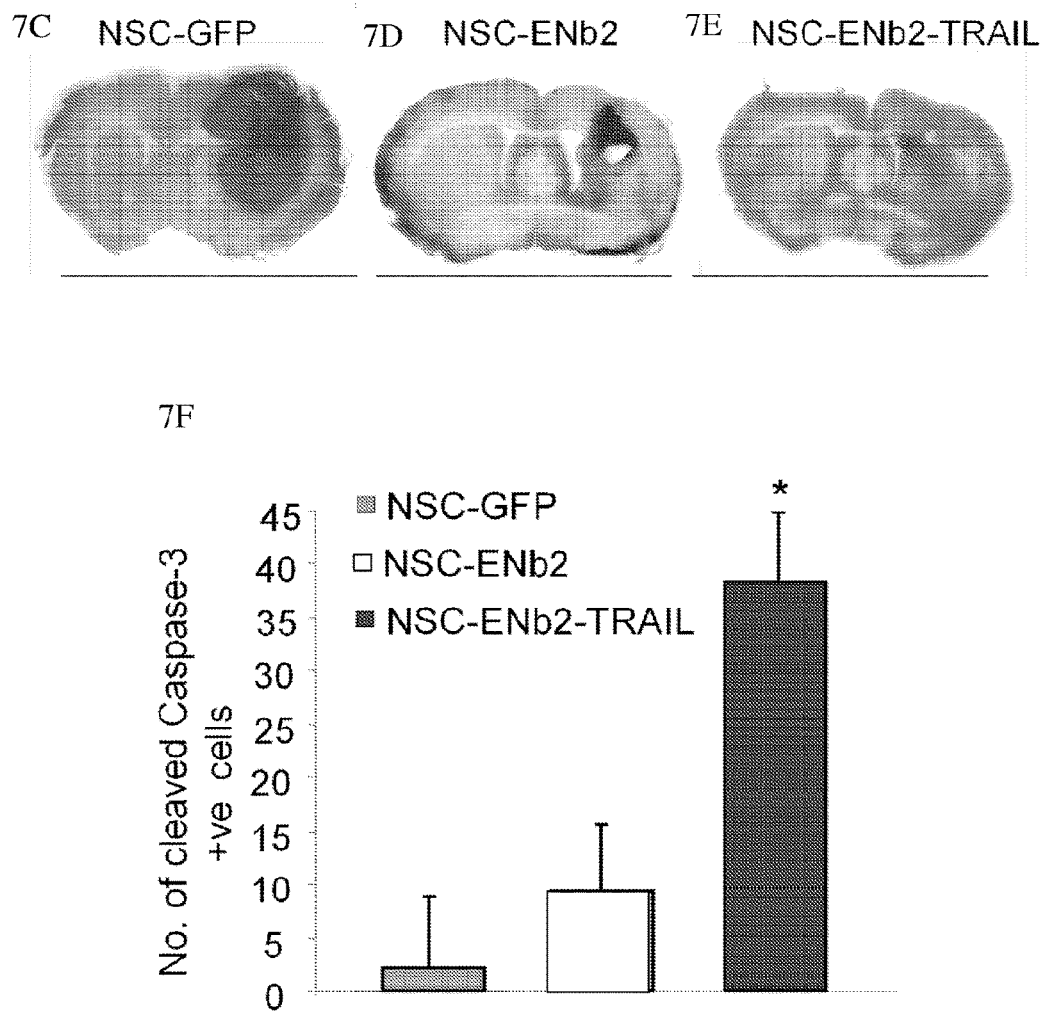
FIGS. 7A-7F demonstrate in vivo efficacy of ENb2 and ENb2-TRAIL secreting NSC on GBM volumes.

First, Cetuximab, a known monoclonal antibody targeting EGFR, was tested in GBM models. Mice bearing U87-mCherry-Fluc GBMs were administered Cetuximab or saline for a period of 11 days and imaged for tumor volumes. There was no significant change in GBM growth in Cetuximab-treated mice as compared to vehicle treatment (FIG. 7A). These results are in line with the findings from a number of pre-clinical and clinical trials in mice bearing GBMs and patients with GBMs respectively treated with Cetuximab as a single therapy (19-21). The efficacy of NSC delivered ENbs and its cytotoxic variant ENb2-TRAIL was tested in intracranial U87-mCherry-FLuc GBM model. NSC-ENb2 significantly inhibited tumor growth and NSC-ENb2-TRAIL efficiently prevented any outgrowth of the tumor for the duration of the treatment period (FIG. 7B). The presence of therapeutic NSC was confirmed by GFP fluorescence imaging on day 4 brain sections from mCherry expressing GBMs subjected to the different treatments (data not shown). H&E staining on brain sections also revealed a significant decrease in tumor volumes in NSC-ENb2-TRAIL and NSC-ENb2 treated mice as compared to controls (FIG. 7C-7E). Furthermore, a significantly increased cleaved caspase-3 staining was observed in day 4 brain sections obtained from NSC-ENb2-TRAIL-treated tumors as compared to NSC-ENb2 or control NSC-GFP treated tumors, showing the involvement of caspase-mediated apoptosis (FIG. 7F). These results reveal that tumoritropic NSC releasing ENb2 inhibits GBM growth and that the efficacy of ENb2-based therapy is enhanced by NSC releasing ENb2-TRAIL.

The compositions and methods described herein relate to compositions of multifunctional receptor targeted cancer therapeutics, which are a class of therapeutics that comprise different receptor targeted molecules; and have the ability to treat a broad spectrum of both sensitive and resistant tumor types.

REFERENCES

1. Citri A & Yarden Y (2006) EGF-ERBB signalling: towards the systems level. *Nat Rev Mol Cell Biol* 7(7): 505-516.
2. Ciardiello F & Tortora G (2008) EGFR antagonists in cancer treatment. *The New England journal of medicine* 358(11):1160-1174.
3. Martinelli E, De Palma R, Orditura M, De Vita F, & Ciardiello F (2009) Anti-epidermal growth factor receptor monoclonal antibodies in cancer therapy. *Clin Exp Immunol* 158(1):1-9.
4. Holliger P & Hudson P J (2005) Engineered antibody fragments and the rise of single domains. *Nat Biotechnol* 23(9):1126-1136.
5. Dolk E, et al. (2005) Induced refolding of a temperature denatured *llama* heavy-chain antibody fragment by its antigen. *Proteins* 59(3):555-564.
6. Stijlemans B, et al. (2004) Efficient targeting of conserved cryptic epitopes of infectious agents by single domain antibodies. African trypanosomes as paradigm. *J Biol Chem* 279(2):1256-1261.

7. Roovers R C, et al. (2007) Efficient inhibition of EGFR signaling and of tumour growth by antagonistic anti-EFGR Nanobodies. *Cancer Immunol Immunother* 56(3): 303-317.
8. Oliveira S, et al. (2010) Downregulation of EGFR by a novel multivalent nanobody-liposome platform. *J Control Release* 145(2):165-175.
9. Tan E H, et al. (2012) Gefitinib, cisplatin, and concurrent radiotherapy for locally advanced head and neck cancer: EGFR FISH, protein expression, and mutational status are not predictive biomarkers. *Annals of oncology: official journal of the European Society for Medical Oncology/ESMO* 23(4): 1010-1016.
10. Chen P, et al. (2011) EGFR-targeted therapies combined with chemotherapy for treating advanced non-small-cell lung cancer: a meta-analysis. *European journal of clinical pharmacology* 67(3):235-243.
11. Sasportas L S, et al. (2009) Assessment of therapeutic efficacy and fate of engineered human mesenchymal stem cells for cancer therapy. *Proceedings of the National Academy of Sciences of the United States of America* 106(12):4822-4827.
12. Shah K, et al. (2005) Glioma therapy and real-time imaging of neural precursor cell migration and tumor regression. *Ann Neurol* 57(1):34-41.
13. Shah K, Tung C H, Yang K, Weissleder R, & Breakefield X O (2004) Inducible release of TRAIL fusion proteins from a proapoptotic form for tumor therapy. *Cancer research* 64(9):3236-3242.
14. Wang X, et al. (2007) In vitro efficacy of immuno-chemotherapy with anti-EGFR human Fab-Taxol conjugate on A431 epidermoid carcinoma cells. *Cancer biology & therapy* 6(6):980-987.
15. Wu G, et al. (2007) Molecular targeting and treatment of an epidermal growth factor receptor-positive glioma using boronated cetuximab. *Clinical cancer research: an official journal of the American Association for Cancer Research* 13(4): 1260-1268.
16. Wajant H, et al. (2001) Differential activation of DR4 and -2 by soluble and membrane TRAIL allows selective surface antigen-directed activation of DR5 by a soluble TRAIL derivative. *Oncogene* 20(30):4101-4106.
17. Panner A, et al. (2009) A novel PTEN-dependent link to ubiquitination controls FLIPS stability and TRAIL sensitivity in glioblastoma multiforme. *Cancer research* 69(20):7911-7916.
18. Panner A, et al. (2010) Ubiquitin-specific protease 8 links the PTEN-Akt-AIP4 pathway to the control of FLIPS stability and TRAIL sensitivity in glioblastoma multiforme. *Cancer research* 70(12):5046-5053.
19. Carrasco-Garcia E, et al. (2011) Small tyrosine kinase inhibitors interrupt EGFR signaling by interacting with erbB3 and erbB4 in glioblastoma cell lines. *Experimental cell research* 317(10):1476-1489.
20. Hasselbalch B, et al. (2010) Prospective evaluation of angiogenic, hypoxic and EGFR-related biomarkers in recurrent glioblastoma multiforme treated with cetuximab, bevacizumab and irinotecan. *APMIS: acta pathologica, microbiologica, et immunologica Scandinavica* 118(8):585-594.
21. Hasselbalch B, et al. (2010) Cetuximab, bevacizumab, and irinotecan for patients with primary glioblastoma and progression after radiation therapy and temozolomide: a phase II trial. *Neuro-oncology* 12(5):508-516.

Example 2

Therapeutic Stem Cells Expressing Variants of EGFR-Specific Nanobodies have Anti-Tumor Effects The deregulation of the epidermal growth factor receptor (EGFR) has a significant role in the progression of tumors. Despite the development of a number of EGFR-targeting agents that can arrest tumor growth, their success is limited in several tumor types, particularly in the highly malignant glioblastoma multiforme (GBM). In this study, EGFR-specific nanobodies (ENb) and imageable and pro-apoptotic ENb-immuno-conjugates released from stem cells (SC) were generated and studied. This work relates to an EGFR-targeted therapy for GBM. It is demonstrated herein that ENbs released from SCs specifically localize to tumors, inhibit EGFR signaling resulting in reduced GBM growth and invasiveness in vitro and in vivo in both established and primary $CD133^+$ GBM cell lines. It is also demonstrated herein that ENb primes GBM cells for pro-apoptotic tumor necrosis factor-related apoptosis-inducing ligand (TRAIL)-induced apoptosis. Furthermore, SC-delivered immuno-conjugates of ENb and TRAIL target a wide spectrum of GBM cell types with varying degrees of TRAIL resistance and significantly reduce GBM growth and invasion in both established and primary invasive mouse models of GBM. This study is the first of its kind that demonstrates the efficacy of SC-based EGFR targeted therapy in GBMs.

The binding of ligands to the epidermal growth factor receptor (EGFR), a transmembrane glycoprotein, leads to activation of the EGFR tyrosine kinase and subsequent stimulation of signal transduction pathways that are involved in regulating cell proliferation, differentiation, migration and survival (1). Although present in normal cells, EGFR is overexpressed and mutated in a variety of tumors and has been associated with poor prognosis and decreased survival (2). Over the past two decades, much effort has been directed at developing anticancer agents that can interfere with EGFR activity and arrest tumor growth and, in some cases, cause tumor regression. The most commonly used pharmacologic approaches to inhibit EGFR signaling are small-molecule receptor tyrosine kinase inhibitors (sm-RTKI), like Gefinitib (Iressa, ZD1839) and Erlotinib (Tarceva, OSI-774) and monoclonal antibodies (mAb), such as Cetuximab (Erbitux, Mab-C225), Panitumumab (ABX-EGF) and Matuzumab (EMD72000). Whereas smRTKI exert their effects at the intracellular domain of EGFR to prevent tyrosine kinase activity, mAbs sterically block ligand binding to the extracellular domain of the receptor (3, 4). Although, the use of Erlotinib and Gefitinib have had moderate success in clinical trials in different tumor types, the use of mAbs has had limited to no success in cancer patients (3).

One aggressive tumor type with highly overactive EGFR pathway is Glioblastoma Multiforme (GBM), where the median survival rates remain only approximately 1 year (5). Gene amplification of the EGFR as well as activating mutations in EGFR play a significant role in gliomagenesis and can be found in up to 70% of all GBMs (6). The mute response of anti-EGFR therapies in GBMs as compared to other tumor types could be mainly attributed to the presence of the blood-brain barrier, transporter proteins and catabolism which are known to severely limit accumulation of the drugs at the tumor site and reducing their therapeutic efficacy (7). Therefore, there is an urgent need to develop novel EGFR targeting agents and to use innovative modes of delivery to enhance the efficacy of EGFR-targeting therapies for aggressive tumors like GBMs.

Recently, antibody-based anti-cancer therapies that involve smaller antibody fragments such as Fabs, ScFvs and nanobodies have been emerging (8). Nanobodies are derived from heavy chain-only antibodies found in camelids (e.g. *Llama glama*), and consist solely of the antigen-specific domain ($V_HH$) (9). These single-domain antibodies are significantly smaller in size (15 kDa) than scFv (28 kDa) or Fab (55 kDa), thereby potentially providing higher tissue dispersion than their counterparts (8). In addition, nanobodies are significantly more stable than $V_H$ domains and have improved penetration against immune-evasive (cryptic) antigens compared to mAbs (10, 11). Nanobodies specific for EGFR have recently been developed and shown to be able to sterically hinder the binding of EGF to the receptor, thereby inhibiting EGFR signaling (12, 13).

Neural stem cells (NSC) and mesenchymal stem cells (MSC) specifically home to tumors (21-23) (14, 15) (16). Described herein is the engineering of different bivalent EGFR targeting nanobodies (ENbs) and their imageable and pro-apoptotic immuno-conjugates for extracellular release from stem cells (SC) and characterization in vitro. Utilizing tumor models of malignant and CD133+ primary invasive GBM, ENb pharmacokinetics have been assessed in real time and the therapeutic efficacy of ENbs and its pro-apoptotic immuno-conjugates have been determined in vivo.

Results

Neural Stem Cells Secreting Anti-EGFR Nanobodies Inhibit EGFR Signaling in Tumor Cells:

To study the effect of ENbs secreted by mammalian cells on EGFR-mediated signaling in vitro and its effect on tumor progression, different versions of secretable ENbs were generated. The lentiviral plasmid constructs consisting of an N-terminal human Flt3 signal sequence (SS) fused to bivalent and bispecific ENbs (7D12/38G7 and 7D12/9G8; from here on called ENb1 and ENb2, respectively) are diagrammed in FIG. 8A. These constructs were either transfected directly into different cell types or packaged into lentivirus (LV) virions and utilized to create human and mouse NSC secreting ENbs. For assessing the their EGFR specificity, ENbs were purified from the conditioned medium of LV-ENb1 or LV-ENb2 transfected HEK293T/17 cells (FIG. 13) and tested on EGFR-positive (Her14) and EGFR-negative (NIH3T3 2.2) cell lines. Detection of EGFR immunoprecipitated by ENbs using Western blotting showed that both ENbs bound to EGFR (FIG. 8B). This binding of ENbs to the EGFR ectodomain prevented the binding of the ligand EGF to EGFR (FIG. 8C), resulting in reduced activation of EGFR and thereby inhibition of signaling via the Ras/MAPK and PI3K/AKT pathways in Her14 cells (FIG. 8D). These results demonstrate that ENbs secreted by mammalian cells are fully functional and have the potential to be utilized for EGFR-targeted therapy in cancer.

Next, we the possibility of using neural stem cells (NSC) as delivery vehicles of ENbs was explored. It was first confirmed that both human (h) and mouse (m) NSCs expressed significantly lower levels of EGFR than the commonly used established GBM line, U87 (FIG. 8E). Both mNSC and hNSC were efficiently transduced with LV-ENbs as revealed by GFP fluorescence (data not shown) and they constantly secreted significant amounts of ENbs in the culture medium over a period of at least 3 weeks as revealed by Western blotting (FIG. 14A). NSC-ENb were shown to retain the stem cell properties as shown by the expression of NSC marker nestin and their ability to differentiate into terminal cell types as shown by the expression of neuron specific marker, MAP-2 (FIG. 14B-14C). To explore the effect of ENbs on EGFR signaling in GBM cells, serum-starved GBM cell line LN229 (wt or engineered to overexpress EGFR or mutant EGFR variant, EGFRvIII) was incubated with various concentrations of purified ENbs and analyzed for EGFR phosphorylation and changes in downstream signaling molecules (FIG. 8F). EGFR activation as well as signaling via the PI3K/AKT and MAPK pathways was inhibited in LN229 cells irrespective of their EGFR expression status. To determine the efficacy of NSC-delivered ENb treatment for GBMs, LN229 GBM cells, engineered to express mCherry-FLuc, were co-cultured with either human or mouse NSC expressing GFP or ENb2 (data not shown). A slight reduction in LN229 proliferation was seen when co-cultured with hNSC-ENb2 and mNSC-Enb2 as compared to controls (FIG. 8G). Western blot analysis revealed that EGFR activation was significantly reduced when LN229 GBM cells were co-cultured with hNSC-ENb2 compared with hNSC-GFP (FIG. 8H). When a mixture of LN229-mCherry-Fluc cells and hNSC-GFP or hNSC-ENb2 cells was implanted in mice, a significant reduction in the Fluc signal intensity, depicting the number of viable LN229 GBM cells, was seen in NSC-ENb2/LN229-mCherry-Fluc implanted mice as compared to the controls (FIG. 8I). Comparable results were obtained when LN229-mCherry-Fluc cells further engineered to overexpress either EGFR or EGFRvIII (FIG. 15A-15D) were tested (FIG. 8I). These results demonstrate that NSC-expressed ENbs significantly inhibit EGFR and its downstream signaling pathways in GBMs and that NSC-delivered ENbs reduce GBM growth in vivo irrespective of the EGFR status of these lines.

Figure 16:
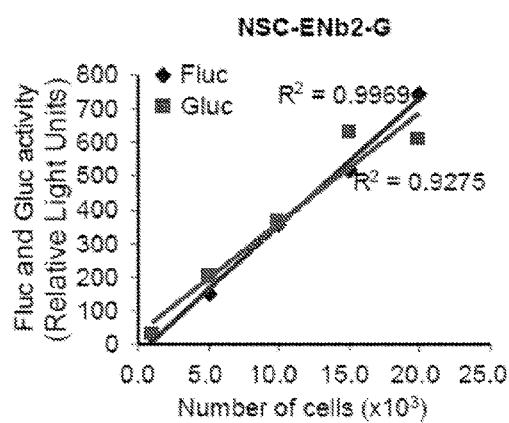
FIG. 16 demonstrates the characterization NSC-ENb for pharmacokinetic studies. Human NSC were co-transduced with LV-GFP-FLuc-positive and LV-ENb2-G. Cells were seeded at different densities and after 24 hours FLuc activity from cells and GLuc activity in the medium were measured to determine the correlation between NSC number and ENb2-G secretion.

Pharmacodynamics of NSC-ENbs In Vitro:

The concentration of EGFR targeting antibody to which tumor cells are exposed is critical for the success of anti-EGFR therapy. To study the secretion and intracellular localization of NSC produced ENbs, the ENbs were genetically fused to Gaussia luciferase (GLuc) (ENb-G) or to a fusion between GLuc and the fluorescent protein mCherry (GmC) (FIG. 9A) and created NSC lines expressing either ENb-G or ENb-GmC. The fusion proteins ENb1-G and ENb2-G were found to be EGFR-specific and competed with EGF-binding to EGFR, thus resulting in the inhibition of receptor activation (FIG. 9B-9D). NSC expressing FLuc were transduced with LV-ENb1-G and LV-ENb2-G to simultaneously analyze the efficiency of ENb secretion (GLuc signal) and NSC numbers (FLuc signal). Analysis of GLuc expression in NSC and the culture medium showed that approximately 65% of the ENbs were secreted in the medium (FIG. 9E). However, when ENb production and NSC number were correlated, ENb2-G was shown to be released from NSC twice as efficiently as ENb1-G (FIG. 9F, FIG. 16). To study localization of ENbs within the NSC compartments, ENb2-GmC-expressing NSC were utilized. ENb2 protein (mCherry expression) localized intracellularly to distinct cellular compartments (most likely prior to secretion) in contrast to the nucleo-cytoplasmic GFP expression (data not shown). These results show that ENbs retain functionality after fusion of imaging markers and the combined fluorescence and bioluminescence imaging provides an insight into ENb pharmacokinetics in vitro. Due to its superior secretion, ENb2 was chosen for further use and characterization in the following studies.

Pharmacokinetics of ENb2-G and NSC In Vivo:

To study the pharmacokinetics of NSC-delivered ENb2 in vivo, mice bearing subcutaneous mCherry-Fluc GBM tumors in a dorsal skinfold window chamber were implanted with NSC-ENb2-G at a ~1 mm distance from the tumor. While bioluminescence imaging showed the sustained on-site delivery of ENb2-G from NSC for a period of at least 5 days (FIG. 9G), intravital microscopy on that same set of mice showed the close proximity of NSC-ENb2-G to the tumor cells (data not shown). Serial bioluminescence imaging of systemically delivered ENb2-G in tumor-bearing mice revealed that after systemic delivery, the availability of ENb2-G to tumor cells decreased considerably with time and was barely present at 24 hrs post injection (FIG. 9H). To compare the in vivo distribution of systemically-delivered ENbs and NSC-delivered ENbs, mice bearing established subcutaneous mCherry-FLuc tumors were either implanted with NSC expressing ENb2-G or GFP (control) or injected systemically with ENb2-G. In vivo GLuc bioluminescence imaging and correlative ex vivo analysis of various internal organs revealed that ENb2-G was mostly present in the tumor when treated with NSC-ENb2-G or systemically injected ENb2-G. However, a substantial amount of ENb2-G was also found in liver, lung and kidney when tumor-bearing mice were systemically injected with ENb-2-G as compared to NSC-ENb2-G treatment (FIG. 9I-9J). Next, to assess whether tumor localization of ENb2-G depends on EGFR expression levels, mice bearing tumors generated from wild-type Gli36 or Gli36 GBM cells modified to overexpress EGFR (17) were administered with purified ENb2-G. GLuc bioluminescence imaging showed that ENb2-G accumulated in tumors, and that the levels of EGFR expression did not affect the extent of ENb2-G localization to tumors (FIG. 9K). These results indicate that NSC delivered ENb2 specifically targets tumor cells and is sustainably delivered to tumors in contrast to systemically administered ENbs.

Figures 10A, 10B, 10C, 10D, 10E, 10F, 10G, 10H:
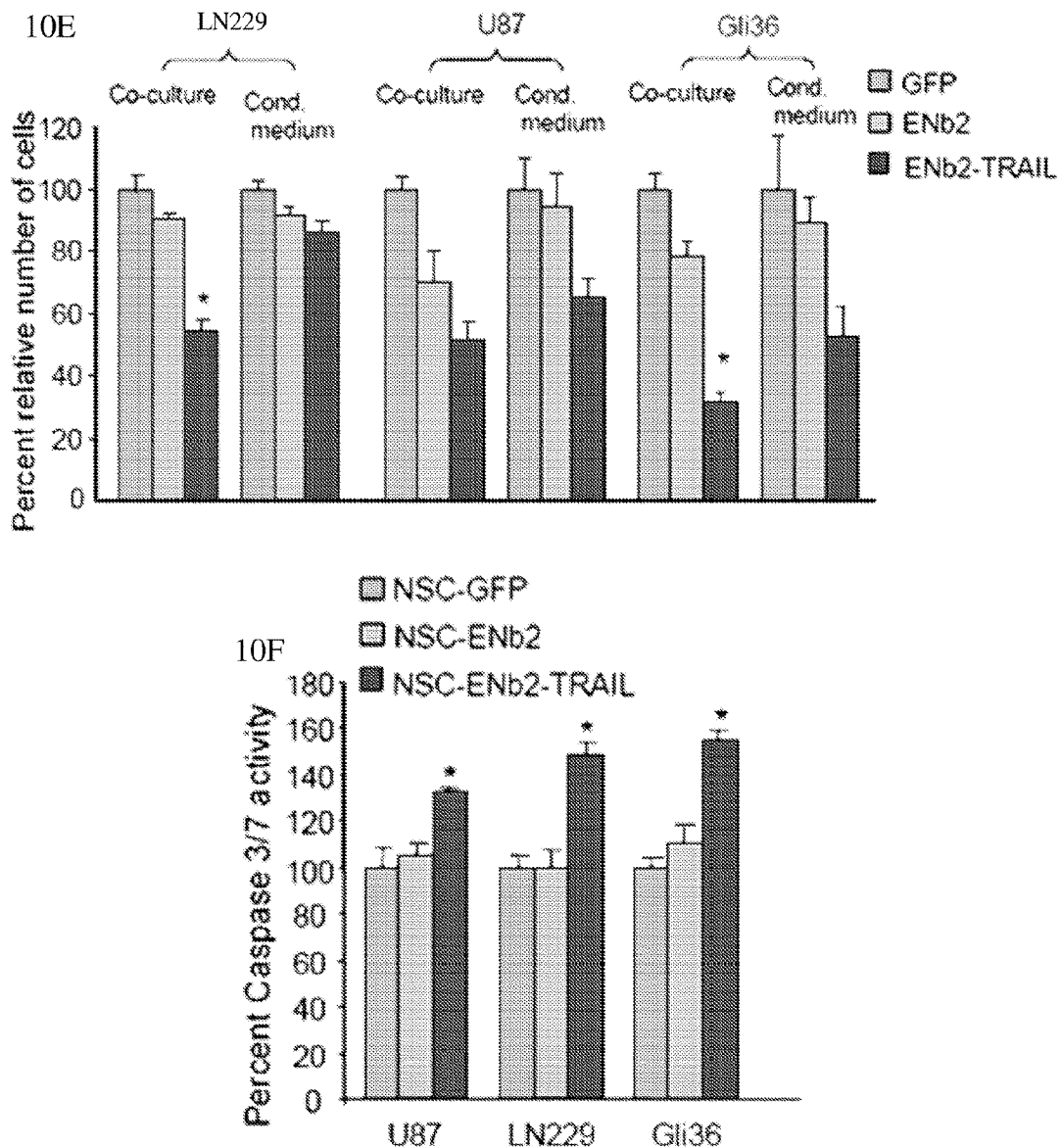
FIG. 10A depicts a schematic representation of lentiviral transfer vectors bearing cytotoxic variant of EGFR nanobody, ENb2-TRAIL.
FIG. 10B depicts Western blot analysis showing the EGFR specificity of ENb2-TRAIL on NIH3T3 and Her14 cell lines incubated with or without ENb2-TRAIL.
FIG. 10C depicts a graph of ELISA showing the EGF competition by ENb2-TRAIL.
FIG. 10D depicts Western blot analysis showing inhibition of EGFR and downstream signaling via the AKT and MAPK pathways on serum-starved Her14 and GBM (LN229, U87, Gli36) cells incubated with ENb2-TRAIL.
FIG. 10E depicts a graph of relative GBM cell viability in co-culture or after incubation with conditioned medium from mNSC expressing GFP, ENb2 or ENb2-TRAIL for 72 hours as determined by measuring FLuc activity.
FIG. 10F depicts a graph of caspase 3/7 activity in co-culture of GBM cells and mNSC.
FIG. 10G depicts a graph of relative LN229-mCherry-Fluc cell viability in co-culture with mNSC expressing GFP, ENb2, S-TRAIL or ENb2-TRAIL for 72 hours as determined by measuring FLuc activity.
FIG. 10H depicts Western blot analysis of LN229 cells treated with mNSC expressing ENb2, S-TRAIL or Enb-TRAIL. Data were represented as mean±SEM and * denotes p<0.05, students t-test.
Figure 17A:
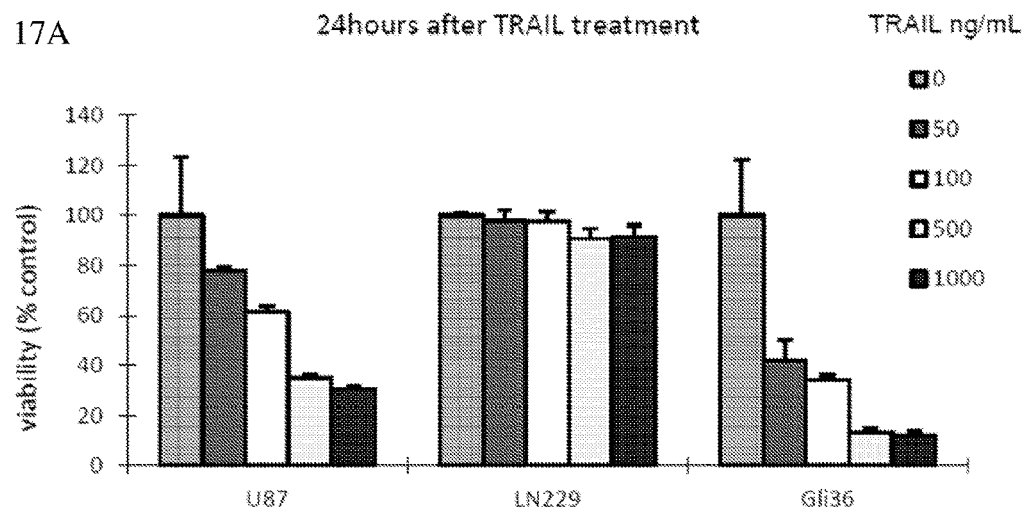
FIGS. 17A-17B demonstrate TRAIL-sensitivity of GBM cell lines.
Figure 17B:
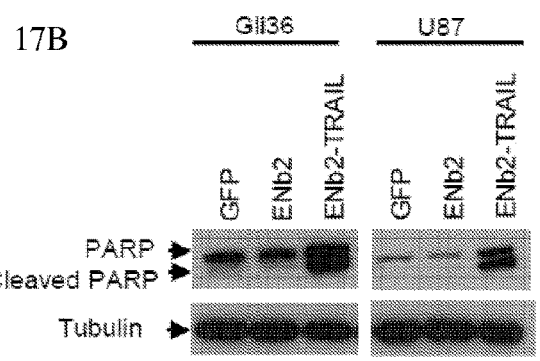
Figures 18A, 18B, 18C:
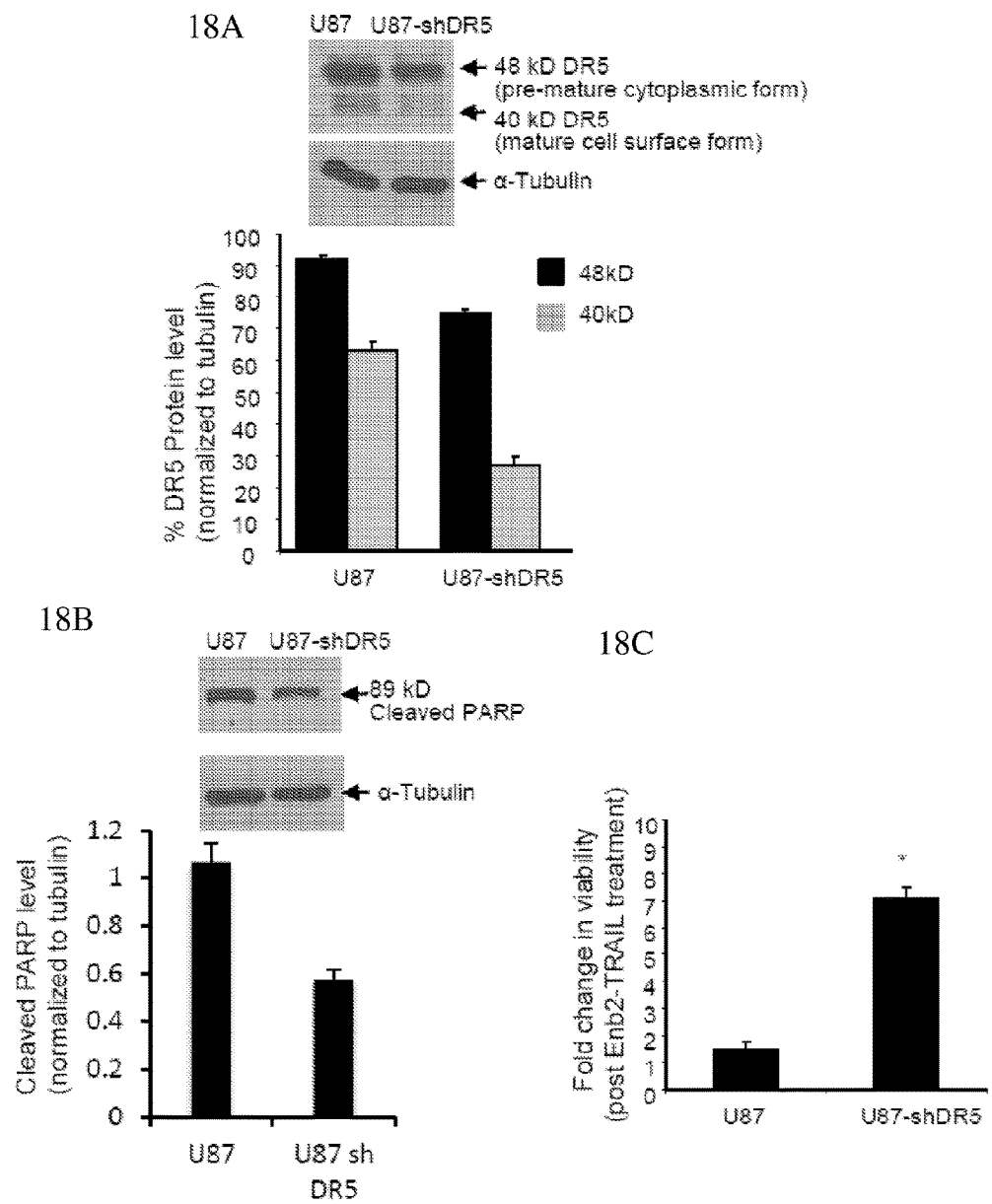
FIGS. 18A-18C demonstrate silencing of DR5 expression with shRNA reduces ENb-TRAIL induced apoptosis.

A Cytotoxic Variant of Anti-EGFR Nanobodies, ENb2-TRAIL, Efficiently Eliminates GBM Cells In Vitro:

To target tumor cell proliferation and death pathways simultaneously, LVs consisting of cDNA fusions encoding ENb2 and cytotoxic secretable TRAIL recombinant protein (ENb2-TRAIL) were engineered (FIG. 10A). HEK-293T transduced with LV-ENb2-TRAIL efficiently secreted ENb2-TRAIL (200 ng/mL per 106 cells) and when tested on Her14 (EGFR+) and NIH-3T3 (EGFR−) cell lines, ENb2-TRAIL was shown to specifically bind to EGFR (FIG. 10B) and compete with EGF ligand binding to EGFR (FIG. 10C). This resulted in the subsequent inhibition of EGFR signaling in Her14 and different GBM lines that have varying levels of resistance/sensitivity to TRAIL-induced apoptosis including LN229 cells that are most resistant to TRAIL (FIG. 10D; FIG. 17A). To explore the effect of NSC released ENb2-TRAIL on tumor cell proliferation and death, mouse NSC ((from here on called NSC) were engineered to express ENb2-TRAIL and GBM cells expressing mCherry-Fluc were co-cultured with NSC-ENb2-TRAIL, NSC-ENb2 and control NSC-GFP. NSC-ENb2 treatment resulted in reduced viability of all GBM cells Gli36, U87 and LN229 (FIG. 10E). Furthermore, NSC-ENb2-TRAIL treatment had a profound effect on GBM cell viability and resulted in TRAIL-mediated apoptosis as indicated by caspase-3/7 upregulation and PARP cleavage in TRAIL-sensitive (Gli36) and medial TRAIL-sensitive GBM (U87) lines (FIG. 10E-F; FIG. 17B). Enb2-TRAIL treatment of U87 cells in which death receptor (DR) 5 was knocked down resulted in significantly reduced PARP cleavage and increased cell viability as compared to controls indicating the interaction of ENb-TRAIL with death receptors (DR) and its downstream apoptosis pathway (FIGS. 18A-18C).

Next, the effects of NSC-TRAIL and NSC-ENb2-TRAIL on the TRAIL-resistant GBM line, LN229 were compared. Engineered NSC co-cultured in different ratios with LN229 cells showed that NSC-ENb2-TRAIL resulted in considerable reduction in GBM cell viability (FIG. 10G), increased caspase activation and PARP cleavage (FIG. 10H) as compared to NSC-TRAIL or NSC-ENb2. Together, these results indicate that the on-site delivery of ENb2 or ENb2-TRAIL via NSC (co-cultures) is more effective than the NSC conditioned medium treatment. Furthermore, NSC-released ENb2-TRAIL targets both cell proliferation and cell death pathways and has the ability to sensitize TRAIL resistant GBM cells.

Figure 11:
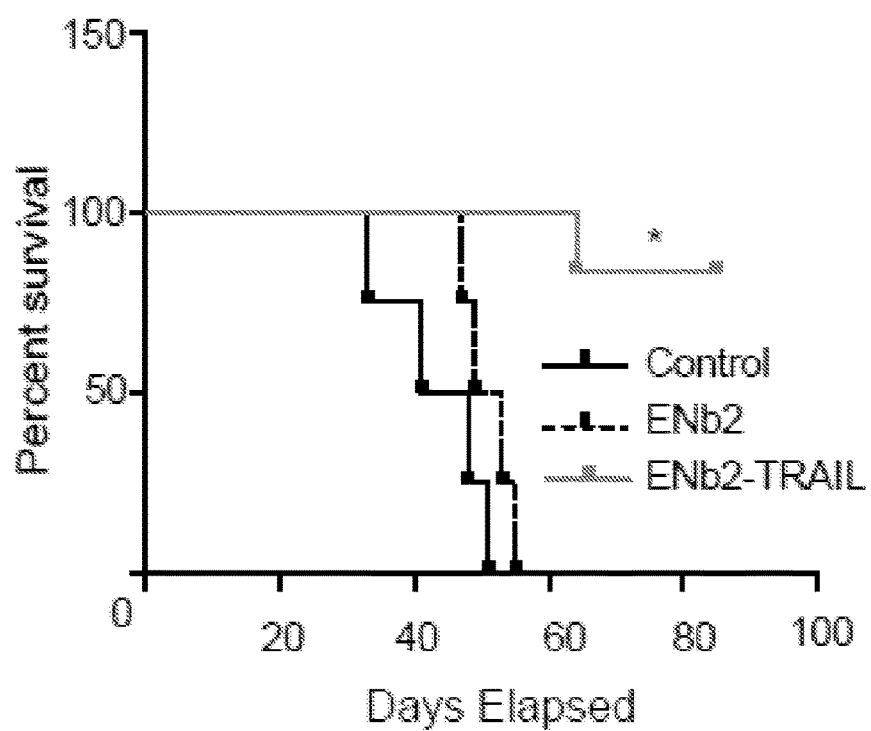
FIG. 11 demonstrates the in vivo efficacy of ENb2 and ENb2-TRAIL secreting NSC on GBM volumes. Kaplan-Meier survival curves of mice bearing established tumors and implanted with NSC expressing GFP, ENb2 or ENb2-TRAIL intratumorally (n=5 per group). * denotes p<0.05 as compared Enb2 and control groups, log-rank test.
Figure 19:
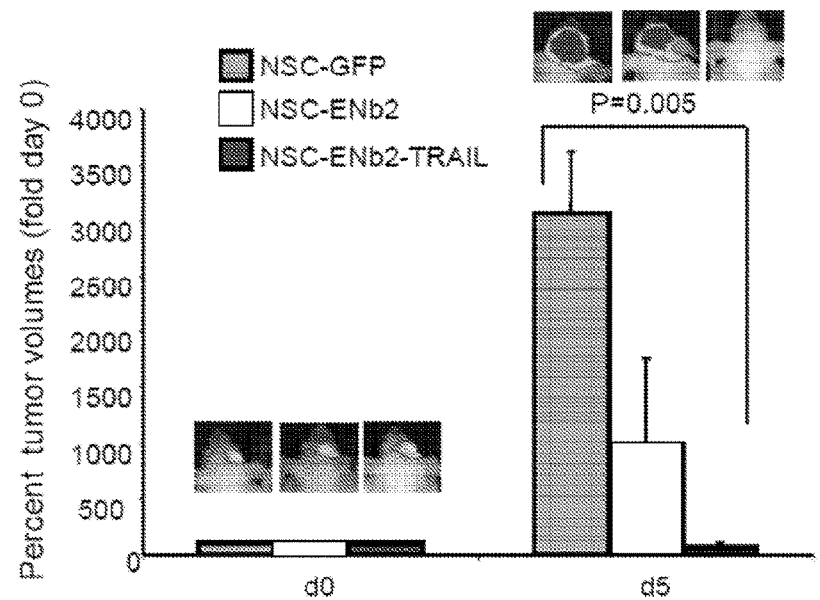
FIG. 19 demonstrates that Enb2 and Enb2-TRAIL-significantly influences tumor volumes in mice. Tumor volumes of nude mice intracranially implanted with U87-mCherry-FLuc mixed with mouse NSC expressing GFP, ENb2 or ENb2-TRAIL. Tumor volumes were measured on day 1 and 5 by means of FLuc bioluminescence imaging. Data were represented as mean±SEM and * denotes p<0.05, students t-test.
Figure 20:
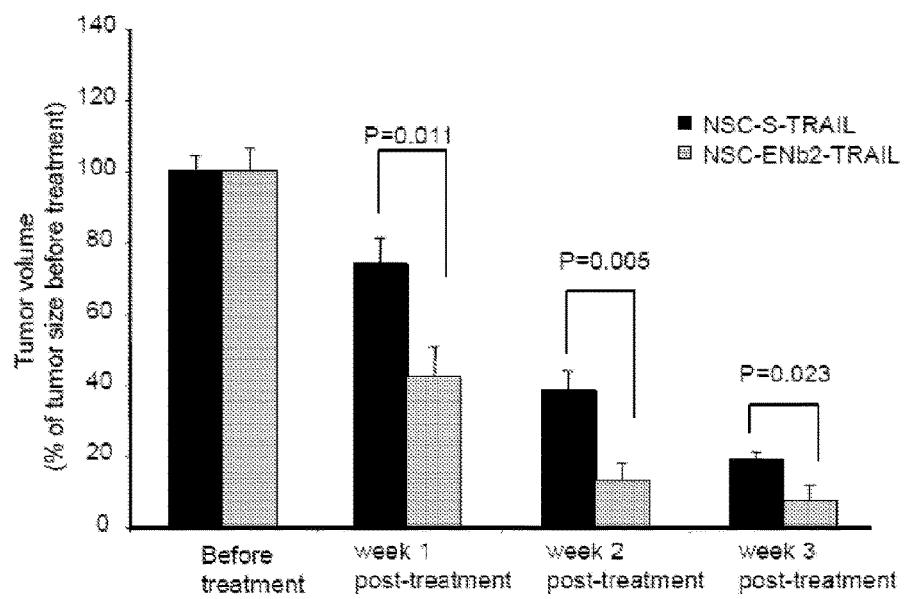
FIG. 20 demonstrates that Enb2-TRAIL has better therapeutic efficacy than S-TRAIL in vivo. Tumor volumes of nude mice bearing established intracranial U87-mCherry-FLuc tumors treated with NSC expressing S-TRAIL or ENb2-TRAIL. Data were represented as mean±SEM and * denotes p<0.05, students t-test.
Figure 21:
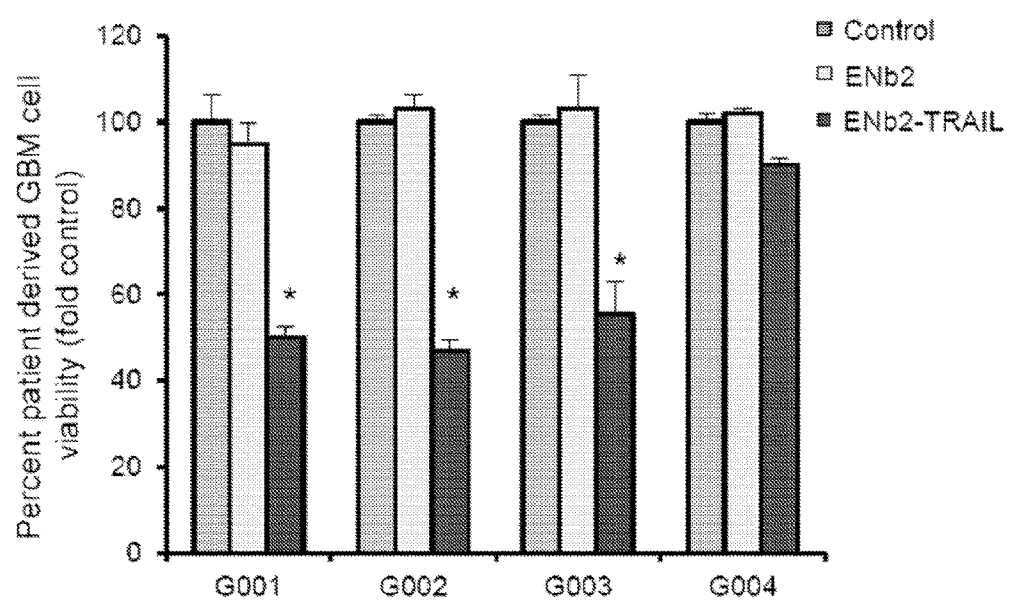
FIG. 21 depicts a graph of relative cell viability of different newly isolated patient derived GBM lines (G001-004) 48 hours after treatment with ENb2, Enb2-TRAIL (100 ng/mL) and control conditioned medium.

NSC-Delivered ENb2 and ENb2-TRAIL Significantly Influence GBMs In Vivo:

Cetuximab, a known monoclonal antibody targeting EGFR, was tested in GBM models. Mice bearing U87-mCherry-Fluc GBMs were administered Cetuximab or saline for a period of 11 days and imaged for tumor volumes. There was no significant change in GBM growth in Cetuximab-treated mice as compared to vehicle treatment (FIG. 7A). These results are in line with the findings from a number of pre-clinical and clinical studies where mice bearing GBMs and patients with GBMs were treated with Cetuximab as a single therapy (18-20). To investigate the efficacy of NSC delivered ENbs and its cytotoxic variant ENb2-TRAIL in vivo, a mix of U87-mCherry-FLuc GBM cells and NSC expressing only GFP and ENb2 or ENb2-TRAIL were implanted intracranially and tumor burden was imaged over time. Bioluminescence imaging revealed a significant inhibition of tumor growth when treated with NSC-ENb2 compared with the controls, whereas NSC-ENb2-TRAIL treated tumors regressed completely (FIG. 19). Since using a mixture of tumor and therapeutic stem cells is not clinically representative, the therapeutic efficacy on NSC-ENb2 and NSC-ENb2-TRAIL was tested in an established intracranial U87-mCherry-FLuc GBM model. NSC-ENb2 significantly inhibited tumor growth and NSC-ENb2-TRAIL efficiently prevented any outgrowth of the tumor for the duration of the treatment period (FIG. 7B). When the therapeutic efficacy of NSC-ENb2-TRAIL was compared with NSC-S-TRAIL in established U87-mCherry-Fluc tumors, NSC-ENb2-TRAIL treatment resulted in a significant reduction in tumor volumes as compared to NSC-S-TRAIL treatment (FIG. 20). The presence of therapeutic NSC was confirmed by GFP fluorescence imaging on day 4 brain sections from mCherry expressing GBMs subjected to the different treatments (data not shown). H&E staining on brain sections also revealed a significant decrease in tumor volumes in NSC-ENb2-TRAIL and NSC-ENb2 treated mice as compared to controls (FIG. 7C-7E). Furthermore, a significantly increased cleaved caspase-3 staining was observed in day 4 brain sections obtained from NSC-ENb2-TRAIL-treated tumors as compared to NSC-ENb2 or control NSC-GFP treated tumors, showing the involvement of caspase-mediated apoptosis (FIG. 7F). Mice treated with control NSC-GFP showed a median survival of 44.5 days. In contrast mice treated with control NSC-ENb2 showed a median survival of 51 days and 80% of mice treated with NSC-ENb2-TRAIL were alive 80 days after treatment (FIG. 11). These results reveal that tumoritropic NSC releasing ENb2 inhibits GBM growth and that the efficacy of ENb2-based therapy is enhanced by NSC releasing ENb2-TRAIL.

Figure 12A:
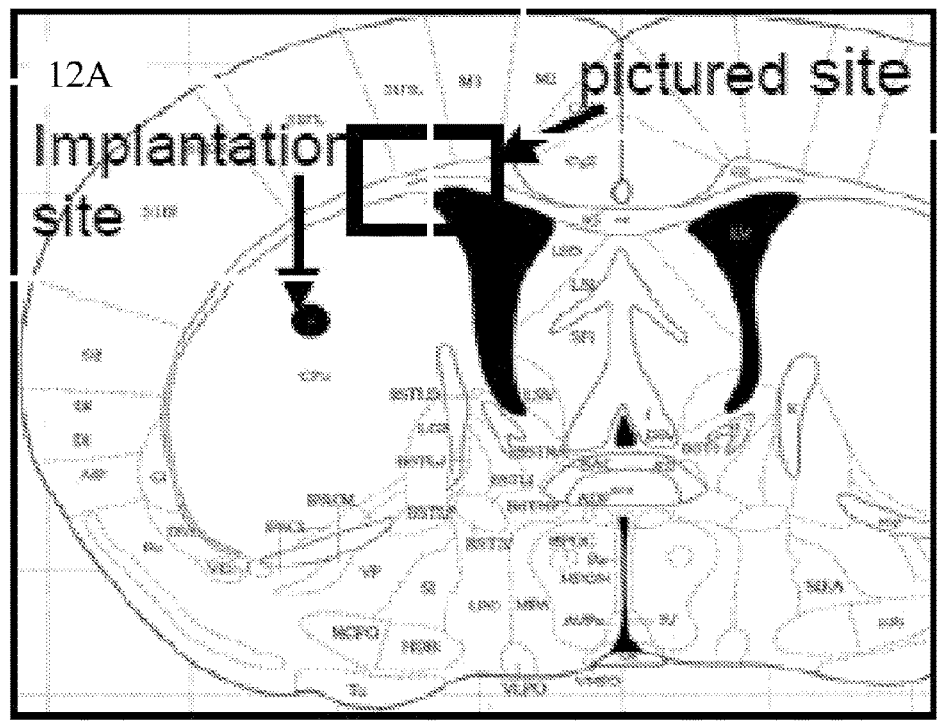
FIGS. 12A-12B demonstrate the in vivo efficacy of ENb2 and ENb2-TRAIL on inhibiting invasiveness of primary GBM cells.
Figure 12B:
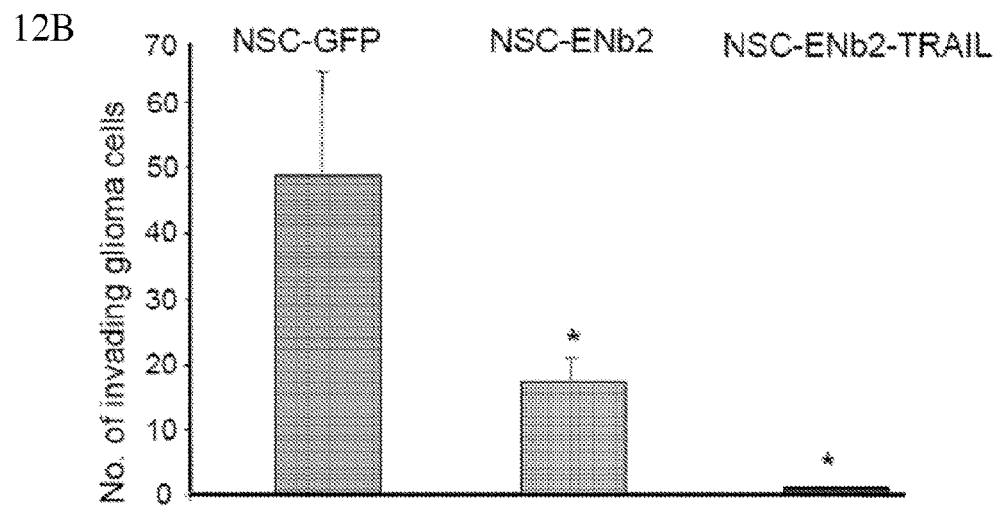
Figures 15A, 15B, 15C, 15D:
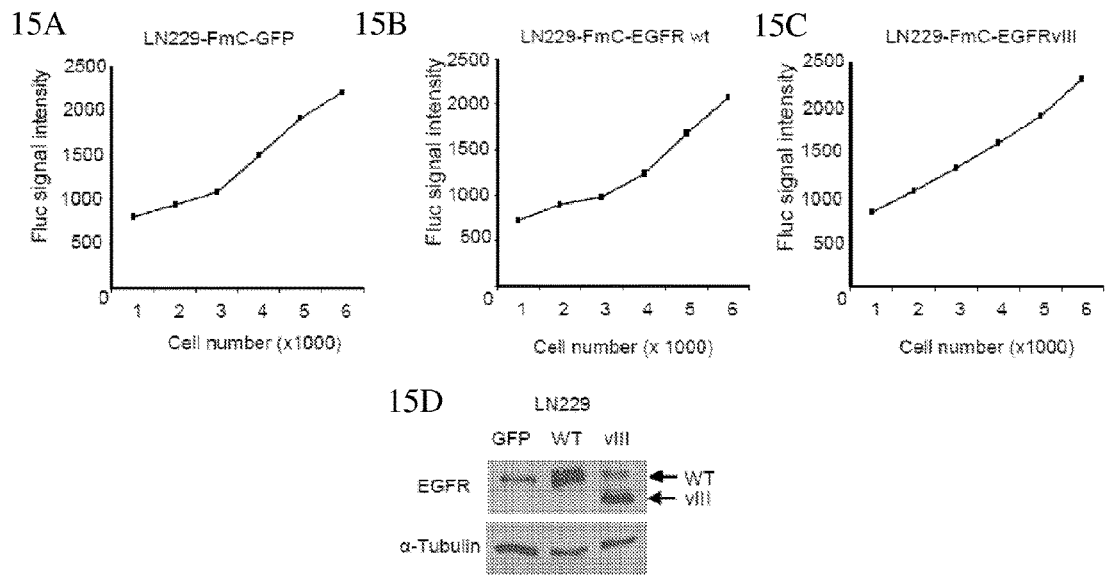
FIGS. 15A-15D demonstrate the characterization of engineered LN229 GBM lines overexpressing wt EGFR and mutant variant EGFRvIII: LN229-mCherry-Fluc GBM cells transduced with either LV-EGFR, LV-EGFRvIII or LV-GFP at M.O.I.=2. Depicted are plots demonstrating the correlation between the Fluc signal intensity and the LN229-FmC co-expressing GFP (15A), EGFRwt (15B) and EGFRvIII (15C).

ENb2 and ENb2-TRAIL inhibit invasiveness of primary GBM tumor cells: As increased invasion is one of the major impediments to successful therapies in malignant GBM, it was sought to evaluate whether the therapeutic NSC described herein can suppress GBM cell invasiveness in vivo. To this end, a xenograft mouse model, generated with CD133-positive primary GBM cells, that recapitulates the clinical settings of tumor cell invasiveness (21) was used. Mice bearing intracranial GBM8-mCherry-FLuc tumors were implanted with NSC expressing either only GFP or ENb2 or ENb2-TRAIL and GFP intratumorally. Mice were sacrificed at different days post NSC implantation and brain sections were visualized for NSC (GFP+) and tumor cells (mCherry+). A mixed presence of tumor cells and NSC was seen at the implantation site on day 1 post NSC implantation (FIG. 12A). Brain sections from mice sacrificed on day 7 post NSC implantation revealed that NSC-GFP tracked invading GBM8 cells (data not shown). Furthermore, NSC-ENb2 significantly inhibited tumor invasiveness by 60% and NSC-ENb2-TRAIL further suppressed the tumor cell invasion as almost no mCherry+ cells migrated out to the para-ventricular area (FIG. 12B). In contrast, from the tumors treated with control NSC, a significant number of GBM cells migrated/invaded along the white matter tract and reached an area adjacent to the lateral ventricle, indicating that the highly invasive property of the primary GBM cells was not affected by control NSC (FIG. 12A-12B). The broader therapeutic efficacy of Enb2-TRAIL was tested on patient derived GBM lines. A significant decrease in GBM cell viability was seen in most of the GBM lines treated with Enb2-TRAIL as compared to Enb2 and control treatment (FIG. 12B). These results reveal that NSC track invasive GBM cells in the brain and that ENb2 released by NSC inhibits invasiveness of primary GBM cells, which is further enhanced by the ENb2-TRAIL variant.

Discussion

Described herein is the assessment of the therapeutic efficacy of EGFR-targeting nanobodies and their imageable and proapoptotic variants in vitro and in mouse models of malignant and invasive GBMs. It is demonstrated that SC-delivered ENbs localize to tumors and that sustained release of ENbs from SCs inhibits EGFR signaling, reduces GBM growth and primes TRAIL-resistant GBM cells to TRAIL mediated apoptosis. Furthermore, SC delivered immuno-conjugate of ENb and TRAIL targets a wide spectrum of GBM cells with varying degrees of TRAIL resistance by targeting both cell death and survival pathways in established malignant and primary invasive mouse GBM models.

EGFR is frequently overexpressed and/or mutated in GBMs, resulting in increased activation of cell proliferation and pro-survival pathways and making EGFR an excellent target for cancer therapy (1). Despite efforts to improve the drug delivery across the blood brain barrier (BBB), the efficacy of anti-EGFR therapies for GBMs has been very limited (22). The discovery of heavy chain-only antibodies in camelids has lead to the development of nanobodies (9). These highly specific antibody fragments are relatively small with a size of only 15 kDa and therefore have higher tissue dispersion than mAbs (23) and do not elicit an immune response in the host. Also, some nanobodies are known to cross the BBB fairly easily (24, 25) and are therefore potentially better therapeutic agents than mAb or smRTKI for the treatment of brain malignancies. NSC and MSC migrate extensively toward brain tumors and therefore have an enormous therapeutic potential as gene delivery vehicles (14, 15) (26-30). In this study, NSC were armed with ENb and ENb-derived immunoconjugates and it was demonstrated that transgene expression is maintained in vitro and in vivo over a period of time without affecting stem cell properties. NSC released ENbs inhibited EGFR signaling in vitro and also resulted in a strong reduction of tumor growth in GBM-bearing mice. Interestingly, a more significant effect of ENb2 on GBM cell growth was observed in vivo than in culture conditions, which could possibly be due to the amplification of EGFR and gain of EGFR-dependence of tumor cells in mouse tumor models (31).

Although the in vitro response of GBM cell lines to anti-EGFR nanobodies is not directly predictive of the in vivo response, as is the case for U87 cells that were used for the established mouse GBM model, these data still give correlations about the downstream components of EGFR signaling. For example, U87 cells have a frame-shift mutation in the gene encoding PTEN, a tumor suppressor and a negative modulator of cell growth through inhibition of AKT signaling, rendering it inactive and reducing ligand-induced EGFR degradation (32). In accordance, while ENbs did not strongly affect the AKT activation in these cells, their inhibitory effects on the EGFR activation and MAPK p44/42 pathway were significant. In contrast, LN229 cells, which have wild type PTEN, showed inhibition of both AKT and MAPK p44/42 pathways with ENb treatment. PTEN status of tumors has been previously reported to affect the tumor response to EGF receptor tyrosine kinase inhibitor-based therapies in patients (33, 34). The results described herein indicate that the PTEN status of tumor cell lines alone does not predict the sensitivity of a tumor to ENb-based therapies. Therefore, it is tempting to speculate that NSC delivering anti-EGFR nanobodies provide maximal EGFR inhibition that may overcome resistance to EGFR-targeting therapies conferred by mutations in PTEN or PI3 kinase (32).

The in vivo studies with NSC-ENbs reveal that on-site delivery of ENbs within the tumors inhibit tumor growth but does not result in a significant regression of the tumor. This is consistent with previous studies on EGFR-inhibiting drugs, which have been shown to work mostly in combination with therapies like radiation and chemotherapy (22). To increase the efficacy of anti-EGFR nanobody-mediated therapy by simultaneously targeting the cell proliferation and death pathways, the immuno-conjugate ENb2-TRAIL, consisting of the nanobody ENb2 fused to the cytotoxic agent TRAIL was designed as described herein. TRAIL has the ability to selectively induce apoptosis in tumor cells while remaining harmless to normal cells (35). Binding of TRAIL to the pro-apoptotic death receptors DR4/DR5, induces a caspase-8-dependent apoptotic cascade resulting in tumor cell death (36). The results described herein reveal that ENb2-TRAIL induces caspase-3/7-mediated apoptosis in GBM cell lines with various degrees of TRAIL resistance. Interestingly, survival of the TRAIL-resistant cell line LN229 was significantly affected by ENb2-TRAIL, indicating that simultaneous EGFR inhibition might sensitize this cell line to TRAIL-induced apoptosis. Another interesting observation made in this study is that the efficacy of the treatment largely depends on how the drugs are delivered to tumor cells. GBM cells were found to be more sensitive to treatment with NSCs secreting therapeutic molecules compared to cells incubated with conditioned medium from the same NSCs. Therefore, it seems that continuous exposure of tumor cells to ENbs is more effective than a single high dose treatment. These observations further strengthen the rationale of using NSCs as delivery vehicles for sustained expression and release of therapeutics. Besides, ENb2-TRAIL was shown to be a highly effective therapeutic molecule in our mouse models, leading to tumor regression or stable disease.

Glioma cell invasion to distant sites in the brains with primary GBM tumors is one of the major impediments to successful therapies in malignant GBM. Tumor cells in the brain tend to migrate into the surrounding tissue, forming glioma microfoci (37). This results in invading cells escaping local treatments like surgery and thereby reducing the patients' chances of survival (37). In this study, it is demonstrated that NSC delivered anti-EGFR nanobodies reduce the number of migrating primary GBM cells by 60%, whereas ENb2-TRAIL prevents these highly invasive cells from migrating all together. Without wishing to be bound by theory, ENb2 could inhibit EGFR signaling pathways that are involved in cell migration, like the JAK-STAT pathway (38, 39). In combination with its inhibitory effect on tumor cell proliferation and the anti-tumor properties of TRAIL, this could lead to the observed significant reduction in migrating tumor cells.

In conclusion, the results described herein indicate the efficacy of on-site delivered anti-EGFR therapies for brain tumors. NSC-delivered anti-EGFR nanobodies inhibit tumor cell proliferation and migration, and combined with cytotoxic molecules significantly enhance therapeutic outcome.

Materials and Methods

Therapeutic Efficacy Studies In Vivo:

Cetuximab studies: U87-mCherry-FLuc cells were stereotactically implanted into the brains of nude mice (2×105 cells per mouse; n=6). Daily intraperitoneal administration of Cetuximab (40 mg/kg; ImClone Systems Inc) or saline vehicle was performed (n=3 per group) for 11 days and tumor volumes were determined by Fluc bioluminescence imaging as described (33). Efficacy of therapeutic NSC mixed with GBM cells: U87-mCherry-FLuc were mixed with NSC-GFP, NSC-ENb2 or NSC-ENb2-TRAIL and either implanted subcutaneously or stereotactically into the right frontal lobe of nude mice (from bregma: −2 mm lateral, −2 mm ventral). Mice (n=3 per group) were imaged for FLuc activity as described earlier (44). Efficacy of therapeutic NSC on established intracranial tumor: U87-mCherry-FLuc cells (1×105) were stereotactically implanted into the right frontal lobe of nude mice (from bregma: −2 mm lateral, −2 mm ventral). Mice bearing established tumors (as determined by Fluc bioluminescence imaging) were implanted with NSC expressing GFP, ENb2 or ENb2-TRAIL (5×105) intratumorally (n=7 per group), followed by a second implantation on day 7. Mice were imaged for FLuc activity as described previously (44). For survival studies, mice bearing established tumors were implanted with NSC expressing GFP, ENb2 or ENb2-TRAIL (5×105) intratumorally (n=5 per group) and followed for survival.

Statistical Analysis. Data were analyzed by Student's t test when comparing 2 groups. Data were expressed as mean+SEM, and differences were considered significant at $P<0.05$. Survival times of groups of mice were compared using a log-rank test.

Antibodies and Reagents: The following primary antibodies and reagents were used in this study: anti-*llama* VHH antibody, αHCV K208; anti-EGFR (BD Biosciences); anti-phosphorylated EGFR1068 (AbCam, Inc,); anti-Akt, anti-p44/42 MAP kinase and anti-phosphorylated p44/42 MAP kinase (Cell Signaling Technology); anti-phosphorylated Ser473 Akt (Invitrogen); anti-α-tubulin (Sigma-Aldrich); anti-human IgG antiserum (DakoCytomation); human recombinant EGF (R&D Systems,); biotinylated EGF from (Molecular Probes, Invitrogen, Carlsbad, Calif.); horseradish peroxidase-coupled streptavidin was (Jackson ImmunoResearch Laboratories); o-Phenylenediamine dihydrochloride (OPD) (Sigma Aldrich).

Lentiviral plasmid constructs: Based on the lentiviral transfer vector pLV-CICS/IG (1), the following therapeutic and diagnostic lentiviral vectors were engineered: 1) LV-ENb1, 2) LV-ENb2, 3) LV-ENb1-G, 4) LV-ENb2-G, 5) LV-ENb1-GmC, 6) LV-ENb2-GmC and 7) LV-ENb2-sTRAIL. To construct LV-ENb1 and LV-ENb2, nanobody (7D12/38G7 and 7D12/9G8) cDNA was PCR amplified using pAX51-7D12/9G8 and pAX51-7D12/38G7 vector as a template. An EcoRI restriction site was introduced in the forward primer and EcoRV and XhoI restriction sites separated by a stop codon in the reverse primer. To fuse the nanobodies to the hFlt3 secretion signal sequence, the PCR products were directionally inserted into EcoRI and XhoI sites of pKSR2-TSP-1 digested with EcoR1 and Xho1 resulting in pKSR2-ENb1 and pKSR2-ENb2 constructs (2). A 0.9 kb fragment encoding the hFlt3 signal sequence genetically fused to the EGFR nanobody cDNA was cut from the pKSR2-ENb1 and pKSR2-ENb2 constructs and inserted into the NheI and XhoI sites of lentiviral transfer vector, pLV-CICS/IG thus resulting in 1) LV-ENb1 and 2) LV-ENb2. To construct imageable variants of ENbs, the cDNA of mCherry was PCR amplified using pRSET-B-mCherry. The resulting PCR fragment was directionally inserted into EcoRV and XhoI digested LV-Gluc (3), resulting in LV-Gluc-mCherry. The cDNA encoding GLuc with an N-terminal fusion to an 18 amino acid linker was amplified by PCR, using LV-GLuc as a template.

The cDNA encoding the 18 amino acid linker fused to Gluc-mCherry was PCR amplified in a similar manner (forward and reverse primers: as described above). The resulting PCR products, Gluc (G) and Gluc-mCherry (GmC) were directionally inserted into EcoRV-XhoI digested LV-ENb1 and LV-ENb2, resulting in 3) LV-ENb1-G, 4) LV-ENb2-G, 5) LV-ENb1-GmC, 6) LV-ENb2-GmC. To construct the cytotoxic variant of EGFR nanobodies, the cDNA encoding S-TRAIL and an 18 amino acid linker was PCR amplified with LV-S-TRAIL as a template (4) using forward primer and a reverse primer introducing a XhoI site. The PCR fragment was directionally inserted into EcoRV-XhoI-digested LV-ENb2, resulting in 7) LV-ENb2-sTRAIL.

Lentiviral constructs were packaged as lentiviral vectors in HEK293T/17 cells using a helper virus-free packaging system as previously described (5).

Cell lines and Cell Culture: The following cells lines were used in this study: NIH/3T3 mouse fibroblasts (ATCC number: CRL-1658), Her14 cells, HEK293T/17 cells; and the established GBM cell lines U87, Gli36 and LN-229. The above mentioned cell lines were grown in DMEM supplemented with 10% Fetal Bovine Serum (FBS) and 1% penicillin/streptomycin. The highly invasive tumor initiating primary cell line GBM8 was grown in Neural Basal Medium (Invitrogen) supplemented with 3 mM L-Glutamine, 2 μg/ml heparin, 20 ng/ml EGF and 20 ng/ml bFGF (6, 7). Human neural stem cells (hNSCs) were grown as previously described (1). Mouse neural stem cells (mNSC) were cultured in Neurocult medium supplemented with Neurocult proliferation supplements (Stemcell Technologies), 20 ng/ml EGF, 20 ng/ml bFGF and 500 μl heparin (Stemcell Technologies).

Lentiviral transductions and engineering stable cell lines: Neural stem cells were transduced with lentiviral vectors at M.O.I.=4 in growth medium containing 8 μg/ml protamine sulphate (Sigma-Aldrich). GBM cells were transfected with the pico2A-FLuc-mCherry-PuroR vector using lipofectamine 2000 (Invitrogen) according to the manufacturer's recommendations and cells were selected on 500 ng/ml puromycin. Cells were visualized for GFP or mCherry expression by fluorescence microscopy. LN229 or LN229-mCherry-Fluc GBM cells transduced with either LV-EGFR, LV-EGFRvIII or LV-GFP at M.O.I.=2 and visualized for GFP or mCherry expression by fluorescence microscopy Production of anti-EGFR nanobodies: HEK 293T/17 cells were transfected with the described lentiviral plasmids using CaCl2-based transfection as described previously (5). After transfection, cells were cultured in regular DMEM. Nanobody-containing medium was collected, concentrated using 10 kDa cut-off columns (Millipore) and purified by incubating the concentrated medium with protein A/G-agarose beads (Santa Cruz Biotechnology) for 1.5 hours at 4° C. The protein A/G-bound nanobodies were eluted in 0.2 M glycine, pH 2.5 and subsequently neutralized in 1.0 M Tris-HCl pH 7.5 and dialyzed against phosphate buffered saline. Concentration of purified nanobodies was determined using a DC protein assay (Bio-Rad). Purity of the batches was analysed by loading 1 µg protein on SDS-PAGE gel and subsequent Coomassie Blue staining.

Western blot analysis: EGFR expression: Cell lysates from different cell lines were prepared using NP-40 lysis buffer (Boston Bioproducts, Worcester, Mass.) containing Complete protease inhibitor cocktail (Roche, Basel, Switzerland) and analyzed by Western blotting using rabbit anti-EGFR antibodies.

Presence of nanobodies in medium: The conditioned medium from NSC-ENb1 and NSC-ENb2 was collected on day 7, 14 and 21 after transduction and analyzed by western blotting using rabbit anti-VHH antibodies (αHCV K208). Inhibition of EGFR signaling: Her14 or tumor cells were seeded 100.000 cells per well in a 12-well tissue cluster and cultured overnight. Cells were serum starved in DMEM overnight. After serum starvation, cells were incubated with 0.1, 1, 10, 100 and 1000 nM of ENb in DMEM and stimulated with 50 ng/ml EGF for 8 minutes at 37° C. Cells were lysed in 2× Laemmli sample buffer and lysates were analyzed by Western blotting. Membranes were incubated with antibodies against phospho-Y1068 EGFR, EGFR, phospho-Ser437 Akt, Akt, phospho-p44/42 MAPK and p44/42 MAPK antibodies. Co-culture assays: Tumor cells and NSC were co-cultured in a 1:1 ratio for 2 days. Cell lysates were prepared in NP40 lysis buffer containing Complete protease inhibitor cocktail (Roche), and analyzed by Western blotting for phospho-Y1068 EGFR, tubulin, PARP and caspase-8.

Data quantification: Intensity of bands present on X-ray films was quantified using NIH ImageJ™ software.

(Co-)immunoprecipitation: NIH/3T3 and Her14 cells were seeded in 6-well tissue clusters (400.000 cells per well). Next day, cells were incubated with ENb (50 nM), ENb2-GLuc fusion (50 nM) or ENb2-TRAIL fusion (250 nM) for 10 minutes at 37° C. After incubation, cells were placed on ice, washed with ice-cold PBS and lysed in Triton X-100 lysis buffer (50 mM Tris-HCl, pH 7.5; 150 mM NaCl; 5 mM Na-EDTA, pH 8.0; 1% (v/v) Triton X-100) supplemented with Complete protease inhibitor cocktail (Roche). Cell lysates were incubated with lysis buffer-washed protein A/G-coated agarose beads for 1.5 hours at 4° C. while rotating. Beads were washed with lysis buffer and Laemmli sample buffer was added. Samples were analyzed using Western blotting and membranes were probed for EGFR.

EGF competition ELISA: Maxi-sorp ELISA plate was coated overnight with anti-human IgG antiserum in PBS at 4° C. After incubation, the wells were blocked with 5% bovine serum albumin (BSA) and incubated with the immuno-fusion protein EGFR ectodomain/Fc Wells were washed with PBS and incubated with a mixture of biotinylated EGF and serial dilutions of ENb containing medium (0.05-100 nM nanobody) was added. EGFR ECD/Fc-bound biotinylated EGF was detected by streptavidin-HRP and staining was performed using o-phenylenediamine (OPD). All incubations were performed at room temperature for 1 hour while shaking in 5% BSA in PBS.

Fluorescence microscopy, immunocytochemistry and flow cytometry: Intracellular localization: To determine where the ENb localizes intracellularly, hNSCs were infected with LV-ENb1-GmC and LV-ENb2-GmC. Cells were seeded in chamber slides (Electron Microscopy Sciences) and intracellular localization of the Nanobody/Gluc/mCherry fusions was analysed by fluorescence confocal microscopy. hNSC differentiation: To determine the effect of anti-EGFR nanobodies on stem cell differentiation, NSC, NSC-ENb1 and NSC-ENb2 were stained for nestin with phycoerythrin-labelled anti-nestin antibody (R&D Systems) using CytoFix/CytoPerm (BD Biosciences) according to the manufacturer's protocol. Samples were analyzed on the FACScalibur™ (BD Biosciences). mNSC differentiation: mNSCs were seeded in chamber slides and grown in Neurocult medium supplemented with differentiation supplements (Stemcell Technologies). Medium was refreshed daily and after 7 days, cells were stained for MAP2 as previously described (1).

TRAIL sensitivity assay: GBM cells were seeded at 10.000 cells per well in a 96-well plate. Next day, cells were incubated overnight with serial dilution of S-TRAIL-containing conditioned medium in regular growth medium. After 24 hours, cell viability was determined using the luminescence-based CellTiter Glo kit (Promega).

Co-culture of GBM and neural stem cells: Tumor cells were plated in 96-well plates at 10.000 cells per well in regular culture medium. Next day, 1) hNSC expressing ENb2 or GFP or 2) mNSC expressing ENb2, ENb2-TRAIL or GFP were seeded as neurospheres on top of the tumor cells in NSC culture medium or 3) tumor cells were incubated with 75% conditioned medium (GFP, ENb2, ENb2-TRAIL; conditioned for 3 days) and 25% fresh mNSC medium. Three days later, the relative number of tumor cells was determined by measuring the FLuc activity using 15 µg/ml D-luciferin or caspase 3/7 activity was measured using the CaspaseGlo™ assay (Promega). Cells were visualized by GFP and mCherry expression using fluorescence microscopy. LN229-mCherry-FLuc overexpressing EGFR or EGFRvIII were mixed with NSC-GFP or NSC-ENb2 and implanted subcutaneously. Mice were imaged for FLuc activity as described earlier (1).

Nanobody secretion by stem cells: GFP-Fluc-positive human NSCs were transduced with LV-ENb1-G and LV-ENb2-G at MOI=4 and 18 hours later cells were seeded at various densities (1000, 5000, 10.000, 15.000 and 20.000 per well) in a 96 well plate. Twenty-four hours later, medium and cells were analyzed for the presence of Gluc by adding coelenterazine (0.2 µg/ml). In parallel, the relative number of cells was determined by analyzing Fluc-activity in cells by adding D-luciferin (15 µg/ml). Data were obtained in triplicate from independent samples.

Nanobody pharmacokinetics in vivo: Localization of NSC and secretion of nanobodies: Window chambers were surgically attached to the skin of SCID mice. Upper layers of the skin were removed and U87-FLuc-TdTomato tumor cells were implanted. Next day (day 0), neural stem cells secreting ENb2-G were implanted next to the tumor. Using intravital microscopy, the localization of the tumor and the stem cells were visualized on day 1 and day 5. On the same days, mice were imaged for GLuc activity to determine the secretion of ENb2-G in vivo.

Localization and pharmacokinetics of intravenously injected anti-EGFR nanobodies: To follow the distribution of ENbs in vivo, mice with established subcutaneous Gli36-Fluc-mCherry or Gli36-Fluc-mCherry-EGFR+ were imaged for Gluc activity by injecting 60 μg of purified ENb2-G intravenously via the tail vein, followed by intravenous injection of 100 μg coelenterazine. Mice were imaged for GLuc activity every 5 minutes for 1.5 hours. In a separate set of mice, tumors and peripheral tissues (heart, liver, blood, lung, kidneys, urine) were removed 30 minutes after ENb2-G injection followed by coelenterazine treatment ex vivo to determine the biodistribution of ENb2-G. Localization and pharmacokinetics of NSC-secreted anti-EGFR nanobodies: Gli36-FLuc-mCherry tumor (5×106/tumor) were established subcutaneously in nude mice. Mice were imaged for FLuc activity and neural stem cells (4×106/tumor) expressing GFP (control) or ENb2-G were implanted next to the tumor (day 0). On days 2 and 3, mice were imaged for GLuc activity. On the final day, mice were sacrificed and tumors, heart, liver, blood, lung, kidneys were removed and subsequently imaged for GLuc activity.

Silencing of DR5 expression with shRNAs: U87 cells were transduced with PLKO-1 shDR5 (Open Biosystems) or control shRNAs and cells were selected on 1 μg/mL puromycin. Cell lysates were prepared using NP-40 lysis buffer (Boston Bioproducts, Worcester, Mass.) containing Complete protease inhibitor cocktail (Roche, Basel, Switzerland) and analyzed by Western blotting using rabbit anti-DR5 antibody. Both cell types were treated with Enb2-TRAIL (100 ng/mL) and assayed for cell viability as described above and analyzed for PARP cleavage by Western blotting as described above.

Immunohistochemical Studies: Mice were sacrificed by perfusion using 4% paraformaldehyde and their brains were isolated and fixed o/n in 4% paraformaldehyde at 4° C. Brains were cryosectioned and GFP-positive NSC and mCherry-positive GBM cells were visualized by fluorescence microscopy. Cleaved caspas-3 staining on brain sections was performed as described earlier (7).

Therapeutic efficacy of Enb2 and Enb2-TRAIL on primary patient derived GBM lines: Previously characterized human primary GBM cells, GBM8 cells (8) engineered to express mCherry-FLuc and were stereotactically implanted into the right frontal lobe of nude mice (1.5×105 cells per mouse) (from bregma: −2 mm lateral, −2 mm ventral). Three days later (day 0), mice were treated with intratumoral injection of NSC-GFP, NSC-ENb2 or NSC-ENb2-TRAIL (3×105, n=5 per group) and sacrificed on day 7 post-treatment. The field for counting invading cells was set at the white matter tract adjacent to the lateral ventricle. The average number of cells per field was determined by counting the cells in 6 random fields per well in 10× images of each well captured using (Olympus IX51). Newly isolated primary GBM lines (G001-004) were treated with ENb2, Enb2-TRAIL (100 ng/mL) and control conditioned medium and 48 hrs later cell viability was determined using the luminescence-based CellTiter Glo™ kit (Promega).

REFERENCES

1. Citri A, Yarden Y (2006) EGF-ERBB signalling: towards the systems level. Nat Rev Mol Cell Biol 7:505-516.
2. Ciardiello F, Tortora G (2008) EGFR antagonists in cancer treatment. N Engl J Med 358:1160-1174.
3. Martinelli E, et al. (2009) Anti-epidermal growth factor receptor monoclonal antibodies in cancer therapy. Clin Exp Immunol 158:1-9.
4. Sato J D, et al. (1983) Biological effects in vitro of monoclonal antibodies to human epidermal growth factor receptors. Mol Biol Med 1:511-529.
5. Lamborn K R, et al. (2008) Progression-free survival: an important end point in evaluating therapy for recurrent high-grade gliomas. Neuro Oncol 10:162-170.
6. Huang P H, Xu A M, White F M (2009) Oncogenic EGFR signaling networks in glioma. Sci Signal 2:re6.
7. Kroll R A, Neuwelt E A (1998) Outwitting the blood-brain barrier for therapeutic purposes: osmotic opening and other means. Neurosurgery 42:1083-1099; discussion 1099-1100.
8. Holliger P, Hudson P J (2005) Engineered antibody fragments and the rise of single domains. Nat Biotechnol 23:1126-1136.
9. Muyldermans S (2001) Single domain camel antibodies: current status. J Biotechnol 74:277-302.
10. Dolk E, et al. (2005) Induced refolding of a temperature denatured llama heavy-chain antibody fragment by its antigen. Proteins 59:555-564.
11. Stijlemans B, et al. (2004) Efficient targeting of conserved cryptic epitopes of infectious agents by single domain antibodies. African trypanosomes as paradigm. J Biol Chem 279:1256-1261.
12. Roovers R C, et al. (2007) Efficient inhibition of EGFR signaling and of tumour growth by antagonistic anti-EFGR Nanobodies. Cancer Immunol Immunother 56:303-317.
13. Roovers R C, et al. A biparatopic anti-EGFR nanobody efficiently inhibits solid tumour growth. Int J Cancer.
14. Aboody K S, et al. (2000) Neural stem cells display extensive tropism for pathology in adult brain: evidence from intracranial gliomas. Proc Natl Acad Sci USA 97:12846-12851.
15. Tang Y, et al. (2003) In vivo tracking of neural progenitor cell migration to glioblastomas. Hum Gene Ther 14:1247-1254.
16. Kauer T M, Figueiredo J L, Hingtgen S, Shah K (2012) Encapsulated therapeutic stem cells implanted in the tumor resection cavity induce cell death in gliomas. Nat Neurosci.
17. Arwert E, et al. (2007) Visualizing the dynamics of EGFR activity and antiglioma therapies in vivo. Cancer Res 67:7335-7342.
18. Carrasco-Garcia E, et al. (2011) Small tyrosine kinase inhibitors interrupt EGFR signaling by interacting with erbB3 and erbB4 in glioblastoma cell lines. Exp Cell Res 317:1476-1489.
19. Hasselbalch B, et al. (2010) Prospective evaluation of angiogenic, hypoxic and EGFR-related biomarkers in recurrent glioblastoma multiforme treated with cetuximab, bevacizumab and irinotecan. Apmis 118:585-594.
20. Hasselbalch B, et al. (2010) Cetuximab, bevacizumab, and irinotecan for patients with primary glioblastoma and progression after radiation therapy and temozolomide: a phase II trial. Neuro Oncol 12:508-516.
21. Wakimoto H, et al. (2009) Human glioblastoma-derived cancer stem cells: establishment of invasive glioma models and treatment with oncolytic herpes simplex virus vectors. Cancer Res 69:3472-3481.
22. Loew S, Schmidt U, Unterberg A, Halatsch M E (2009) The epidermal growth factor receptor as a therapeutic target in glioblastoma multiforme and other malignant neoplasms. Anticancer Agents Med Chem 9:703-715.

23. Tijink B M, et al. (2008) Improved tumor targeting of anti-epidermal growth factor receptor Nanobodies through albumin binding: taking advantage of modular Nanobody technology. Mol Cancer Ther 7:2288-2297.
24. Abulrob A, Sprong H, Van Bergen en Henegouwen P, Stanimirovic D (2005) The blood-brain barrier transmigrating single domain antibody: mechanisms of transport and antigenic epitopes in human brain endothelial cells. J Neurochem 95:1201-1214.
25. Gainkam L O, et al. (2008) Comparison of the biodistribution and tumor targeting of two 99mTc-labeled anti-EGFR nanobodies in mice, using pinhole SPECT/micro-CT. J Nucl Med 49:788-795.
26. Ehtesham M, et al. (2002) Induction of glioblastoma apoptosis using neural stem cell-mediated delivery of tumor necrosis factor-related apoptosis-inducing ligand. Cancer Res 62:7170-7174.
27. Hingtgen S, et al. (2008) Targeting multiple pathways in gliomas with stem cell and viral delivered S-TRAIL and Temozolomide. Mol Cancer Ther 7:3575-3585.
28. Ito S, et al. (2010) Human neural stem cells transduced with IFN-beta and cytosine deaminase genes intensify bystander effect in experimental glioma. Cancer Gene Ther 17:299-306.
29. Rath P, et al. (2009) Stem cells as vectors to deliver HSV/tk gene therapy for malignant gliomas. Curr Stem Cell Res Ther 4:44-49.
30. Shah K, et al. (2008) Bimodal viral vectors and in vivo imaging reveal the fate of human neural stem cells in experimental glioma model. J Neurosci 28:4406-4413.
31. Pandita A, et al. (2004) Contrasting in vivo and in vitro fates of glioblastoma cell subpopulations with amplified EGFR. Genes Chromosomes Cancer 39:29-36.
32. Vivanco I, et al. (2010) The phosphatase and tensin homolog regulates epidermal growth factor receptor (EGFR) inhibitor response by targeting EGFR for degradation. Proc Natl Acad Sci USA 107:6459-6464.
33. Kokubo Y, et al. (2005) Reduction of PTEN protein and loss of epidermal growth factor receptor gene mutation in lung cancer with natural resistance to gefitinib (IRESSA). Br J Cancer 92:1711-1719.
34. Sos M L, et al. (2009) PTEN loss contributes to erlotinib resistance in EGFR-mutant lung cancer by activation of Akt and EGFR. Cancer Res 69:3256-3261.
35. Corsten M F, Shah K (2008) Therapeutic stem-cells for cancer treatment: hopes and hurdles in tactical warfare. Lancet Oncol 9:376-384.
36. MacFarlane M, et al. (1997) Identification and molecular cloning of two novel receptors for the cytotoxic ligand TRAIL. J Biol Chem 272:25417-25420.
37. Nakada M, et al. (2007) Molecular targets of glioma invasion. Cell Mol Life Sci 64:458-478.
38. Dancey G, Begent R H, Meyer T (2009) Imaging in targeted delivery of therapy to cancer. Target Oncol 4:201-217.
39. Heskamp S, et al. (2010) ImmunoSPECT and immuno-PET of IGF-1R expression with the radiolabeled antibody R1507 in a triple-negative breast cancer model. J Nucl Med 51:1565-1572.
40. Oliveira S, et al. (2011) Rapid Visualization of Human Tumor Xenografts through Optical Imaging with a Near-infrared Fluorescent Anti-Epidermal Growth Factor Receptor Nanobody. Mol Imaging.
41. Hingtgen S D, et al. (2010) A novel molecule integrating therapeutic and diagnostic activities reveals multiple aspects of stem cell-based therapy. Stem Cells 28:832-841.
42. Kim K M, et al. (2008) Anti-CD30 diabody-drug conjugates with potent antitumor activity. Mol Cancer Ther 7:2486-2497.
43. Yazaki P J, et al. (2001) Tumor targeting of radiometal labeled anti-CEA recombinant T84.66 diabody and t84.66 minibody: comparison to radioiodinated fragments. Bioconjug Chem 12:220-228.
44. Sasportas L S, et al. (2009) Assessment of therapeutic efficacy and fate of engineered human mesenchymal stem cells for cancer therapy. Proc Natl Acad Sci USA 106: 4822-4827.

REFERENCES FOR METHODS

Shah K, et al. (2008) Bimodal viral vectors and in vivo imaging reveal the fate of human neural
stem cells in experimental glioma model. J Neurosci 28:4406-4413.
van Eekelen M, et al. (2010) Human stem cells expressing novel TSP-1 variant have anti-angiogenic effect on brain tumors. Oncogene 29:3185-3195.
Hingtgen S D, et al. (2010) A novel molecule integrating therapeutic and diagnostic activities reveals multiple aspects of stem cell-based therapy. Stem Cells 28:832-841.
Shah K, et al. (2004) Inducible release of TRAIL fusion proteins from a proapoptotic form for
tumor therapy. Cancer Res 64:3236-3242.
Kock N, Kasmieh R, Weissleder R, Shah K (2007) Tumor therapy mediated by lentiviral expression of shBcl-2 and S-TRAIL. Neoplasia 9:435-442.
Wakimoto H, et al. (2009) Human glioblastoma-derived cancer stem cells: establishment of invasive glioma models and treatment with oncolytic herpes simplex virus vectors. Cancer Res 69:3472-3481.
Sasportas L S, et al. (2009) Assessment of therapeutic efficacy and fate of engineered human mesenchymal stem cells for cancer therapy. Proc Natl Acad Sci USA 106: 4822-4827.
Wakimoto H, et al. (2009) Human glioblastoma-derived cancer stem cells: establishment of invasive glioma models and treatment with oncolytic herpes simplex virus vectors. Cancer Res 69:3472-3481.

```
EGFR mRNA sequence NCBI Ref Seq: NM_005228
                                                          SEQ ID NO: 5
    1 cccggcgca gcgcggccgc agcagcctcc gcccccgca cggtgtgagc gcccgacgcg 61 gccgaggcgg ccggagtccc gagctagccc cggcggccgc cgccgcccag accggacgac 121 aggccacctc gtcgcgtcc gcccgagtcc ccgcctcgcc gccaacgcca caaccaccgc 181 gcacggcccc ctgactccgt ccagtattga tcgggagagc cggagcgagc tcttcgggga
```

-continued

```
 241 gcagcgatgc gaccctccgg gacggccggg gcagcgctcc tggcgctgct ggctgcgctc
 301 tgcccggcga gtcgggctct ggaggaaaag aaagtttgcc aaggcacgag taacaagctc
 361 acgcagttgg gcacttttga agatcatttt ctcagcctcc agaggatgtt caataactgt
 421 gaggtggtcc ttgggaattt ggaaattacc tatgtgcaga ggaattatga tctttccttc
 481 ttaaagacca tccaggaggt ggctggttat gtcctcattg ccctcaacac agtggagcga
 541 attcctttgg aaaacctgca gatcatcaga ggaaatatgt actacgaaaa ttcctatgcc
 601 ttagcagtct tatctaacta tgatgcaaat aaaaccggac tgaaggagct gcccatgaga
 661 aatttacagg aaatcctgca tggcgccgtg cggttcagca caaccctgc cctgtgcaac
 721 gtggagagca tccagtggcg gacatagtc agcagtgact ttctcagcaa catgtcgatg
 781 gacttccaga accacctggg cagctgccaa aagtgtgatc caagctgtcc caatgggagc
 841 tgctggggtg caggagagga gaactgccag aaactgacca aaatcatctg tgcccagcag
 901 tgctccggc gctgccgtgg caagtccccc agtgactgct gccacaacca gtgtgctgca
 961 ggctgcacag gccccgggga gagcgactgc ctggtctgcc gcaaattccg agacgaagcc
1021 acgtgcaagg acacctgccc cccactcatg ctctacaacc ccaccacgta ccagatggat
1081 gtgaacccg agggcaaata cagctttggt gccacctgcg tgaagaagtg tccccgtaat
1141 tatgtggtga cagatcacgg ctcgtgcgtc cgagcctgtg gggccgacag ctatgagatg
1201 gaggaagacg gcgtccgcaa gtgtaagaag tgcgaagggc cttgccgcaa agtgtgtaac
1261 ggaataggta ttggtgaatt taaagactca ctctccataa atgctacgaa tattaaacac
1321 ttcaaaaact gcacctccat cagtggcgat ctccacatcc tgccggtggc atttaggggt
1381 gactccttca cacatactcc tcctctggat ccacaggaac tggatattct gaaaaccgta
1441 aaggaaatca cagggttttt gctgattcag gcttggcctg aaaacaggac ggacctccat
1501 gcctttgaga acctagaaat catacgcggc aggaccaagc aacatggtca gttttctctt
1561 gcagtcgtca gcctgaacat aacatccttg ggattacgct ccctcaagga gataagtgat
1621 ggagatgtga aatttcagg aaacaaaaat ttgtgctatg caaatacaat aaactggaaa
1681 aaactgtttg ggacctccgg tcagaaaacc aaaattataa gcaacagagg tgaaaacagc
1741 tgcaaggcca caggccaggt ctgccatgcc ttgtgctccc ccgagggctg ctggggcccg
1801 gagcccaggg actgcgtctc ttgccggaat gtcagccgag gcagggaatg cgtggacaag
1861 tgcaaccttc tggagggtga gccaagggag tttgtggaga actctgagtg catacagtgc
1921 cacccagagt gcctgcctca ggccatgaac atcacctgca caggacgggg accagacaac
1981 tgtatccagt gtgcccacta cattgacggc ccccactgcg tcaagacctg cccggcagga
2041 gtcatgggag aaaacaacac cctggtctgg aagtacgcag acgccggcca tgtgtgccac
2101 ctgtgccatc caaactgcac ctacggatgc actgggccag tcttgaagg ctgtccaacg
2161 aatgggccta agatcccgtc catcgccact gggatggtgg gggcctcct cttgctgctg
2221 gtggtggccc tggggatcgg cctcttcatg cgaaggcgcc acatcgttcg aagcgcacg
2281 ctgcgaggc tgctgcagga gagggagctt gtggagcctc ttacacccag tggagaagct
2341 cccaaccaag ctctcttgag gatcttgaag gaaactgaat tcaaaaagat caaagtgctg
2401 ggctccggtg cgttcggcac ggtgtataag ggactctgga tcccagaagg tgagaaagtt
2461 aaaattcccg tcgctatcaa ggaattaaga gaagcaacat ctccgaaagc caacaaggaa
2521 atcctcgatg aagcctacgt gatggccagc gtggacaacc cccacgtgtg ccgcctgctg
2581 ggcatctgcc tcacctccac cgtgcagctc atcacgcagc tcatgccctt cggctgcctc
2641 ctggactatg tccgggaaca caaagacaat attggctccc agtacctgct caactggtgt
```

-continued

```
2701  gtgcagatcg caaagggcat gaactacttg gaggaccgtc gcttggtgca ccgcgacctg
2761  gcagccagga acgtactggt gaaaacaccg cagcatgtca agatcacaga ttttgggctg
2821  gccaaactgc tgggtgcgga agagaaagaa taccatgcag aaggaggcaa agtgcctatc
2881  aagtggatgg cattggaatc aattttacac agaatctata cccaccagag tgatgtctgg
2941  agctacgggg tgaccgtttg ggagttgatg acctttggat ccaagccata tgacggaatc
3001  cctgccagcg agatctcctc catcctggag aaaggagaac gcctccctca gccacccata
3061  tgtaccatcg atgtctacat gatcatggtc aagtgctgga tgatagacgc agatagtcgc
3121  ccaaagttcc gtgagttgat catcgaattc tccaaaatgg cccgagaccc ccagcgctac
3181  cttgtcattc aggggatga agaatgcat ttgccaagtc ctacagactc caacttctac
3241  cgtgccctga tggatgaaga agacatggac gacgtggtgg atgccgacga gtacctcatc
3301  ccacagcagg gcttcttcag cagcccctcc acgtcacgga ctcccctcct gagctctctg
3361  agtgcaacca gcaacaattc caccgtggct tgcattgata gaaatgggct gcaaagctgt
3421  cccatcaagg aagacagctt cttgcagcga tacagctcag accccacagg cgccttgact
3481  gaggacagca tagacgacac cttcctccca gtgcctgaat acataaacca gtccgttccc
3541  aaaaggcccg ctggctctgt gcagaatcct gtctatcaca atcagcctct gaaccccgcg
3601  cccagcagag acccacacta ccaggacccc cacagcactg cagtgggcaa ccccgagtat
3661  ctcaacactg tccagcccac ctgtgtcaac agcacattcg acagccctgc ccactgggcc
3721  cagaaaggca gccaccaaat tagcctggac aaccctgact accagcagga cttctttccc
3781  aaggaagcca agccaaatgg catctttaag ggctccacag ctgaaaatgc agaataccta
3841  agggtcgcgc acaaaagcag tgaatttatt ggagcatgac cacgaggat agtatgagcc
3901  ctaaaaatcc agactctttc gatacccagg accaagccac agcaggtcct ccatcccaac
3961  agccatgccc gcattagctc ttagacccac agactggttt tgcaacgttt acaccgacta
4021  gccaggaagt acttccacct cgggcacatt ttgggaagtt gcattccttt gtcttcaaac
4081  tgtgaagcat ttacagaaac gcatccagca agaatattgt cccttttgagc agaaatttat
4141  ctttcaaaga ggtatatttg aaaaaaaaaa aaagtatatg tgaggatttt tattgattgg
4201  ggatcttgga gtttttcatt gtcgctattg attttttactt caatgggctc ttccaacaag
4261  gaagaagctt gctggtagca cttgctaccc tgagttcatc caggcccaac tgtgagcaag
4321  gagcacaagc cacaagtctt ccagaggatg cttgattcca gtggttctgc ttcaaggctt
4381  ccactgcaaa acactaaaga tccaagaagg ccttcatggc cccagcaggc cggatcggta
4441  ctgtatcaag tcatggcagg tacagtagga taagccactc tgtcccttcc tgggcaaaga
4501  agaaacggag gggatggaat tcttccttag acttactttt gtaaaaatgt ccccacggta
4561  cttactcccc actgatggac cagtggtttc cagtcatgag cgttagactg acttgtttgt
4621  cttccattcc attgttttga aactcagtat gctgccctg tcttgctgtc atgaaatcag
4681  caagagagga tgacacatca ataataact cggattccag cccacattgg attcatcagc
4741  atttggacca atagcccaca gctgagaatg tggaatacct aaggatagca ccgcttttgt
4801  tctcgcaaaa acgtatctcc taatttgagg ctcagatgaa atgcatcagg tcctttgggg
4861  catagatcag aagactacaa aaatgaagct gctctgaaat ctccttagc catcacccca
4921  acccccaaa attagtttgt gttacttatg gaagatagtt ttctcctttt acttcacttc
4981  aaaagctttt tactcaaaga gtatatgttc cctccaggtc agctgccccc aaacccctc
5041  cttacgcttt gtcacacaaa aagtgtctct gccttgagtc atctattcaa gcacttacag
```

-continued

```
5101 ctctggccac aacagggcat tttacaggtg cgaatgacag tagcattatg agtagtgtgg 5161 aattcaggta gtaaatatga aactagggtt tgaaattgat aatgctttca caacatttgc 5221 agatgtttta gaaggaaaaa agttccttcc taaaataatt tctctacaat tggaagattg 5281 gaagattcag ctagttagga gcccaccttt tttcctaatc tgtgtgtgcc ctgtaacctg 5341 actggttaac agcagtcctt tgtaaacagt gttttaaact ctccagtca atatccaccc 5401 catccaattt atcaaggaag aaatggttca gaaaatattt tcagcctaca gttatgttca 5461 gtcacacaca catacaaaat gttcctttg cttttaaagt aattttgac tcccagatca 5521 gtcagagccc ctacagcatt gttaagaaag tatttgattt ttgtctcaat gaaaataaaa 5581 ctatattcat ttccactcta aaaaaaaaaa aaaaaa
```

EGFR polypeptide sequence NCBI Ref Seq: NP_005219

SEQ ID NO: 6

```
   1 mrpsgtagaa llallaalcp asraleekkv cqgtsnkltq lgtfedhfls lqrmfnncev 61 vlgnleityv qrnydlsflk tiqevagyvl ialntverip lenlqiirgn myyensyala 121 vlsnydankt glkelpmrnl qeilhgavrf snnpalcnve siqwrdivss dflsnmsmdf 181 qnhlgscqkc dpscpngscw gageencqkl tkiicaqqcs grcrgkspsd cchnqcaagc 241 tgpresdclv crkfrdeatc kdtcpplmly npttyqmdvn pegkysfgat cvkkcprnyv 301 vtdhgscvra cgadsyemee dgvrkckkce gperkvcngi gigefkdsls inatnikhfk 361 nctsisgdlh ilpvafrgds fthtppldpq eldilktvke itgflliqaw penrtdlhaf 421 enleiirgrt kqhgqfslav vslnitslgl rslkeisdgd viisgnknlc yantinwkkl 481 fgtsgqktki isnrgensck atgqvchalc spegcwgpep rdcvscrnvs rgrecvdkcn 541 llegeprefv enseciqchp eclpqamnit ctgrgpdnci qcahyidgph cvktcpagvm 601 genntlvwky adaghvchlc hpnctygctg pglegcptng pkipsiatgm vgallllllvv 661 algiglfmrr rhivrkrtlr rllqerelve pltpsgeapn qallrilket efkkikvlgs 721 gafgtvykgl wipegekvki pvaikelrea tspkankeil deayvmasvd nphvcrllgi 781 cltstvqlit qlmpfgclld yvrehkdnig sqyllnwcvq iakgmnyled rrlvhrdlaa 841 rnvlvktpqh vkitdfglak llgaeekeyh aeggkvpikw malesilhri ythqsdvwsy 901 gvtvwelmtf gskpydgipa seissilekg erlpqppict idvymimvkc wmidadsrpk 961 freliiefsk mardpqrylv iqgdermhlp sptdsnfyra lmdeedmddv vdadeylipq 1021 qgffsspsts rtpllsslsa tsnnstvaci drnglqscpi kedsflqrys sdptgalted 1081 siddtflpvp eyinqsvpkr pagsvqnpvy hnqplnpaps rdphyqdphs tavgnpeyln 1141 tvqptcvnst fdspahwaqk gshqisldnp dyqqdffpke akpngifkgs taenaeylrv 1201 apqssefiga
```

DR4 mRNA sequence NCBI Ref Seq: NM_003844

SEQ ID NO: 7

```
   1 gcaggtgccc cgaaaagggg gcggggtcag gggtgccctg aactccgaat gcgaagttct 61 gtcttgtcat agccaagcac gctgcttctt ggattgacct ggcaggatgg cgccaccacc 121 agctagagta catctaggtg cgttcctggc agtgactccg aatcccggga gcgcagcgag 181 tgggacagag gcagccgcgg ccacacccag caaagtgtgg ggctcttccg cggggaggat 241 tgaaccacga ggcggggcc gaggagcgct ccctacctcc atgggacagc acggacccag 301 tgcccgggcc cgggcagggc gcgcccagg acccaggccg gcgcggggaag ccagccctcg 361 gctccgggtc cacaagacct tcaagtttgt cgtcgtcggg gtcctgctgc aggtcgtacc 421 tagctcagct gcaaccatca aacttcatga tcaatcaatt ggcacacagc aatgggaaca 481 tagcccttg ggagagttgt gtccaccagg atctcataga tcagaacatc ctggagcctg
```

-continued

```
 541 taaccggtgc acagagggtg tgggttacac caatgcttcc aacaatttgt ttgcttgcct
 601 cccatgtaca gcttgtaaat cagatgaaga agagagaagt ccctgcacca cgaccaggaa
 661 cacagcatgt cagtgcaaac caggaactt ccggaatgac aattctgctg agatgtgccg
 721 gaagtgcagc agagggtgcc ccagagggat ggtcaaggtc aaggattgta cgccctggag
 781 tgacatcgag tgtgtccaca agaatcagg caatggacat aatatatggg tgattttggt
 841 tgtgactttg gttgttccgt tgctgttggt ggctgtgctg attgtctgtt gttgcatcgg
 901 ctcaggttgt ggaggggacc ccaagtgcat ggacagggtg tgtttctggc gcttgggtct
 961 cctacgaggg cctggggctg aggacaatgc tcacaacgag attctgagca acgcagactc
1021 gctgtccact ttcgtctctg agcagcaaat ggaaagccag gagccggcag atttgacagg
1081 tgtcactgta cagtccccag gggaggcaca gtgtctgctg ggaccggcag aagctgaagg
1141 gtctcagagg aggaggctgc tggttccagc aaatggtgct gaccccactg agactctgat
1201 gctgttcttt gacaagtttg caaacatcgt gccctttgac tcctgggacc agctcatgag
1261 gcagctggac ctcacgaaaa atgagatcga tgtggtcaga gctggtacag caggcccagg
1321 ggatgccttg tatgcaatgc tgatgaaatg ggtcaacaaa actgacgga acgcctcgat
1381 ccacaccctg ctggatgcct tggagaggat ggaagagaga catgcaagag agaagattca
1441 ggacctcttg gtggactctg gaaagttcat ctacttagaa gatggcacag gctctgccgt
1501 gtccttggag tgaaagactc ttttaccag aggtttcctc ttaggtgtta ggagttaata
1561 catattaggt ttttttttt tttaacatgt atacaaagta aattcttagc caggtgtagt
1621 ggctcatgcc tgtaatccca gcactttggg aggctgaggc gggtggatca cttgaggtca
1681 gaagttcaag accagcctga ccaacatcgt gaaatgccgt ctttacaaaa aaatacaaaa
1741 attaactgga aaaaaaaaaa aaaa
```

DR4 polypeptide sequence NCBI Ref Seq: NP_003835
SEQ ID NO: 8

```
  1 mappparvhl gaflavtpnp gsaasgteaa aatpskvwgs sagrieprgg grgalptsmg
 61 qhgpsarara grapgprpar easprlrvhk tfkfvvvgvl lqvvpssaat iklhdqsigt
121 qqwehsplge lcppgshrse hpgacnrcte gvgytnasnn lfaclpctac ksdeeerspc
181 tttrntacqc kpgtfrndns aemcrkcsrg cprgmvkvkd ctpwsdiecv hkesgnghni
241 wvilvvtlvv plllvavliv cccigsgcgg dpkcmdrvcf wrlgllrgpg aednahneil
301 snadslstfv seqqmesqep adltgvtvqs pgeaqcllgp aeaegsqrrr llvpangadp
361 tetlmlffdk fanivpfdsw dqlmrqldlt kneidvvrag tagpgdalya mlmkwvnktg
421 rnasihtlld alermeerha rekiqdllvd sgkfiyledg tgsaysle
```

DR5 mRNA sequence NCBI Ref Seq: NM_003842
SEQ ID NO: 9

```
  1 acttggacgc gcttgcggag gattgcgttg acgagactct tatttattgt caccaacctg
 61 tggtggaatt tgcagttgca cattggatct gattcgcccc gccccgaatg acgcctgccc
121 ggaggcagtg aaagtacagc cgcgccgccc caagtcagcc tggacacata atcagcacg
181 cggccggaga accccgcaat ctctgcgccc acaaaataca ccgacgatgc ccgatctact
241 ttaagggctg aaacccacgg gcctgagaga ctataagagc gttccctacc gccatggaac
301 aacggggaca gaacgccccg gccgcttcgg gggcccggaa aaggcacggc ccaggaccca
361 gggaggcgcg gggagccagg cctgggcccc gggtccccaa gacccttgtg ctcgttgtcg
421 ccgcggtcct gctgttggtc tcagctgagt ctgctctgat cacccaacaa gacctagctc
481 cccagcagag agcggcccca caacaaaaga ggtccagccc ctcagaggga ttgtgtccac
```

-continued

```
 541 ctggacacca tatctcagaa gacggtagag attgcatctc ctgcaaatat ggacaggact
 601 atagcactca ctggaatgac ctccttttct gcttgcgctg caccaggtgt gattcaggtg
 661 aagtggagct aagtccctgc accacgacca gaaacacagt gtgtcagtgc aagaaggca
 721 ccttccggga agaagattct cctgagatgt gccggaagtg ccgcacaggg tgtcccagag
 781 ggatggtcaa ggtcggtgat tgtacaccct ggagtgacat cgaatgtgtc cacaaagaat
 841 caggtacaaa gcacagtggg gaagtcccag ctgtggagga gacggtgacc tccagcccag
 901 ggactcctgc ctctccctgt tctctctcag gcatcatcat aggagtcaca gttgcagccg
 961 tagtcttgat tgtggctgtg tttgtttgca agtctttact gtggaagaaa gtccttcctt
1021 acctgaaagg catctgctca ggtggtggtg gggaccctga gcgtgtggac agaagctcac
1081 aacgacctgg ggctgaggac aatgtcctca atgagatcgt gagtatcttg cagcccaccc
1141 aggtccctga gcaggaaatg gaagtccagg agccagcaga gccaacaggt gtcaacatgt
1201 tgtcccccgg ggagtcagag catctgctgg aaccggcaga agctgaaagg tctcagagga
1261 ggaggctgct ggttccagca atgaaggtg atcccactga gactctgaga cagtgcttcg
1321 atgactttgc agacttggtg cccttttgact cctgggagcc gctcatgagg aagttgggcc
1381 tcatggacaa tgagataaag gtggctaaag ctgaggcagc gggccacagg gacaccttgt
1441 acacgatgct gataaagtgg gtcaacaaaa ccgggcgaga tgcctctgtc cacaccctgc
1501 tggatgcctt ggagacgctg ggagagagac ttgccaagca gaagattgag gaccacttgt
1561 tgagctctgg aaagttcatg tatctagaag gtaatgcaga ctctgccatg tcctaagtgt
1621 gattctcttc aggaagtcag accttccctg gtttaccttt tttctggaaa agcccaact
1681 ggactccagt cagtaggaaa gtgccacaat tgtcacatga ccggtactgg aagaaactct
1741 cccatccaac atcacccagt ggatggaaca tcctgtaact tttcactgca cttggcatta
1801 ttttttataag ctgaatgtga taataaggac actatggaaa tgtctggatc attccgtttg
1861 tgcgtacttt gagatttggt ttgggatgtc attgttttca cagcactttt ttatcctaat
1921 gtaaatgctt tatttattta tttgggctac attgtaagat ccatctacac agtcgttgtc
1981 cgacttcact tgatactata tgatatgaac ctttttgggg tggggggtgc gggcagttc
2041 actctgtctc ccaggctgga gtgcaatggt gcaatcttgg ctcactatag ccttgacctc
2101 tcaggctcaa gcgattctcc cacctcagcc atccaaatag ctgggaccac aggtgtgcac
2161 caccacgccc ggctaatttt ttgtattttg tctagatata ggggctctct atgttgctca
2221 gggtggtctc gaattcctgg actcaagcag tctgcccacc tcagactccc aaagcggtgg
2281 aattagaggc gtgagccccc atgcttggcc ttacctttct acttttataa ttctgtatgt
2341 tattatttta tgaacatgaa gaaactttag taaatgtact tgtttacata gttatgtgaa
2401 tagattagat aaacataaaa ggaggagaca tacaatgggg gaagaagaag aagtcccctg
2461 taagatgtca ctgtctgggt tccagccctc cctcagatgt actttggctt caatgattgg
2521 caacttctac aggggccagt cttttgaact ggacaacctt acaagtatat gagtattatt
2581 tataggtagt tgtttacata tgagtcggga ccaaagagaa ctggatccac gtgaagtcct
2641 gtgtgtggct ggtccctacc tgggcagtct catttgcacc catagcccc atctatggac
2701 aggctgggac agaggcagat gggttagatc acacataaca atagggtcta tgtcatatcc
2761 caagtgaact tgagcccgt ttgggctcag gagatagaag acaaaatctg tctcccacgt
2821 ctgccatggc atcaaggggg aagagtagat ggtgcttgag aatggtgtga atggttgcc
2881 atctcaggag tagatggccc ggctcacttc tggttatctg tcaccctgag cccatgagct
2941 gccttttagg gtacagattg cctacttgag gaccttggcc gctctgtaag catctgactc
```

-continued

```
3001 atctcagaaa tgtcaattct taaacactgt ggcaacagga cctagaatgg ctgacgcatt 3061 aaggttttct tcttgtgtcc tgttctatta ttgttttaag acctcagtaa ccatttcagc 3121 ctctttccag caaacccttc tccatagtat ttcagtcatg aaggatcat ttatgcaggt 3181 agtcattcca ggagttttg tctttctg tctcaaggca ttgtgtgttt tgttccggga 3241 ctggtttggg tgggacaaag ttagaattgc ctgaagatca cacattcaga ctgttgtgtc 3301 tgtggagttt taggagtggg gggtgacctt tctggtcttt gcacttccat cctctcccac 3361 ttccatctgg catcccacgc gttgtcccct gcacttctgg aaggcacagg gtgctgctgc 3421 ctcctggtct ttgccttgc tgggccttct gtgcaggacg ctcagcctca gggctcagaa 3481 ggtgccagtc cggtcccagg tcccttgtcc cttccacaga ggccttccta gaagatgcat 3541 ctagagtgtc agccttatca gtgtttaaga ttttctttt attttaattt ttttgagac 3601 agaatctcac tctctcgccc aggctggagt gcaacggtac gatcttggcc cagtgcaacc 3661 tccgcctcct gggttcaagc gattctcgtg cctcagcctc cggagtagct gggattgcag 3721 gcacccgcca ccacgcctgg ctaattttg tatttttagt agagacgggg tttcaccatg 3781 ttggtcaggc tggtctcgaa ctcctgacct caggtgatcc accttggcct ccgaaagtgc 3841 tgggattaca ggcgtgagcc accagccagg ccaagctatt cttttaaagt aagcttcctg 3901 acgacatgaa ataattgggg gttttgttgt ttagttacat taggctttgc tatatcccca 3961 ggccaaatag catgtgacac aggacagcca tagtatagtg tgtcactcgt ggttggtgtc 4021 ctttcatgct tctgccctgt caaaggtccc tatttgaaat gtgttataat acaaacaagg 4081 aagcacattg tgtacaaaat acttatgtat ttatgaatcc atgaccaaat taaatatgaa 4141 accttatata aaaa
```

DR5 polypeptide sequence NCBI Ref Seq: NP_003833

SEQ ID NO: 10

```
  1 meqrgqnapa asgarkrhgp gpreargarp gprvpktlvl vvaavlllvs aesalitqqd 61 lapqqraapq qkrsspsegl cppghhised grdcisckyg qdysthwndl lfclrctrcd 121 sgevelspct ttrntvcqce egtfreedsp emcrkcrtgc prgmvkvgdc tpwsdiecvh 181 kesgtkhsge vpaveetvts spgtpaspcs lsgiiigvtv aavvlivavf vcksllwkkv 241 lpylkgicsg gggdpervdr ssqrpgaedn vlneivsilq ptqvpeqeme vqepaeptgv 301 nmlspgeseh llepaeaers qrrrllvpan egdptetlrq cfddfadlvp fdsweplmrk 361 lglmdneikv akaeaaghrd tlytmlikwv nktgrdasvh tlldaletlg erlakqkied 421 hllssgkfmy legnadsams
```

---

What is claimed herein is:

1. A multifunctional receptor targeted cancer therapeutic comprising a first portion comprising a nanobody reagent capable of specific binding with EGFR and EGFRvIII to inhibit EGFR signaling and a second portion comprising a therapeutic molecule capable of specific binding with DR5 to activate apoptosis, wherein the cancer therapeutic is binding specifically to targets on the same cancer cell.

2. The multifunctional receptor targeted cancer therapeutic of claim 1, wherein the therapeutic molecule is selected from the group consisting of: TRAIL; an extracellular domain of human TRAIL; an extracellular domain of human TRAIL comprising amino acids 114-281 of SEQ ID NO: 1; and S-TRAIL.

3. The multifunctional receptor targeted cancer therapeutic of claim 1, wherein the multifunctional receptor targeted cancer therapeutic further comprises a signal sequence or an isoleucine zipper domain.

* * * * *

SEQUENCE LISTING

<160> NUMBER OF SEQ ID NOS: 10

<210> SEQ ID NO 1
<211> LENGTH: 281
<212> TYPE: PRT
<213> ORGANISM: Homo sapiens

<400> SEQUENCE: 1

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
                35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Gly Lys Gln Gln Asn Ile Ser Pro
            100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
        130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 2
<211> LENGTH: 232
<212> TYPE: PRT
<213> ORGANISM: Mus musculus

<400> SEQUENCE: 2

Met Thr Val Leu Ala Pro Ala Trp Ser Pro Asn Ser Ser Leu Leu Leu
1               5                   10                  15

Leu Leu Leu Leu Leu Ser Pro Cys Leu Arg Gly Thr Pro Asp Cys Tyr
                20                  25                  30

Phe Ser His Ser Pro Ile Ser Ser Asn Phe Lys Val Lys Phe Arg Glu
            35                  40                  45

Leu Thr Asp His Leu Leu Lys Asp Tyr Pro Val Thr Val Ala Val Asn
        50                  55                  60

Leu Gln Asp Glu Lys His Cys Lys Ala Leu Trp Ser Leu Phe Leu Ala
65                  70                  75                  80

Gln Arg Trp Ile Glu Gln Leu Lys Thr Val Ala Gly Ser Lys Met Gln
                85                  90                  95

Thr Leu Leu Glu Asp Val Asn Thr Glu Ile His Phe Val Thr Ser Cys
            100                 105                 110

```
Thr Phe Gln Pro Leu Pro Glu Cys Leu Arg Phe Val Gln Thr Asn Ile
        115                 120                 125

Ser His Leu Leu Lys Asp Thr Cys Thr Gln Leu Leu Ala Leu Lys Pro
    130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
                165                 170                 175

Leu Glu Ala Thr Glu Leu Pro Glu Pro Arg Pro Arg Gln Leu Leu Leu
            180                 185                 190

Leu Leu Leu Leu Leu Leu Pro Leu Thr Leu Val Leu Leu Ala Ala Ala
        195                 200                 205

Trp Gly Leu Arg Trp Gln Arg Ala Arg Arg Arg Gly Glu Leu His Pro
    210                 215                 220

Gly Val Pro Leu Pro Ser His Pro
225                 230

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Ala Ser Gly Gly Pro Glu
1               5

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ser Thr Gly Gly Ser Gly Lys Pro Gly Ser Gly Glu Gly Ser Thr
1               5                   10                  15

Gly Gly

<210> SEQ ID NO 5
<211> LENGTH: 5616
<212> TYPE: DNA
<213> ORGANISM: Homo sapiens

<400> SEQUENCE: 5
ccccggcgca gcgcggccgc agcagcctcc gcccccgca cggtgtgagc gcccgacgcg      60
gccgaggcgg ccggagtccc gagctagccc cggcggccgc cgccgcccag accggacgac     120
aggccacctc gtcggcgtcc gcccgagtcc ccgcctcgcc gccaacgcca caaccaccgc     180
gcacggcccc ctgactccgt ccagtattga tcgggagagc cggagcgagc tcttcgggga     240
gcagcgatgc gaccctccgg gacggccggg gcagcgctcc tggcgctgct ggctgcgctc     300
tgcccggcga gtcgggctct ggaggaaaag aaagtttgcc aaggcacgag taacaagctc     360
acgcagttgg gcacttttga agatcatttt ctcagcctcc agaggatgtt caataactgt     420
gaggtggtcc ttgggaattt ggaaattacc tatgtgcaga ggaattatga tctttccttc     480
```

```
ttaaagacca tccaggaggt ggctggttat gtcctcattg ccctcaacac agtggagcga       540
attcctttgg aaaacctgca gatcatcaga ggaaatatgt actacgaaaa ttcctatgcc       600
ttagcagtct tatctaacta tgatgcaaat aaaaccggac tgaaggagct gcccatgaga       660
aatttacagg aaatcctgca tggcgccgtg cggttcagca acaaccctgc cctgtgcaac       720
gtggagagca tccagtggcg ggacatagtc agcagtgact ttctcagcaa catgtcgatg       780
gacttccaga accacctggg cagctgccaa agtgtgatc caagctgtcc aatgggagc        840 tgctggggtg caggagagga gaactgccag aaactgacca aaatcatctg tgcccagcag       900
tgctccgggc gctgccgtgg caagtccccc agtgactgct gccacaacca gtgtgctgca       960
ggctgcacag gccccgggga gagcgactgc ctggtctgcc gcaaattccg agacgaagcc      1020
acgtgcaagg acacctgccc cccactcatg ctctacaacc ccaccacgta ccagatggat      1080
gtgaaccccg agggcaaata cagctttggt gccacctgcg tgaagaagtg tccccgtaat      1140
tatgtggtga cagatcacgg ctcgtgcgtc cgagcctgtg gggccgacag ctatgagatg      1200
gaggaagacg gcgtccgcaa gtgtaagaag tgcgaagggc cttgccgcaa agtgtgtaac      1260
ggaataggta ttggtgaatt taaagactca ctctccataa atgctacgaa tattaaacac      1320
ttcaaaaact gcacctccat cagtggcgat ctccacatcc tgccggtggc atttagggt       1380 gactccttca cacatactcc tcctctggat ccacaggaac tggatattct gaaaaccgta      1440
aaggaaatca cagggttttt gctgattcag gcttggcctg aaaacaggac ggacctccat      1500
gcctttgaga acctagaaat catacgcggc aggaccaagc aacatggtca gttttctctt      1560
gcagtcgtca gcctgaacat aacatccttg ggattacgct ccctcaagga gataagtgat      1620
ggagatgtga aatttcagg aaacaaaaat tgtgctatg caaatacaat aaactggaaa       1680
aaactgtttg gacctccgg tcagaaaacc aaaattataa gcaacagagg tgaaaacagc      1740
tgcaaggcca caggccaggt ctgccatgcc ttgtgctccc ccgagggctg ctgggccg        1800 gagcccaggg actgcgtctc ttgccggaat gtcagccgag cagggaatg cgtggacaag       1860 tgcaaccttc tggagggtga gccaagggag tttgtggaga actctgagtg catacagtgc      1920
cacccagagt gcctgcctca ggccatgaac atcacctgca caggacgggg accagacaac      1980
tgtatccagt gtgcccacta cattgacggc ccccactgcg tcaagacctg cccggcagga      2040 gtcatggag aaaacaacac cctggtctgg aagtacgcag acgccggcca tgtgtgccac       2100
ctgtgccatc caaactgcac ctacggatgc actgggccag tcttgaagg ctgtccaacg       2160 aatgggcctta agatcccgtc catcgccact gggatggtgg gggccctcct cttgctgctg      2220
gtggtggccc tgggatcgg cctcttcatg cgaaggcgcc acatcgttcg gaagcgcacg      2280
ctgcggaggc tgctgcagga gagggagctt gtggagcctc ttacacccag tggagaagct      2340
cccaaccaag ctctcttgag gatcttgaag gaaactgaat tcaaaaagat caaagtgctg      2400
ggctccggtg cgttcggcac ggtgtataag ggactctgga tcccagaagg tgagaaagtt      2460
aaaattcccg tcgctatcaa ggaattaaga gaagcaacat ctcgaaagc caacaaggaa      2520 atcctcgatg aagcctacgt gatggccagc gtggacaacc cccacgtgtg ccgcctgctg      2580
ggcatctgcc tcacctccac cgtgcagctc atcacgcagc tcatgccctt cggctgcctc      2640
ctggactatg tccgggaaca caaagacaat attggctccc agtacctgct caactggtgt     2700
gtgcagatcg caaagggcat gaactacttg gaggaccgtc gcttggtgca ccgcgacctg      2760
gcagccagga acgtactggt gaaaacaccg cagcatgtca agatcacaga ttttggctgt     2820
gccaaactgc tgggtgcgga agagaaagaa taccatgcag aaggaggcaa agtgcctatc      2880
```

```
aagtggatgg cattggaatc aattttacac agaatctata cccaccagag tgatgtctgg    2940
agctacgggg tgaccgtttg ggagttgatg acctttggat ccaagccata tgacggaatc    3000
cctgccagcg agatctcctc catcctggag aaaggagaac gcctccctca gccacccata    3060
tgtaccatcg atgtctacat gatcatggtc aagtgctgga tgatagacgc agatagtcgc    3120
ccaaagttcc gtgagttgat catcgaattc tccaaaatgg cccgagaccc ccagcgctac    3180
cttgtcattc aggggatga aagaatgcat ttgccaagtc ctacagactc caacttctac    3240
cgtgccctga tggatgaaga agacatggac gacgtggtgg atgccgacga gtacctcatc    3300
ccacagcagg gcttcttcag cagccccctcc acgtcacgga ctcccctcct gagctctctg    3360
agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca atcagcctct gaaccccgcg    3600
cccagcagag acccacacta ccaggacccc cacagcactg cagtgggcaa ccccgagtat    3660
ctcaacactg tccagcccac ctgtgtcaac agcacattcg acagccctgc ccactgggcc    3720
cagaaaggca gccaccaaat tagcctggac aaccctgact accagcagga cttctttccc    3780
aaggaagcca agccaaatgg catctttaag ggctccacag ctgaaaatgc agaatacccta   3840 agggtcgcgc cacaaagcag tgaatttatt ggagcatgac cacggaggat agtatgagcc    3900
ctaaaaatcc agactctttc gatacccagg accaagccac agcaggtcct ccatcccaac    3960
agccatgccc gcattagctc ttagacccac agactggttt tgcaacgttt acaccgacta    4020
gccaggaagt acttccacct cgggcacatt ttgggaagtt gcattccttt gtcttcaaac    4080
tgtgaagcat ttacagaaac gcatccagca agaatattgt cccttgagc agaaatttat     4140 ctttcaaaga ggtatatttg aaaaaaaaaa aaagtatatg tgaggatttt tattgattgg    4200
ggatcttgga gttttcatt gtcgctattg attttactt caatgggctc ttccaacaag      4260
gaagaagctt gctggtagca cttgctaccc tgagttcatc caggcccaac tgtgagcaag    4320
gagcacaagc cacaagtctt ccagaggatg cttgattcca gtggttctgc ttcaaggctt    4380
ccactgcaaa acactaaaga tccaagaagg ccttcatggc cccagcaggc cggatcggta    4440
ctgtatcaag tcatggcagg tacagtagga taagccactc tgtcccttcc tgggcaaaga    4500
agaaacggag gggatggaat tcttccttag acttactttt gtaaaaatgt ccccacggta    4560
cttactcccc actgatggac cagtggtttc cagtcatgag cgttagactg acttgtttgt    4620
cttccattcc attgttttga aactcagtat gctgcccctg tcttgctgtc atgaaatcag    4680
caagagagga tgacacatca ataataact cggattccag cccacattgg attcatcagc      4740
atttggacca atagcccaca gctgagaatg tggaatacct aaggatagca ccgcttttgt    4800
tctcgcaaaa acgtatctcc taatttgagg ctcagatgaa atgcatcagg tcctttgggg    4860
catagatcag aagactacaa aaatgaagct gctctgaaat ctcctttagc catcacccca    4920 acccccaaa attagtttgt gttacttatg aagatagtt ttctccttttt acttcacttc      4980 aaaagctttt tactcaaaga gtatatgttc cctccaggtc agctgccccc aaaccccctc    5040
cttacgcttt gtcacacaaa aagtgtctct gccttgagtc atctattcaa gcacttacag    5100
ctctggccac aacagggcat tttacaggtg cgaatgacag tagcattatg agtagtgtgg    5160
aattcaggta gtaaatatga aactagggtt tgaaattgat aatgctttca caacatttgc    5220
```

```
agatgtttta gaaggaaaaa agttccttcc taaaataatt tctctacaat tggaagattg   5280
gaagattcag ctagttagga gcccacctttt tttcctaatc tgtgtgtgcc ctgtaacctg   5340
actggttaac agcagtcctt tgtaaacagt gttttaaact ctcctagtca atatccaccc   5400
catccaattt atcaaggaag aaatggttca gaaatatttt tcagcctaca gttatgttca   5460
gtcacacaca catacaaaat gttccttttg cttttaaagt aattttttgac tcccagatca   5520 gtcagagccc ctacagcatt gttaagaaag tatttgatttt ttgtctcaat gaaataaaa   5580 ctatattcat ttccactcta aaaaaaaaaa aaaaaa                              5616
```

<210> SEQ ID NO 6
<211> LENGTH: 1210
<212> TYPE: PRT
<213> ORGANISM: Homo sapiens

<400> SEQUENCE: 6

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
        290                 295                 300
```

Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
            325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
            690                 695                 700

Arg Ile Leu Lys Glu Thr Glu Phe Lys Lys Ile Lys Val Leu Gly Ser
705                 710                 715                 720

```
Gly Ala Phe Gly Thr Val Tyr Lys Gly Leu Trp Ile Pro Glu Gly Glu
            725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
        850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
        930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125
```

| His | Ser | Thr | Ala | Val | Gly | Asn | Pro | Glu | Tyr | Leu | Asn | Thr | Val | Gln |
|-----|-----|-----|-----|-----|-----|-----|-----|-----|-----|-----|-----|-----|-----|-----|
| 1130 | | | | | 1135 | | | | | 1140 | | | | |

| Pro | Thr | Cys | Val | Asn | Ser | Thr | Phe | Asp | Ser | Pro | Ala | His | Trp | Ala |
|-----|-----|-----|-----|-----|-----|-----|-----|-----|-----|-----|-----|-----|-----|-----|
| 1145 | | | | | 1150 | | | | | 1155 | | | | |

| Gln | Lys | Gly | Ser | His | Gln | Ile | Ser | Leu | Asp | Asn | Pro | Asp | Tyr | Gln |
|-----|-----|-----|-----|-----|-----|-----|-----|-----|-----|-----|-----|-----|-----|-----|
| 1160 | | | | | 1165 | | | | | 1170 | | | | |

| Gln | Asp | Phe | Phe | Pro | Lys | Glu | Ala | Lys | Pro | Asn | Gly | Ile | Phe | Lys |
|-----|-----|-----|-----|-----|-----|-----|-----|-----|-----|-----|-----|-----|-----|-----|
| 1175 | | | | | 1180 | | | | | 1185 | | | | |

| Gly | Ser | Thr | Ala | Glu | Asn | Ala | Glu | Tyr | Leu | Arg | Val | Ala | Pro | Gln |
|-----|-----|-----|-----|-----|-----|-----|-----|-----|-----|-----|-----|-----|-----|-----|
| 1190 | | | | | 1195 | | | | | 1200 | | | | |

| Ser | Ser | Glu | Phe | Ile | Gly | Ala |
|-----|-----|-----|-----|-----|-----|-----|
| 1205 | | | | | 1210 | |

<210> SEQ ID NO 7
<211> LENGTH: 1764
<212> TYPE: DNA
<213> ORGANISM: Homo sapiens

<400> SEQUENCE: 7

```
gcaggtgccc cgaaaagggg gcggggtcag gggtgccctg aactccgaat gcgaagttct      60
gtcttgtcat agccaagcac gctgcttctt ggattgacct ggcaggatgg cgccaccacc     120
agctagagta catctaggtg cgttcctggc agtgactccg aatcccggga gcgcagcgag     180
tgggacagag gcagccgcgg ccacacccag caaagtgtgg ggctcttccg cggggaggat     240
tgaaccacga ggcgggggcc gaggagcgct ccctacctcc atgggacagc acggacccag     300
tgcccgggcc cgggcagggc gcgccccagg acccaggccg gcgcgggaag ccagccctcg     360
gctccgggtc cacaagacct tcaagtttgt cgtcgtcggg gtcctgctgc aggtcgtacc     420
tagctcagct gcaaccatca aacttcatga tcaatcaatt ggcacacagc aatgggaaca     480
tagcccttg ggagagttgt gtccaccagg atctcataga tcagaacatc ctggagcctg      540
taaccggtgc acagagggtg tgggttacac caatgcttcc aacaatttgt ttgcttgcct     600
cccatgtaca gcttgtaaat cagatgaaga agagagaagt ccctgcacca cgaccaggaa     660
cacagcatgt cagtgcaaac caggaacttt ccggaatgac aattctgctg agatgtgccg     720
gaagtgcagc agagggtgcc ccagagggat ggtcaaggtc aaggattgta cgccctggag     780
tgacatcgag tgtgtccaca agaatcagg caatggacat aatatatggg tgattttggt      840
tgtgactttg gttgttccgt tgctgttggt ggctgtgctg attgtctgtt gttgcatcgg     900
ctcaggttgt ggaggggacc ccaagtgcat ggacagggtg tgtttctggc gcttgggtct     960
cctacgaggg cctggggctg aggacaatgc tcacaacgag attctgagca acgcagactc    1020
gctgtccact ttcgtctctg agcagcaaat ggaaagccag gagccggcag atttgacagg    1080
tgtcactgta cagtccccag gggaggcaca gtgtctgctg ggaccggcag aagctgaagg    1140
gtctcagagg aggaggctgc tggttccagc aaatggtgct gaccccactg agactctgat    1200
gctgttcttt gacaagtttg caaacatcgt gcccttgac tcctgggacc agctcatgag     1260
gcagctggac ctcacgaaaa atgagatcga tgtggtcaga gctggtacag caggcccagg    1320
ggatgccttg tatgcaatgc tgatgaaatg ggtcaacaaa actggacgga acgcctcgat    1380
ccacacctg ctggatgcct tggagaggat ggaagagaga catgcaagag agaagattca     1440
ggacctcttg gtggactctg gaagttcat ctacttagaa gatggcacag gctctgccgt      1500
gtccttggag tgaagactc ttttaccag aggtttcctc ttaggtgtta ggagttaata      1560
catattaggt ttttttttt tttaacatgt atacaaagta aattcttagc caggtgtagt     1620
```

```
ggctcatgcc tgtaatccca gcactttggg aggctgaggc gggtggatca cttgaggtca    1680
gaagttcaag accagcctga ccaacatcgt gaaatgccgt ctttacaaaa aaatacaaaa    1740
attaactgga aaaaaaaaaa aaaa                                           1764
```

<210> SEQ ID NO 8
<211> LENGTH: 468
<212> TYPE: PRT
<213> ORGANISM: Homo sapiens

<400> SEQUENCE: 8

```
Met Ala Pro Pro Ala Arg Val His Leu Gly Ala Phe Leu Ala Val
1               5                   10                  15

Thr Pro Asn Pro Gly Ser Ala Ala Ser Gly Thr Glu Ala Ala Ala
                20                  25                  30

Thr Pro Ser Lys Val Trp Gly Ser Ala Gly Arg Ile Glu Pro Arg
                35                  40                  45

Gly Gly Gly Arg Gly Ala Leu Pro Thr Ser Met Gly Gln His Gly Pro
    50                  55                  60

Ser Ala Arg Ala Arg Ala Gly Arg Ala Pro Gly Pro Arg Pro Ala Arg
65                  70                  75                  80

Glu Ala Ser Pro Arg Leu Arg Val His Lys Thr Phe Lys Phe Val Val
                85                  90                  95

Val Gly Val Leu Leu Gln Val Val Pro Ser Ser Ala Ala Thr Ile Lys
                100                 105                 110

Leu His Asp Gln Ser Ile Gly Thr Gln Gln Trp Glu His Ser Pro Leu
                115                 120                 125

Gly Glu Leu Cys Pro Pro Gly Ser His Arg Ser Glu His Pro Gly Ala
    130                 135                 140

Cys Asn Arg Cys Thr Glu Gly Val Gly Tyr Thr Asn Ala Ser Asn Asn
145                 150                 155                 160

Leu Phe Ala Cys Leu Pro Cys Thr Ala Cys Lys Ser Asp Glu Glu Glu
                165                 170                 175

Arg Ser Pro Cys Thr Thr Thr Arg Asn Thr Ala Cys Gln Cys Lys Pro
                180                 185                 190

Gly Thr Phe Arg Asn Asp Asn Ser Ala Glu Met Cys Arg Lys Cys Ser
                195                 200                 205

Arg Gly Cys Pro Arg Gly Met Val Lys Val Lys Asp Cys Thr Pro Trp
    210                 215                 220

Ser Asp Ile Glu Cys Val His Lys Glu Ser Gly Asn Gly His Asn Ile
225                 230                 235                 240

Trp Val Ile Leu Val Val Thr Leu Val Val Pro Leu Leu Leu Val Ala
                245                 250                 255

Val Leu Ile Val Cys Cys Cys Ile Gly Ser Gly Cys Gly Gly Asp Pro
                260                 265                 270

Lys Cys Met Asp Arg Val Cys Phe Trp Arg Leu Gly Leu Leu Arg Gly
                275                 280                 285

Pro Gly Ala Glu Asp Asn Ala His Asn Glu Ile Leu Ser Asn Ala Asp
    290                 295                 300

Ser Leu Ser Thr Phe Val Ser Glu Gln Gln Met Glu Ser Gln Glu Pro
305                 310                 315                 320

Ala Asp Leu Thr Gly Val Thr Val Gln Ser Pro Gly Glu Ala Gln Cys
                325                 330                 335
```

```
Leu Leu Gly Pro Ala Glu Ala Glu Gly Ser Gln Arg Arg Leu Leu
            340                 345                 350

Val Pro Ala Asn Gly Ala Asp Pro Thr Glu Thr Leu Met Leu Phe Phe
        355                 360                 365

Asp Lys Phe Ala Asn Ile Val Pro Phe Asp Ser Trp Asp Gln Leu Met
    370                 375                 380

Arg Gln Leu Asp Leu Thr Lys Asn Glu Ile Asp Val Val Arg Ala Gly
385                 390                 395                 400

Thr Ala Gly Pro Gly Asp Ala Leu Tyr Ala Met Leu Met Lys Trp Val
                405                 410                 415

Asn Lys Thr Gly Arg Asn Ala Ser Ile His Thr Leu Leu Asp Ala Leu
            420                 425                 430

Glu Arg Met Glu Glu Arg His Ala Arg Glu Lys Ile Gln Asp Leu Leu
        435                 440                 445

Val Asp Ser Gly Lys Phe Ile Tyr Leu Glu Asp Gly Thr Gly Ser Ala
    450                 455                 460

Val Ser Leu Glu
465

<210> SEQ ID NO 9
<211> LENGTH: 4154
<212> TYPE: DNA
<213> ORGANISM: Homo sapiens

<400> SEQUENCE: 9
acttggacgc gcttgcggag gattgcgttg acgagactct tatttattgt caccaacctg      60
tggtggaatt tgcagttgca cattggatct gattcgcccc gccccgaatg acgcctgccc     120
ggaggcagtg aaagtacagc cgcgccgccc caagtcagcc tggacacata atcagcacg      180 cggccggaga accccgcaat ctctgcgccc acaaaataca ccgacgatgc ccgatctact     240
ttaagggctg aaacccacgg gcctgagaga ctataagagc gttccctacc gccatggaac     300
aacggggaca gaacgccccg ccgcttcgg gggcccggaa aaggcacggc ccaggaccca     360
gggaggcgcg gggagccagg cctgggcccc gggtccccaa gacccttgtg ctcgttgtcg     420
ccgcggtcct gctgttggtc tcagctgagt ctgctctgat cacccaacaa gacctagctc     480
cccagcagag agcggcccca caacaaaaga ggtccagccc ctcagaggga ttgtgtccac     540
ctggacacca tatctcagaa gacggtagag attgcatctc ctgcaaatat ggacaggact     600
atagcactca ctggaatgac ctccttttct gcttgcgctg caccaggtgt gattcaggtg     660
aagtggagct aagtccctgc accacgacca gaaacacagt gtgtcagtgc aagaaggca     720 ccttccggga agaagattct cctgagatgt gccggaagtg ccgcacaggg tgtcccagag     780
ggatggtcaa ggtcggtgat gtacaccct ggagtgacat cgaatgtgtc cacaaagaat     840
caggtacaaa gcacagtggg gaagtcccag ctgtggagga cggtgacc tccagcccag     900 ggactcctgc ctctccctgt tctctctcag gcatcatcat aggagtcaca gttgcagccg     960
tagtcttgat tgtggctgtg tttgtttgca agtctttact gtggaagaaa gtccttcctt    1020
acctgaaagg catctgctca ggtggtggtg gggaccctga gcgtgtggac agaagctcac    1080
aacgacctgg ggctgaggac aatgtcctca tgagatcgt gagtatcttg cagcccaccc    1140
aggtccctga gcaggaaatg gaagtccagg agccagcaga gccaacaggt gtcaacatgt    1200
tgtcccccgg ggagtcagag catctgctgg aaccggcaga agctgaaagg tctcagagga    1260
ggaggctgct ggttccagca aatgaaggtg atcccactga gactctgaga cagtgcttcg    1320
```

| | |
|---|---|
| atgactttgc agacttggtg ccctttgact cctgggagcc gctcatgagg aagttgggcc | 1380 |
| tcatggacaa tgagataaag gtggctaaag ctgaggcagc gggccacagg gacaccttgt | 1440 |
| acacgatgct gataaagtgg gtcaacaaaa ccgggcgaga tgcctctgtc cacaccctgc | 1500 |
| tggatgcctt ggagacgctg ggagagagac ttgccaagca gaagattgag gaccacttgt | 1560 |
| tgagctctgg aaagttcatg tatctagaag gtaatgcaga ctctgccatg tcctaagtgt | 1620 |
| gattctcttc aggaagtcag accttccctg gtttaccttt tttctggaaa agcccaact | 1680 |
| ggactccagt cagtaggaaa gtgccacaat tgtcacatga ccggtactgg aagaaactct | 1740 |
| cccatccaac atcacccagt ggatggaaca tcctgtaact tttcactgca cttggcatta | 1800 |
| tttttataag ctgaatgtga taataaggac actatggaaa tgtctggatc attccgtttg | 1860 |
| tgcgtacttt gagatttggt ttgggatgtc attgttttca cagcactttt ttatcctaat | 1920 |
| gtaaatgctt tatttattta tttgggctac attgtaagat ccatctacac agtcgttgtc | 1980 |
| cgacttcact tgatactata tgatatgaac cttttttggg tgggggggtgc ggggcagttc | 2040 |
| actctgtctc ccaggctgga gtgcaatggt gcaatcttgg ctcactatag ccttgacctc | 2100 |
| tcaggctcaa gcgattctcc cacctcagcc atccaaatag ctgggaccac aggtgtgcac | 2160 |
| caccacgccc ggctaatttt ttgtattttg tctagatata ggggctctct atgttgctca | 2220 |
| gggtggtctc gaattcctgg actcaagcag tctgcccacc tcagactccc aaagcggtgg | 2280 |
| aattagaggc gtgagccccc atgcttggcc ttacctttct acttttataa ttctgtatgt | 2340 |
| tattatttta tgaacatgaa gaaactttag taaatgtact tgtttacata gttatgtgaa | 2400 |
| tagattagat aaacataaaa ggaggagaca tacaatgggg gaagaagaag aagtcccctg | 2460 |
| taagatgtca ctgtctgggt tccagccctc cctcagatgt actttggctt caatgattgg | 2520 |
| caacttctac aggggccagt cttttgaact ggacaacctt acaagtatat gagtattatt | 2580 |
| tataggtagt tgtttacata tgagtcggga ccaaagagaa ctggatccac gtgaagtcct | 2640 |
| gtgtgtggct ggtccctacc tgggcagtct catttgcacc catagccccc atctatggac | 2700 |
| aggctgggac agaggcagat gggttagatc acacataaca ataggtcta tgtcatatcc | 2760 |
| caagtgaact tgagccctgt ttgggctcag gagatagaag acaaaatctg tctcccacgt | 2820 |
| ctgccatggc atcaaggggg aagagtagat ggtgcttgag aatggtgtga aatggttgcc | 2880 |
| atctcaggag tagatggccc ggctcacttc tggttatctg tcaccctgag cccatgagct | 2940 |
| gcctttagg gtacagattg cctacttgag gaccttggcc gctctgtaag catctgactc | 3000 |
| atctcagaaa tgtcaattct taaacactgt ggcaacagga cctagaatgg ctgacgcatt | 3060 |
| aaggttttct tcttgtgtcc tgttctatta ttgttttaag acctcagtaa ccatttcagc | 3120 |
| ctctttccag caaacccttc tccatagtat ttcagtcatg gaaggatcat ttatgcaggt | 3180 |
| agtcattcca ggagtttttg gtcttttctg tctcaaggca ttgtgtgttt gttccggga | 3240 |
| ctggtttggg tgggacaaag ttagaattgc ctgaagatca cacattcaga ctgttgtgtc | 3300 |
| tgtggagttt taggagtggg gggtgacctt tctggtcttt gcacttccat cctctcccac | 3360 |
| ttccatctgg catcccacgc gttgtcccct gcacttctgg aaggcacagg gtgctgctgc | 3420 |
| ctcctggtct ttgcctttgc tgggccttct gtgcaggacg ctcagcctca gggctcagaa | 3480 |
| ggtgccagtc cggtcccagg tcccttgtcc cttccacaga ggccttccta aagatgcat | 3540 |
| ctagagtgtc agccttatca gtgtttaaga ttttctttt attttaatt tttttgagac | 3600 |
| agaatctcac tctctcgccc aggctggagt gcaacggtac gatcttggct cagtgcaacc | 3660 |

-continued

```
tccgcctcct gggttcaagc gattctcgtg cctcagcctc cggagtagct gggattgcag    3720
gcacccgcca ccacgcctgg ctaattttg tatttttagt agagacgggg tttcaccatg     3780
ttggtcaggc tggtctcgaa ctcctgacct caggtgatcc accttggcct ccgaaagtgc    3840
tgggattaca ggcgtgagcc accagccagg ccaagctatt cttttaaagt aagcttcctg    3900
acgacatgaa ataattgggg gttttgttgt ttagttacat taggctttgc tatatcccca    3960
ggccaaatag catgtgacac aggacagcca tagtatagtg tgtcactcgt ggttggtgtc    4020 cttcatgct tctgccctgt caaggtccc tatttgaaat gtgttataat acaaacaagg      4080
aagcacattg tgtacaaaat acttatgtat ttatgaatcc atgaccaaat taaatatgaa    4140
accttatata aaaa                                                       4154
```

<210> SEQ ID NO 10
<211> LENGTH: 440
<212> TYPE: PRT
<213> ORGANISM: Homo sapiens

<400> SEQUENCE: 10

```
Met Glu Gln Arg Gly Gln Asn Ala Pro Ala Ser Gly Ala Arg Lys
1               5                   10                  15

Arg His Gly Pro Gly Pro Arg Glu Ala Arg Gly Ala Arg Pro Gly Pro
                20                  25                  30

Arg Val Pro Lys Thr Leu Val Leu Val Ala Val Leu Leu Leu
                35              40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Val Pro
                180                 185                 190

Ala Val Glu Glu Thr Val Thr Ser Ser Pro Gly Thr Pro Ala Ser Pro
            195                 200                 205

Cys Ser Leu Ser Gly Ile Ile Ile Gly Val Thr Val Ala Ala Val Val
    210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Asp Pro Glu
                245                 250                 255

Arg Val Asp Arg Ser Ser Gln Arg Pro Gly Ala Glu Asp Asn Val Leu
                260                 265                 270

Asn Glu Ile Val Ser Ile Leu Gln Pro Thr Gln Val Pro Glu Gln Glu
            275                 280                 285
```

-continued

```
Met Glu Val Gln Glu Pro Ala Glu Pro Thr Gly Val Asn Met Leu Ser
    290                 295                 300
Pro Gly Glu Ser Glu His Leu Leu Glu Pro Ala Glu Ala Glu Arg Ser
305                 310                 315                 320
Gln Arg Arg Leu Leu Val Pro Ala Asn Glu Gly Asp Pro Thr Glu
                325                 330                 335
Thr Leu Arg Gln Cys Phe Asp Asp Phe Ala Asp Leu Val Pro Phe Asp
                340                 345                 350
Ser Trp Glu Pro Leu Met Arg Lys Leu Gly Leu Met Asp Asn Glu Ile
            355                 360                 365
Lys Val Ala Lys Ala Glu Ala Ala Gly His Arg Asp Thr Leu Tyr Thr
    370                 375                 380
Met Leu Ile Lys Trp Val Asn Lys Thr Gly Arg Asp Ala Ser Val His
385                 390                 395                 400
Thr Leu Leu Asp Ala Leu Glu Thr Leu Gly Glu Arg Leu Ala Lys Gln
                405                 410                 415
Lys Ile Glu Asp His Leu Leu Ser Ser Gly Lys Phe Met Tyr Leu Glu
            420                 425                 430
Gly Asn Ala Asp Ser Ala Met Ser
            435                 440
```